US008747910B2

(12) United States Patent
Jirström et al.

(10) Patent No.: US 8,747,910 B2
(45) Date of Patent: Jun. 10, 2014

(54) PREDICTION OF RESPONSE TO PLATINUM-BASED THERAPY

(75) Inventors: Karin Jirström, Limhamn (SE); Jakob Eberhard, Lund (SE)

(73) Assignee: Atlas Antibodies AB, Stockholm (SE)

( * ) Notice: Subject to any disclaimer, the term of this patent is extended or adjusted under 35 U.S.C. 154(b) by 0 days.

(21) Appl. No.: 13/201,689

(22) PCT Filed: Feb. 16, 2010

(86) PCT No.: PCT/EP2010/051941
§ 371 (c)(1),
(2), (4) Date: Oct. 25, 2011

(87) PCT Pub. No.: WO2010/092190
PCT Pub. Date: Aug. 19, 2010

(65) Prior Publication Data
US 2012/0034317 A1 Feb. 9, 2012

Related U.S. Application Data

(60) Provisional application No. 61/169,963, filed on Apr. 16, 2009, provisional application No. 61/233,769, filed on Aug. 13, 2009.

(30) Foreign Application Priority Data

| Feb. 16, 2009 | (WO) | PCT/SE2009/000091 |
| Apr. 16, 2009 | (EP) | 09158084 |
| Aug. 13, 2009 | (EP) | 09167847 |
| Dec. 17, 2009 | (WO) | PCT/EP2009/067419 |

(51) Int. Cl.
| *A61K 31/282* | (2006.01) |
| *G01N 33/53* | (2006.01) |
| *G01N 33/574* | (2006.01) |
| *C12Q 1/68* | (2006.01) |

(52) U.S. Cl.
USPC .......... 424/649; 435/6.11; 435/6.14; 435/7.1; 435/7.23

(58) Field of Classification Search
CPC .................................................. A61K 31/282
USPC ................. 424/649; 435/7.1, 7.23, 6.11, 6.14
See application file for complete search history.

(56) References Cited

U.S. PATENT DOCUMENTS

| 2009/0252784 A1 | 10/2009 | Houchen et al. | |
| 2012/0040338 A1* | 2/2012 | Jirstrom et al. | 435/6.1 |
| 2012/0058202 A1* | 3/2012 | Uhlen et al. | 424/649 |

FOREIGN PATENT DOCUMENTS

| WO | WO 2007/027906 A2 | 3/2007 |
| WO | WO 2007/084485 A2 | 7/2007 |
| WO | WO 2009/102261 A1 | 8/2009 |

OTHER PUBLICATIONS

Martinez-Arribas (Journal of Cellular Biochemistry (2006) vol. 97, pp. 1275-1282).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Kaiser (Science, 2006, 313: 1370).*
Baldi, A et al., "Identification of genes down-regulated during melanoma progression: a cDNA array study", *Exp. Dermatol.*, 2003, vol. 12, pp. 213-218.
Danno, S et al., "Decreased expression of mouse Rbm3, a cold-shock protein, in Sertoli cells of cryptorchild testis", *Am. J. Pathol.*, vol. 156, No. 5, May 2000, pp. 1685-1692.
Dresios, J et al., "Cold stress-induced protein Rbm3 binds 60S ribosomal subunits, alters microRNA levels, and enhances global protein synthesis", *Proc. Natl. Acad. Sci. USA*, vol. 102, No. 6, Feb. 8, 2005, pp. 1865-1870.
European Office Action Corresponding to European Application No. 10 704 928.0; Dated, Dec. 16, 2011; 7 pages.
European Office Action Corresponding to European Application No. 10 704 927.2; Dated, Jan. 9, 2012; 6 pages.
European Office Action Corresponding to European Application No. 10 705 141.9; Dated Feb. 13, 2012; 7 pages.
European Office Action Corresponding to European Application No. 09 803 750.0; Dated Feb. 13, 2012; 7 pages.
International Preliminary Report on Patentability Corresponding to International Application No. PCT/EP2010/051941; Date of Mailing: May 18, 2011; 11 pages.
International Search Report Corresponding to International Application No. PCT/EP2010/051941; Date of Mailing: Sep. 7, 2010; 19 pages.
Jogi, A et al., "Nuclear expression of the RNA-binding protein RBM3 is associated with an improved clinical outcome in breast cancer", *Modern Pathol.*, vol. 22, 2009, pp. 1564-1574.

(Continued)

*Primary Examiner* — Mark Halvorson
*Assistant Examiner* — Yan Xiao
(74) *Attorney, Agent, or Firm* — Myers Bigel Sibley & Sajovec, P.A.

(57) ABSTRACT

Method for determining whether a mammalian subject having a cancer belongs to a first or a second group, wherein subjects of the first group are more likely to respond to a platinum-based therapy than subjects of the second group, comprising the steps of: evaluating the amount of RBM3 protein or RBM3 mRNA present in at least part of a sample earlier obtained from said subject, and determining a sample value corresponding to said amount; comparing the sample value with a reference value; and, if said sample value is higher than said reference value, concluding that said subject belongs to a first group; and if said sample value is lower than or equal to said reference value, concluding that said subject belongs to a second group. There is further provided means useful in the establishment of a treatment prediction.

18 Claims, 24 Drawing Sheets

(56) References Cited

OTHER PUBLICATIONS

Lleonart, ME., "A new generation of proto-oncogenes: Cold-inducible RNA binding proteins", *Biochim. Biophys. Acta*, vol. 1805, No. 1, Jan. 1, 2010, pp. 43-52.

Martinez-Arribas, F et al., "Positive correlation between the expression of X-chromosome RBM genes (RBMX, RBM3, rBM10) and the proapoptotic Bax gene in human breast cancer", *J. Cell. Biochem.*, vol. 97, No. 6, 2006, pp. 1275-1282.

Mourtada-Maarabouni, M et al., "The antiapoptotic RBM5/LUCA-15/H37 gene and its role in apoptosis and human cancer; Research update", *Scientific World J.*, vol. 6, pp. 1705-1712, Mar. 15, 2007.

Natarajan, G et al., "RNA binding protein RBM3: A novel protooncogene required for tumor cells to overcome G2/M arrest and mitotic catastrophe", *Gastroenterology*, vol. 134, No. 4, Apr. 1, 2008, p. A-86.

Nilsson, P. et al., "Towards a human proteome atlas: High-throughput generation of mono-specific antibodies for tissue profiling", *Proteomics*, vol. 5, 2005, pp. 4327-4337.

Price, P. et al., "The growth rate of metastatic non-seminomatous germ cell testicular tumours measured by marker production doubling time-II. Prognostic significance in patients treated by chemotherapy", *Eur. J. Cancer*, vol. 26, No. 4, pp. 453-457, 1990.

Richie, JP, "OCT4 staining in testicular tumors. A sensitive and specific marker for seminoma and embryonal carcinoma", *J. Urol.*, 174 (2), 2005, pp. 569-570.

Slootstra, JW et al., "Structural aspects of antibody-antigen interaction revealed through small random peptide libraries", *Mol. Diversity*, vol. 1, 1995, pp. 87-96.

Sureban, SM et al., "Translation regulatory factor RBM3 is a proto-oncogene that prevents mitotic catastrophe", *Oncogene*, Vo. 27, No. 33, Jul. 1, 2008, pp. 4544-4556.

Sutherland, LC et al., "RNA binding motif (RBM) proteins: A novel family of apoptosis modulators?" *J. Cell. Biochem.*, vol. 94, 2005, pp. 5-24.

Walsh, CS et al., "ERCC5 is a novel biomarker of ovarian cancer prognosis", *J. Clin. Oncol.*, vol. 26, No. 18, Jun. 20, 2008, pp. 2952-2958.

Wellmann, S et al., "The RNA-binding protein RBM3 Is required for cell proliferation and protects against serum deprivation-induced cell death", *Pediatric Res.*, vol. 67, No. 1, 2010, pp. 35-41.

Zeng, Y et al., "Down-regulating cold shock protein genes impairs cancer cell survival and enhances chemosensitivity", *J. Cell. Biochem.*, vol. 107, No. 1, Mar. 10, 2009, pp. 179-188.

Australian Application No. 2010212772; office action mailed Aug. 29, 2013.

Yagoda, "Future Implications of Phase 2 Chemotherapy Trials in Ninety-five Patients with Measurable Advanced Bladder Cancer," Cancer Res. 37, 2775-2780 (1977).

\* cited by examiner

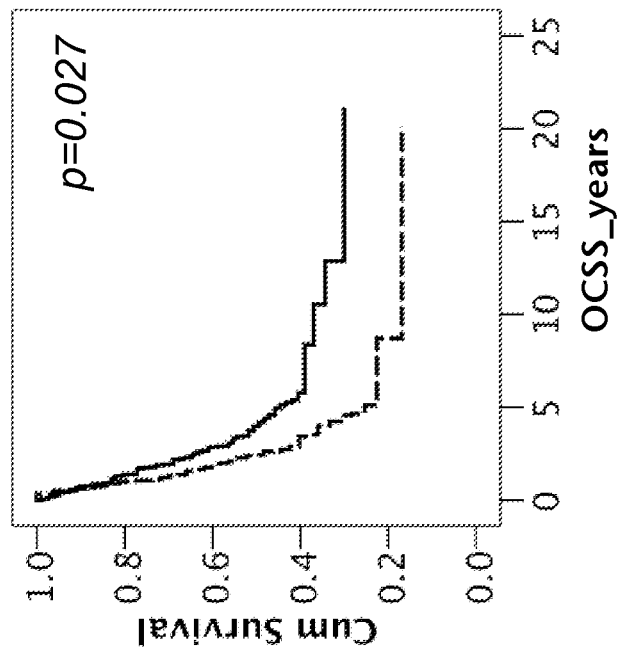
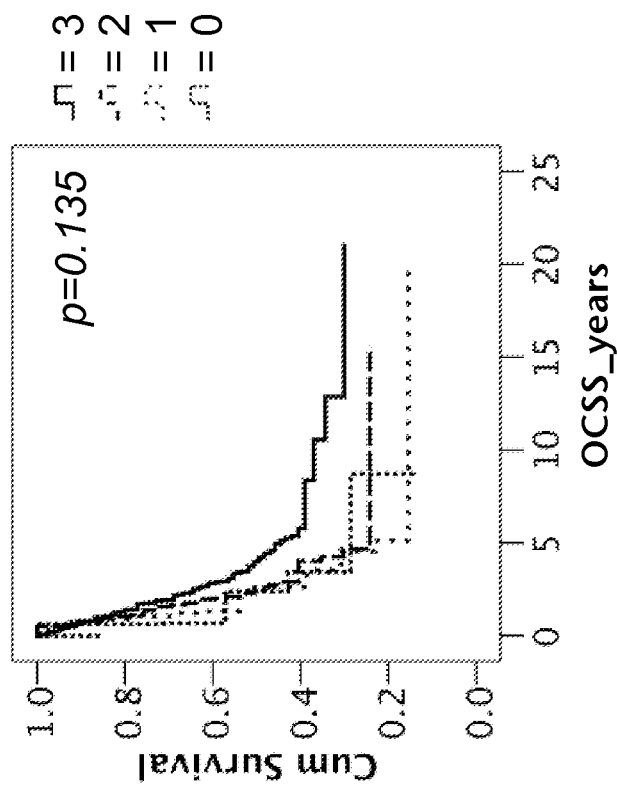
FIGURE 3B
FIGURE 3A

SEQUENCE LISTING

<160> NUMBER OF SEQ ID NOS: 21

<210> SEQ ID NO 1
<211> LENGTH: 134
<212> TYPE: PRT
<213> ORGANISM: Homo sapiens

<400> SEQUENCE: 1

Asp Glu Gln Ala Leu Glu Asp His Phe Ser Ser Phe Gly Pro Ile Ser
1               5                   10                  15

Glu Val Val Val Lys Asp Arg Glu Thr Gln Arg Ser Arg Gly Phe
            20                  25                  30

Gly Phe Ile Thr Phe Thr Asn Pro Glu His Ala Ser Val Ala Met Arg
        35                  40                  45

Ala Met Asn Gly Glu Ser Leu Asp Gly Arg Gln Ile Arg Val Asp His
    50                  55                  60

Ala Gly Lys Ser Ala Arg Gly Thr Arg Gly Gly Phe Gly Ala His
65                  70                  75                  80

Gly Arg Gly Arg Ser Tyr Ser Arg Gly Gly Asp Gln Gly Tyr Gly
                85                  90                  95

Ser Gly Arg Tyr Tyr Asp Ser Arg Pro Gly Gly Tyr Gly Tyr Gly Tyr
            100                 105                 110

Gly Arg Ser Arg Asp Tyr Asn Gly Arg Asn Gln Gly Gly Tyr Asp Arg
            115                 120                 125

Tyr Ser Gly Gly Asn Tyr
    130

<210> SEQ ID NO 2
<211> LENGTH: 157
<212> TYPE: PRT
<213> ORGANISM: Homo sapiens

<400> SEQUENCE: 2

Met Ser Ser Glu Glu Gly Lys Leu Phe Val Gly Gly Leu Asn Phe Asn
1               5                   10                  15

Thr Asp Glu Gln Ala Leu Glu Asp His Phe Ser Ser Phe Gly Pro Ile
            20                  25                  30

Ser Glu Val Val Val Lys Asp Arg Glu Thr Gln Arg Ser Arg Gly
        35                  40                  45

Phe Gly Phe Ile Thr Phe Thr Asn Pro Glu His Ala Ser Val Ala Met
    50                  55                  60

Arg Ala Met Asn Gly Glu Ser Leu Asp Gly Arg Gln Ile Arg Val Asp
65                  70                  75                  80

His Ala Gly Lys Ser Ala Arg Gly Thr Arg Gly Gly Phe Gly Ala
                85                  90                  95

His Gly Arg Gly Arg Ser Tyr Ser Arg Gly Gly Asp Gln Gly Tyr
            100                 105                 110

Gly Ser Gly Arg Tyr Tyr Asp Ser Arg Pro Gly Gly Tyr Gly Tyr Gly
            115                 120                 125

Tyr Gly Arg Ser Arg Asp Tyr Asn Gly Arg Asn Gln Gly Gly Tyr Asp
    130                 135                 140

Arg Tyr Ser Gly Gly Asn Tyr Arg Asp Asn Tyr Asp Asn
145                 150                 155

<210> SEQ ID NO 3
<211> LENGTH: 1130

```
<212> TYPE: DNA
<213> ORGANISM: Homo sapiens

<400> SEQUENCE: 3
atgcgcaatg tggcccccta atggtggctg cgctgagcca gctcctcaga ttaccacctt    60
attggccgcc tttctcagct tttctgtagt tacccatatt ttgttcctct ttcttgtcta   120
ttttctgtgc tttttctctg ctttccgtct cgctattttc tcacatctcc attttctttc   180
tccttcctgc caccattctt catgttcttc ccacaggact tgaactgcca tgtcctctga   240
agaaggaaag ctcttcgtgg agggctcaa ctttaacacc gacgagcagg cactggaaga    300
ccacttcagc agtttcggac ctatctctga ggtggtcgtt gtcaaggacc gggagactca   360
gcggtccagg ggttttggtt tcatcacctt caccaaccca gagcatgctt cagttgccat   420
gagagccatg aacggagagt ctctggatgg tcgtcagatc cgtgtggatc atgcaggcaa   480
gtctgctcgg ggaaccagag gaggtggctt tggggcccat gggcgtggtc gcagctactc   540
tagaggtggt ggggaccagg gctatgggag tggcaggtat tatgacagtc gacctggagg   600
gtatggatat ggatatggac gttccagaga ctataatggc agaaaccagg gtggttatga   660
ccgctactca ggaggaaatt acagagacaa ttatgacaac tgaaatgaga catgcacata   720
atatagatac acaaggaata atttctgatc caggatcgtc cttccaaatg ctgtatttta   780 aaggtttt tggagctgca ccgaagcatc ttattttata gtatatcaac cttttgtttt    840
taaattgacc tgccaaggta gctgaagacc ttttagacag ttccatcttt tttttaaat    900 tttttctgcc tatttaaaga caaattatgg gacgtttgta gaacctgagt attttctctt   960
ttaccagttt tttagtttga gctcttaggt ttattggagc tagcaataat tggttctggc  1020
aagtttggcc agactgactt caaaaaatta atgtgtatcc agggacattt taaaaacctg  1080
tacacagtgt ttattgtggt taggaagcaa tttcccaatg tacctataag             1130

<210> SEQ ID NO 4
<211> LENGTH: 29
<212> TYPE: PRT
<213> ORGANISM: Homo sapiens

<400> SEQUENCE: 4

Arg Gly Phe Gly Phe Ile Thr Phe Thr Asn Pro Glu His Ala Ser Val
1               5                   10                  15

Ala Met Arg Ala Met Asn Gly Glu Ser Leu Asp Gly Arg
            20                  25

<210> SEQ ID NO 5
<211> LENGTH: 24
<212> TYPE: PRT
<213> ORGANISM: Homo sapiens

<400> SEQUENCE: 5

Arg Ser Tyr Ser Arg Gly Gly Gly Asp Gln Gly Tyr Gly Ser Gly Arg
1               5                   10                  15

Tyr Tyr Asp Ser Arg Pro Gly Gly
            20

<210> SEQ ID NO 6
<211> LENGTH: 5
<212> TYPE: PRT
<213> ORGANISM: Homo sapiens

<400> SEQUENCE: 6

Thr Phe Thr Asn Pro
```

```
<210> SEQ ID NO 7
<211> LENGTH: 10
<212> TYPE: PRT
<213> ORGANISM: Homo sapiens

<400> SEQUENCE: 7

Gly Thr Arg Gly Gly Gly Phe Gly Ala His
1               5                   10

<210> SEQ ID NO 8
<211> LENGTH: 10
<212> TYPE: PRT
<213> ORGANISM: Homo sapiens

<400> SEQUENCE: 8

Gly Phe Gly Ala His Gly Arg Gly Arg Ser
1               5                   10

<210> SEQ ID NO 9
<211> LENGTH: 5
<212> TYPE: PRT
<213> ORGANISM: Homo sapiens

<400> SEQUENCE: 9

Tyr Asp Arg Tyr Ser
1               5

<210> SEQ ID NO 10
<211> LENGTH: 9
<212> TYPE: PRT
<213> ORGANISM: Homo sapiens

<400> SEQUENCE: 10

Asp Glu Gln Ala Leu Glu Asp His Phe
1               5

<210> SEQ ID NO 11
<211> LENGTH: 7
<212> TYPE: PRT
<213> ORGANISM: Homo sapiens

<400> SEQUENCE: 11

Thr Asn Pro Glu His Ala Ser
1               5

<210> SEQ ID NO 12
<211> LENGTH: 10
<212> TYPE: PRT
<213> ORGANISM: Homo sapiens

<400> SEQUENCE: 12

Glu His Ala Ser Val Ala Met Arg Ala Met
1               5                   10

<210> SEQ ID NO 13
<211> LENGTH: 10
<212> TYPE: PRT
<213> ORGANISM: Homo sapiens

<400> SEQUENCE: 13

Arg Gly Gly Gly Phe Gly Ala His Gly Arg
1               5                   10
```

```
<210> SEQ ID NO 14
<211> LENGTH: 8
<212> TYPE: PRT
<213> ORGANISM: Homo sapiens

<400> SEQUENCE: 14

Gly Phe Gly Ala His Gly Arg Gly
1               5

<210> SEQ ID NO 15
<211> LENGTH: 9
<212> TYPE: PRT
<213> ORGANISM: Homo sapiens

<400> SEQUENCE: 15

Asp Tyr Asn Gly Arg Asn Gln Gly Gly
1               5

<210> SEQ ID NO 16
<211> LENGTH: 5
<212> TYPE: PRT
<213> ORGANISM: Homo sapiens

<400> SEQUENCE: 16

Ser Tyr Ser Arg Gly
1               5

<210> SEQ ID NO 17
<211> LENGTH: 11
<212> TYPE: PRT
<213> ORGANISM: Homo sapiens

<400> SEQUENCE: 17

Asp Gln Gly Tyr Gly Ser Gly Arg Tyr Tyr Asp
1               5                   10

<210> SEQ ID NO 18
<211> LENGTH: 6
<212> TYPE: PRT
<213> ORGANISM: Homo sapiens

<400> SEQUENCE: 18

Ser Tyr Ser Arg Gly Gly
1               5

<210> SEQ ID NO 19
<211> LENGTH: 3
<212> TYPE: PRT
<213> ORGANISM: Homo sapiens

<400> SEQUENCE: 19

Asp Glu Gln
1

<210> SEQ ID NO 20
<211> LENGTH: 19
<212> TYPE: DNA
<213> ORGANISM: Homo sapiens

<400> SEQUENCE: 20
gacgagcagg cactggaag                                                  19

<210> SEQ ID NO 21
<211> LENGTH: 20
<212> TYPE: DNA
<213> ORGANISM: Homo sapiens
```

```
<400> SEQUENCE: 21
gtaatttcct cctgagtagc                                           20
```

PREDICTION OF RESPONSE TO PLATINUM-BASED THERAPY

RELATED APPLICATIONS

This application is a 35 U.S.C. §371 national phase application of PCT Application PCT/EP2010/051941, filed Feb. 16, 2010, which claims priority to PCT/SE2009/000091, filed Feb. 16, 2009. PCT Application PCT/EP2010/051941 also claims priority to U.S. Provisional Application No. 61/169,963 filed Apr. 16, 2009, EP 09158084.5, filed Apr. 16, 2009, U.S. Provisional Application No. 61/233,769, filed Aug. 13, 2009, EP 09167847.4, filed Aug. 13, 2009, and PCT/EP2009/067419, filed Dec. 17, 2009. The entire content of each of these applications is incorporated herein by reference.

TECHNICAL FIELD

The present invention relates to the field of cancer and in particular to treatment thereof. Further, it relates to means and methods useful in the establishment of a treatment prediction or a cancer subject's responsiveness to a cancer treatment.

BACKGROUND

Cancer

Cancer is one of the most common diseases, and a major cause of death in the western world. In general, incidence rates increase with age for most forms of cancer. As human populations continue to live longer, due to an increase of the general health status, cancer may affect an increasing number of individuals. The cause of most common cancer types is still largely unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. A malignant tumor does not only necessarily consist of the transformed tumor cells themselves but also surrounding normal cells which act as a supportive stroma. This recruited cancer stroma consists of connective tissue, blood vessels and various other normal cells, e.g., inflammatory cells, which act in concert to supply the transformed tumor cells with signals necessary for continued tumor growth.

The most common forms of cancer arise in somatic cells and are predominantly of epithelial origin, e.g., prostate, breast, colon, urothelium and skin, followed by cancers originating from the hematopoetic lineage, e.g., leukemia and lymphoma, neuroectoderm, e.g., malignant gliomas, and soft tissue tumors, e.g., sarcomas.

Cancer Diagnostics and Prognostics

Microscopic evaluation of biopsy material from suspected tumors remains the golden standard for cancer diagnostics. To obtain a firm diagnosis, the tumor tissue is fixated in formalin, histo-processed and paraffin embedded. From the resulting paraffin block, tissue sections can be produced and stained using both histochemical, i.e., hematoxylin-eosin staining, and immunohistochemical (IHC) methods. The surgical specimen is then evaluated with pathology techniques, including gross and microscopic analysis. This analysis often forms the basis for assigning a specific diagnosis, i.e., classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ. Staging of tumors is often based on several forms of examination, including surgical, radiological and histopathological analyses. In addition to staging, for most tumor types there is also a classification system to grade the level of malignancy. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and the Nottingham Histological Grade (NHG) grading for breast carcinomas.

Accurate staging and grading is crucial for a correct diagnosis and may provide an instrument to predict a prognosis. The diagnostic and prognostic information for a specific tumor subsequently determines an adequate therapeutic strategy for a given cancer patient. A commonly used method, in addition to histochemical staining of tissue sections, to obtain more information regarding a tumor is immunohistochemical staining. IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be involved in supporting the accurate diagnosis, including staging and grading, of a primary tumor as well as in the diagnostics of metastases of unknown origin. The most commonly used antibodies in clinical practice today include antibodies against cell type "specific" proteins, e.g., PSA (prostate), MelanA (melanocytes) and Thyroglobulin (thyroid gland), and antibodies recognizing intermediate filaments (epithelial, mesenchymal, glial), cluster of differentiation (CD) antigens (hematopoetic, sub-classification of lympoid cells) and markers of malignant potential, e.g., Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites adds relevant information. However, most of these analyses still represent basic research and have yet to be evaluated and standardized for the use in clinical medicine.

Platinum-Based Treatment

Platinum-based chemotherapy is used in treatment of cancers such as testicular, ovarian, cervical, lung, bladder, colorectal and head and neck cancer. Currently, there are three FDA-approved platinum-based compounds (cisplatin, carboplatin and oxaliplatin), but there are new derivatives being developed, or undergoing clinical trials (such as satraplatin and picoplatin). One goal in developing new platinum-based compounds is to minimize toxicity, which can be severe with the currently used compounds. Common side effects include kidney toxicity, nerve toxicity and loss of hearing.

Platinum Resistance

Platinum-based chemotherapeutic agents bind to DNA, thereby inducing DNA adducts, leading to cross-links that disrupt DNA structure. Usually, these damages ultimately lead to apoptosis. There is however a problem with drug resistance. A subset of tumours do not respond to conventional therapy, and this resistance could be either intrinsic or acquired.

The mechanism behind platinum resistance has not been fully elucidated, but two main pathways have been suggested: Either a failure of the platinum compound to reach target DNA, or a failure of the platinum compound to induce apoptosis after DNA adduct formation.

Failure of the platinum compound to reach tumor DNA could be due to the effect of certain proteins associated with multidrug resistance. There can also be other efflux proteins involved, for example those mediating copper transport.

A failure of the platinum compound to induce apoptosis is probably due to differences in DNA-repair systems. There are a number of mechanisms involved in DNA-repair, and particularly two of these have been associated with platinum resistance, Nucleotide excision repair (NER) and Mismtch repair (MMR).

With testicular cancer as a model system (these tumours are extremely sensitive to platinum-based chemotherapy), it has been shown that certain testicular carcinoma cell lines have a NER deficiency, in particular, low levels of excision repair cross-complementation group 1 (ERCC1) protein. In ovarian cancer cell lines it has been shown that cell lines developing cisplatin resistance had an increased ERCC1 expression.

There are indications that the MMR pathway needs to be functional in order for damages created by cisplatin and carboplatin to be detected by the cell. These compounds interfere with MMR activity, thus preventing damage repair, ultimately leading to apoptosis. If MMR is deficient, the cell can continue to proliferate with the DNA damage still present and will thereby be resistant. However, there seems to be a difference in MMR mediated resistance between different compounds; oxaliplatin may have effect in cells that are resistant to cisplatin and carboplatin.

Endpoint Analysis

Endpoint analysis for trials with adjuvant treatments for cancer gives important information on how the patients respond to a certain therapy. Overall survival (OS) has long been considered the standard primary endpoint. OS takes into account time to death, irrespective of cause, e.g. if the death is due to cancer or not. Loss to follow-up is censored and regional recurrence, distant metastases, second primary ovarian cancers and second other primary cancers are ignored.

Today, an increasing number of effective treatments available for many types of cancer have resulted in the need for surrogate endpoints to allow for a better evaluation of the effect of adjuvant treatments. Partly due to the long follow-up period required to demonstrate that adjuvant treatments improve OS, the endpoint is often complemented with other clinical endpoints that give an earlier indication on how successful the treatment is.

In the present disclosure, the inventors show that the level of expression of a particular protein (the proposed biomarker) significantly correlates with prognosis. For this observation, two surrogate endpoints were used, namely ovarian cancer-specific survival (OCSS) and recurrence free survival (RFS). Analysis of OCSS includes time to death caused by ovarian cancer due to the original tumor. RFS includes time to any event related to the same cancer, i.e., all cancer recurrences and deaths from the same cancer are events. Distant, local and regional metastases as well as ovarian cancer specific death are considered. On the other hand, second primary same cancers and other primary cancers are ignored. Deaths from other cancers, non-cancer-related deaths, treatment-related deaths, and loss to follow-up are censored observations.

SUMMARY OF THE PRESENT DISCLOSURE

There is an object of some aspects the present disclosure to provide for the prediction of the level of responsiveness to platinum-based treatment.

There is thus provided a method for determining whether a mammalian subject having a cancer belongs to a first or a second group, wherein subjects of the first group are more responsive to a platinum-based treatment than subjects of the second group. Further, there is provided a method for determining the level of intensity of a platinum-based treatment of a mammalian subject having a cancer. The methods are based on the evaluation of an amount of RBM3 protein or RBM3 mRNA present in at least part of a sample from the subject.

Still further, there is provided a kit for carrying out the methods, which comprises a quantifiable affinity ligand capable of selective interaction with an RBM3 protein and reagents necessary for quantifying the amount of said quantifiable affinity ligand.

Also, there is provided an RBM3 protein fragment and uses thereof, an affinity ligand capable of selective interaction with an RBM3 protein and uses thereof and a platinum-based therapeutic agent for use in treatment of a mammalian RBM3 high subject having a cancer.

BRIEF DESCRIPTION OF THE FIGURES

FIG. 1 shows the results of survival analyses of all patients, i.e. 154 subjects, diagnosed with epithelial ovarian cancer (EOC).

FIG. 2 shows the impact of RBM3 level on OS if splitting all 154 subjects into groups based on nuclear fraction (NF) staining.

FIG. 3 shows the impact of RBM3 level on OCSS if splitting all 154 subjects into groups based on nuclear fraction (NF) staining. In FIG. 3A all subjects were split into four groups based on NF status, i.e. <2% (0), 2-25% (1), >25-75% (2) or >75% (3). In FIG. 3B a solid line represents a high NF level of RBM3 (NF>75%), and a dotted line represents a low NF level of RBM3 (NF≤75%).

FIG. 5 shows OS in all 154 patients diagnosed with EOC based on nuclear intensity (NI) or cytoplasmic intensity (CI) levels of RBM3. RBM3 expression was dichotomized using the categories high and low.

FIG. 6 shows OCSS in all 154 patients diagnosed with EOC based on nuclear intensity (NI) or cytoplasmic intensity (CI) levels of RBM3. RBM3 expression was dichotomized using the categories high and low.

FIG. 7 shows the results of survival analyses for 39 patients diagnosed with grade 2 EOC based on the NF level of RBM3. RBM3 expression was dichotomized into high and low categories. A solid line represents a high RBM3 level (NF>75%), and a dotted line represents a low RBM3 level (NF≤75%).

FIG. 8 shows the results of survival analyses for 47 patients diagnosed with grade 1 or 2 EOC based on the NF level of RBM3. RBM3 expression was dichotomized into high and low categories. A solid line represents a high RBM3 level (NF>75%), and a dotted line represents a low RBM3 level (NF≤75%).

FIG. 9 shows the results of survival analyses for 42 patients diagnosed with stage I or II EOC based on the NF level of RBM3. RBM3 expression was dichotomized into high and low categories. A solid line represents a high RBM3 level (NF>75%), and a dotted line represents a low RBM3 level (NF≤75%).

FIG. 10 shows the results of survival analyses for 35 patients diagnosed with endometroid carcinoma based on the NF level of RBM3. RBM3 expression was dichotomized into high and low categories. A solid line represents a high RBM3 level (NF>75%), and a dotted line represents a low RBM3 level (NF≤75%).

FIG. 11 shows the results of survival analyses for 17 patients diagnosed with stage I or II endometroid carcinoma based on the NF level of RBM3. RBM3 expression was dichotomized into high and low categories. A solid line represents a high RBM3 level (NF>75%), and a dotted line represents a low RBM3 level (NF≤75%).

FIG. 12 shows the results of survival analyses for 90 patients diagnosed with serous carcinoma based on the NI level of RBM3. RBM3 expression was dichotomized into high and low categories. A solid line represents a high RBM3 level (NI=3), and a dotted line represents a low RBM3 level (NI<3).

FIG. 13 shows the results of survival analyses for 90 patients diagnosed with serous carcinoma based on the CI level of RBM3. RBM3 expression was dichotomized into high and low categories. A solid line represents a high RBM3 level (CI=2), and a dotted line represents a low RBM3 level (CI<2).

FIG. 14 shows the results of OS analyses for 23 patients diagnosed with grade 1 or 2 serous carcinoma based on the NI level of RBM3. RBM3 expression was dichotomized into high and low categories. A solid line represents a high RBM3 level (NI=3), and a dotted line represents a low RBM3 level (NI<3).

FIG. 15 shows the impact of RBM3 level on OS for patients diagnosed with epithelial ovarian cancer (EOC). All 149 subjects were stained with the 1B5 monoclonal antibody.

FIG. 16 shows the impact of RBM3 level on OCSS for patients diagnosed with epithelial ovarian cancer (EOC). All 149 subjects were stained with the 1B5 monoclonal antibody.

DETAILED DESCRIPTION

Figure 1A:
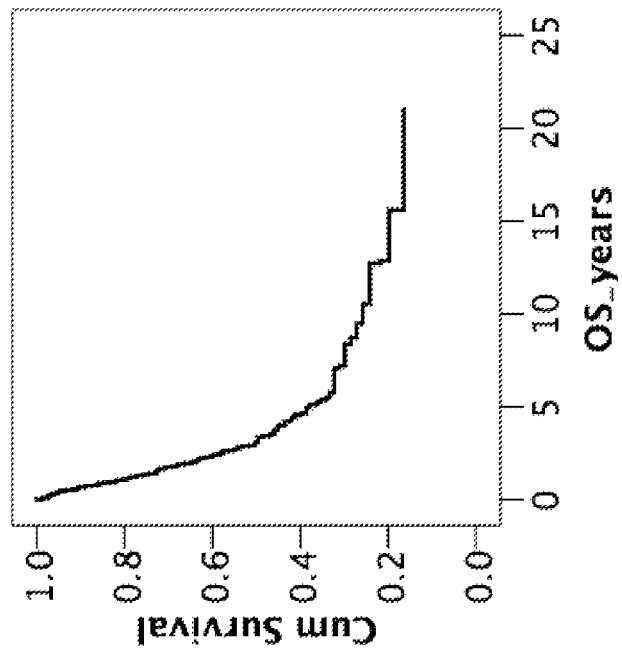
FIG. 1A shows overall survival (OS). Estimated five-year survival is approximately 38% for all patients in this cohort.

As a first aspect of the present disclosure, there is provided a method for determining whether a mammalian subject having a cancer belongs to a first or a second group, wherein subjects of the first group are more responsive to a platinum-based treatment than subjects of the second group, comprising the steps of:

a) evaluating the amount of RBM3 protein or RBM3 mRNA present in at least part of a sample earlier obtained from said subject, and determining a sample value corresponding to said amount;

b) comparing the sample value obtained in step a) with a reference value; and, if said sample value is higher than said reference value, c1) concluding that said subject belongs to said first group; and if said sample value is lower than or equal to said reference value, c2) concluding that said subject belongs to said second group.

The first group differs from the second group in that the subjects of the first group generally are more responsive to platinum-based treatment than the subjects of the second group. That means that subjects of the first group generally have a higher probability of survival if given a platinum-based treatment regimen than subjects of the second group if given the same treatment regimen or that subjects of the first group generally require lower doses to reach a given probability of survival than subjects of the second group. Here, survival may be measured as overall survival, recurrence-free survival or cancer type specific survival.

It is thus determined whether a cancer subject belongs to a first or a second group, wherein subjects of the first group generally are more responsive to platinum-based treatment than subjects of the second group. The division of subjects having a given cancer into the two groups is determined by comparing samples values from the subjects with a reference value. The reference value is thus the determinant for the size of the respective groups; the higher the reference value, the fewer the subjects in the first group and the lower the likelihood that a tested subject belongs to the first group.

For the avoidance of doubt, the first and the second group consist of subjects having the same type of cancer as the tested subject. Ovarian cancer subjects are thus not compared to or grouped with subjects having testicular cancer. Further, the first and the second group may consist of subjects having the same or similar stage and/or subtype of cancer as the tested subject. Also, the groups may consist of subjects having the same or similar age, race, sex, menopausal status, genetic characteristics and/or medical status or history as the tested subject.

The present disclosure is based on the inventors' insight that the expression of RBM3 in a sample obtained from a subject having a cancer may serve as an indicator of the subject's response to platinum-based treatment. The inventors have identified a correlation between values of RBM3 on the one hand and response to platinum-based therapeutic treatment on the other. Typically, high RBM3 values are shown herein to correlate with a relatively high responsiveness to platinum-based treatment.

Platinum-based treatment has proven effective in a range of cancer types. However, the treatment is normally associated with, sometimes severe, side-effects. Therefore, the inventors have concluded that it is beneficial to adapt the doses of the treatment (i.e. the intensity of the treatment) to the responsiveness of the cancer subject such that unnecessary overtreatment is avoided. That is, a highly responsive subject may require a lower dose than a less responsive subject. Further, it is beneficial to identify the subjects who are unlikely to at all respond to the treatment. Such subjects should be treated with alternative regimens.

In conclusion, the above method may assist the physician responsible for the treatment of a cancer subject when deciding whether to apply platinum-based treatment or not and, in cases when platinum-based treatment is found appropriate, the intensity level of the treatment.

If the cancer subject of the above method is found to belong to the first group, the physician's decision may thus be to apply a platinum-based treatment at a relatively low dose. If, however, the cancer subject is found to belong to the second group, the physicians' decision may be to apply the platinum-based treatment at a relatively high dose or to refrain from the platinum-based treatment, possibly in favor of another treatment.

Accordingly, as a second aspect of the present disclosure, there is provided a method for determining the level of intensity of a platinum-based treatment of a mammalian subject having a cancer, comprising the steps of:

a) evaluating the amount of RBM3 protein or RBM3 mRNA present in at least part of a sample earlier obtained from said subject, and determining a sample value corresponding to said amount;

b) comparing the sample value obtained in step a) with a reference value; and, if said sample value is higher than said reference value, c1) concluding that said subject should undergo platinum-based treatment of a first intensity; and if said sample value is lower than or equal to said reference value, c2) concluding that said subject should undergo platinum-based treatment of a second intensity, wherein said second intensity is higher than said first intensity.

The above method of the second aspect may be particularly relevant for subjects having ovarian cancer or testicular cancer, which are almost always treated with platinum-based therapy in many parts of the world today.

The level of intensity may for example be measured as the average daily or weekly dose of a platinum-based therapeutic agent given to the subject. A treatment of the second intensity may thus be applied more frequently or in higher individual doses than a treatment of the first intensity. The treatment of the second intensity may also comprise application of a more aggressive platinum-based therapeutic agent than the treatment of the first intensity. Yet another possibility is that the treatment of the second intensity is applied for a longer period than the treatment of the first intensity.

In an embodiment of the second aspect, c1) may thus be concluding that said subject should undergo platinum-based treatment during a first period and c2) may be concluding that said subject should undergo platinum-based treatment during a second period, wherein the second period is longer than the first period.

As an alternative configuration of the second aspect, there is provided a method for determining whether to refrain from a platinum-based treatment of a mammalian subject having a cancer, comprising the steps of:

a) evaluating the amount of RBM3 protein or RBM3 mRNA present in at least part of a sample earlier obtained from said subject, and determining a sample value corresponding to said amount;

b) comparing the sample value obtained in step a) with a reference value; and, if said sample value is lower than or equal to said reference value, c) refraining from treating the subject with the platinum-based treatment.

This alternative embodiment of the second aspect is particularly relevant for subjects having cancers for which platinum-based treatment is not considered standard, e.g. all cancers but ovarian cancer and testicular cancer.

In any case, RBM3 high cancer subjects are likely to benefit from platinum-based treatment according to teachings of the present disclosure. As a third aspect of the present disclosure, there is thus provided a method of treatment of a mammalian subject having a cancer, comprising the steps of:
 a) evaluating the amount of RBM3 protein or RBM3 mRNA present in at least part of a sample from said subject, and determining a sample value corresponding to said amount;
 b) comparing the sample value obtained in step a) with a reference value; and,
 if said sample value is higher than said reference value,
 c) applying a platinum-based treatment to said subject.

The method of treatment may be limited to the decision-making and treatment. Thus, as a configuration of the third aspect, there is provided a method of treatment of a subject having a cancer, comprising:
 α) comparing a sample value corresponding to a level of RBM3 protein or RBM3 mRNA in a sample from the subject with a reference value;
 and,
 if said sample value is higher than said reference value,
 β) applying a platinum-based treatment to said subject.

Numerous ways of obtaining a sample value corresponding to a level of RBM3 protein or RBM3 mRNA in a sample from a subject are described in the present disclosure, which also provides various examples of (clinically) relevant reference values.

Regarding step a) of the methods of the present disclosure, an increase in the amount of RBM3 protein or RBM3 mRNA typically results in an increase in the sample value, and not the other way around. However, in some embodiments, the evaluated amount may correspond to any of a predetermined number of discrete sample values. In such embodiments, a first amount and a second, increased, amount may correspond to the same sample value. In any case, an increase in the amount of RBM3 protein or RBM3 mRNA will not result in a decrease in the sample value in the context of the present disclosure.

However inconvenient, but in an equivalent fashion, the evaluated amounts may be inversely related to sample values if the qualification between step b) and c) is inverted. For example, the qualification between step b) and c) is inverted if the phrase "if the sample value is higher than the reference value" is replaced with "if the sample value is lower than the reference value".

A physician responsible for the treatment of a cancer subject may take several parameters into account, such as the result of an immunohistochemical evaluation, patient age, hormone receptor status, general condition of the patient, medical history, such as cancer history and hereditary characteristics, e.g. whether there is a history of cancer in the subject's family when deciding on a suitable treatment regimen for the subject. To be guided in the decision, the physician may perform a RBM3 test, or order a RBM3 test performed, according to anyone of the above methods. Further, the physician may assign to someone else, such as a lab worker, to perform step a), and optionally step b), while performing step c), and optionally b), himself.

As a variant of the above methods, there is provided a method for predicting the response of a platinum-based treatment of a mammalian subject having a cancer, comprising the steps of:
 a) evaluating the amount of RBM3 protein or RBM3 mRNA present in at least part of a sample from the subject, and determining a sample value corresponding to the evaluated amount;
 b) correlating the sample value of step a) to a predicted response to the treatment.

In one embodiment, the sample may be an earlier obtained sample.

The correlating of step b) refers to any way of associating survival data to the obtained sample value so as to establish the treatment prediction. With the knowledge of the teachings of the present disclosure, the skilled person may conclude a predicted response without undue burden.

In the context of the methods of the present disclosure, "earlier obtained" refers to obtained before the method is performed. Consequently, if a sample earlier obtained from a subject used in a method, the method does not involve obtaining the sample from the subject, i.e., the sample was previously obtained from the subject in a step separate from the method.

All the methods and uses of the present disclosure, except the methods of treatment, may be carried out entirely in vitro.

Further, in the context of the present disclosure, "a mammalian subject having a cancer" refers to a mammalian subject having a primary or secondary tumor or a mammalian subject which has had such tumor removed, wherein the removal of the tumor refers to killing or removing the tumor by any type of surgery or therapy. In the latter case, the tumor may for example have been removed less than one year ago. For example, a subject who has had a tumor removed by surgery and is about to get adjuvant therapy is considered "having a cancer" in the context of the present disclosure. In the method and use aspects of the present disclosure, "a mammalian subject having a cancer" also includes the case wherein the mammalian subject is suspected of having a cancer at the time of the performance of the use or method and the cancer diagnosis is established later.

Still further, in the context of the present disclosure, the "reference value" refers to a predetermined value which is relevant for making decisions, or drawing conclusions, regarding the treatment or treatment prediction. Guided by the teachings of the present disclosure, the person skilled in the art may select a relevant reference value without undue burden.

Step a) of the methods of the above aspects involve evaluating an amount of RBM3 protein or RBM3 mRNA present in at least part of the sample, and determining a sample value corresponding to the amount. The "at least part of the sample" refers to a relevant part or relevant parts of the sample for establishing a level of responsiveness or drawing conclusions regarding suitable treatments. The person skilled in the art understands which part or parts that are relevant under the circumstances present when performing the method. For example, if evaluating a sample comprising cells, the skilled person may only consider the tumor cells, or only the nuclei or cytoplasms of tumor cells, of the sample.

Further, in step a) an amount is evaluated and a sample value corresponding to the amount is determined. Consequently, an exact measurement of the amount of RBM3 protein or RBM3 mRNA is not required for obtaining the sample value. For example, the amount of RBM3 protein may be evaluated by visual inspection of a prepared and stained tissue sample and the sample value may then be categorized as for example high or low based on the evaluated amount.

The evaluation and determination of step a) requires some kind of processing or manipulation of the sample. It is not possible to determine the sample value by mere inspection. Various techniques, of which some are presented below, for such evaluation and determination, are well known to the skilled person. The methods of the present disclosure are therefore not limited to any specific technique or techniques for the performance of step a).

In Examples below, the level of RBM3 protein or mRNA expression is shown to correlate with survival in ovarian cancer and testicular cancer subjects treated with a platinum-based therapeutic agent. The finding of the differential expression of the RBM3 protein or mRNA and the treatment predictive relevance thereof thus forms the basis of the present disclosure. In addition to ovarian cancer and testicular cancer, the RBM3 protein is differentially expressed in a number of cancer types, as shown in table 2 (Examples, section 7b). Accordingly, the inventors conclude that the finding in ovarian cancer and testicular cancer is likely to extend to other cancer types. In particular, it is notable that the RBM3 protein is shown to be differentially expressed in testicular, ovarian, lung, urothelial, colorectal, cervical, breast and head and neck cancer, which are all cancer types considered suitable for platinum-based treatment today.

Thus, in embodiments of the present disclosure, the cancer is selected from testicular, ovarian, lung, bladder, colorectal, cervical and head and neck cancer (urothelial cancer is a type of bladder cancer).

In some embodiments, the cancer is selected from ovarian cancer and testicular cancer. Subjects having ovarian cancer or testicular cancer are almost always given platinum-based therapy in many parts of the world, and the findings of the present disclosure are thus particularly relevant in these cancer types.

If the cancer of the present disclosure is an ovarian cancer, it may according to one embodiment be a moderately or well differentiated ovarian cancer (see FIGS. 7, 8, 14 and 17), according to another alternative or complementary embodiment an ovarian cancer is in stage 1 or 2 according to the Federation of Gynecology and Obstetrics (FIGO) classification (see FIGS. 9 and 11) and according to yet another alternative or complementary embodiment a serous (see FIGS. 12, 13 and 14) or endometroid (see FIGS. 10, 11 and 17) ovarian cancer.

If the cancer of the present disclosure is a testicular cancer, it may according to one embodiment be a testicular germ-cell cancer and according to an alternative or complementary embodiment non-seminomatous testicular cancer.

If the cancer of the present disclosure is a colorectal cancer, it may according to one embodiment be a colorectal cancer of a relatively advanced stage, such as cancers of Dukes' stage C or D. However, Dukes' stage B cancers may also be relevant since there is a risk of recurrence in cancer of that stage. Thus, RBM3 high Dukes' stage B subjects may be given platinum-based treatment to prevent recurrence.

If the cancer of the present disclosure is a lung cancer, it may according to one embodiment be a small cell or non-small cell lung cancer.

If the cancer of the present disclosure is a breast cancer, it may according to one embodiment be a triple negative breast cancer, i.e. a breast cancer negative for the estrogen receptor, progesterone receptor and the HER2 receptor. Triple negative breast cancer subjects are considered particularly difficult to treat today and there are ongoing clinical trials in which such subjects are treated with the platinum-based agent cisplatin.

A platinum-based treatment comprises application of platinum-based therapeutic agent. Carboplatin including paraplatin, oxaliplatin, satraplatin, picoplatin and cisplatin are some platinum-based therapeutic agents tested or used in the clinic today. Cisplatin, which is employed in Examples below, is widely used in the clinic, e.g. for the treatment of ovarian cancer, small cell lung cancer and testicular cancer. Oxaliplatin is used in the clinic for treatment of colorectal cancer, often in combination with fluorouracil and leucovorin. Carboplatin is also used in the clinic, e.g. for treatment of ovarian, lung and head and neck cancer. In lung cancer, it is often used in combination with gemcitabine.

In embodiments of the present disclosure, the platinum-based treatment may thus be application of an agent selected from carboplatin, oxaliplatin, satraplatin, picoplatin and cisplatin. In embodiments wherein the cancer is ovarian or lung cancer, the agent may for example be cisplatin or carboplatin. In embodiments where the cancer is colorectal cancer, the agent may for example be oxaliplatin. In embodiments where the cancer is testicular cancer, the agent may for example be cisplatin.

In embodiments of the methods of the above aspects, the sample may be a body fluid sample. For example, the body fluid sample may be selected from the group consisting of blood, plasma, serum, cerebral fluid, urine, lymph, seminal fluid and exudate. Alternatively, the sample may be a cytology sample or a stool sample.

The level of RBM3 protein may preferably be measured intracellularly or in cell-derived material. Thus, the body fluid, cytology or stool sample may for example comprise cells, such as tumor cells.

In further embodiments of the methods of the above aspects, the sample may be a tissue sample, such as a tumor sample, e.g. from a previously performed surgical removal of a tumor from the subject.

Further, the inventors have noted that nuclear and/or cytoplasmic expression of RBM3 protein is relevant for determining the level of responsiveness to platinum-based treatment or selecting treatments. For example, both nuclear and cytoplasmic expression of RBM3 protein is found to be relevant in colorectal cancer, ovarian cancer and testicular cancer. Thus, the evaluation of step a) may be limited to the nuclei or cytoplasms of cells, such as tumor cells, of said sample. Consequently, when a tissue sample is examined, only the nuclei or cytoplasms of tumor cells may be taken into consideration. Such examination may for example be aided by immunohistochemical staining.

Figure 15A:
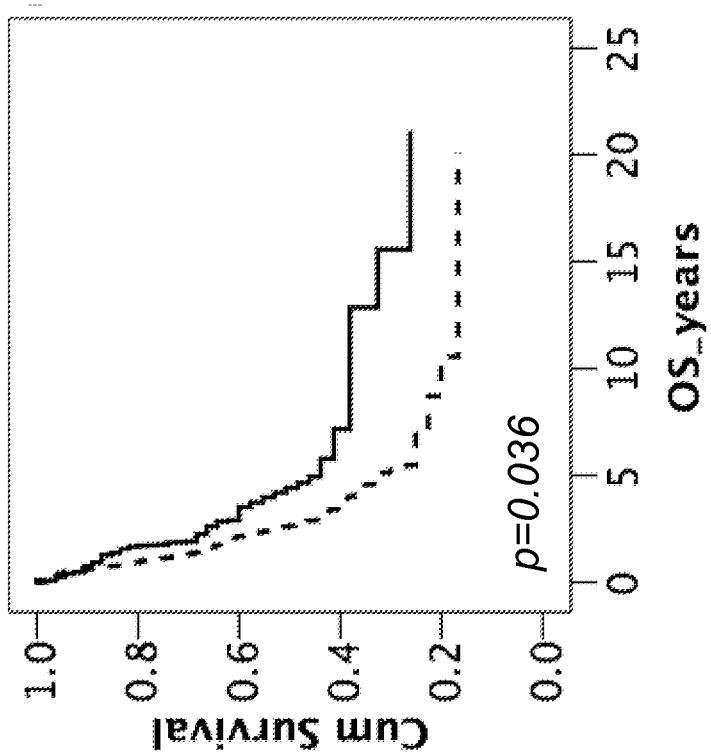
In FIG. 15A all subjects were split into three groups based on staining score (SS) status.
Figure 15B:
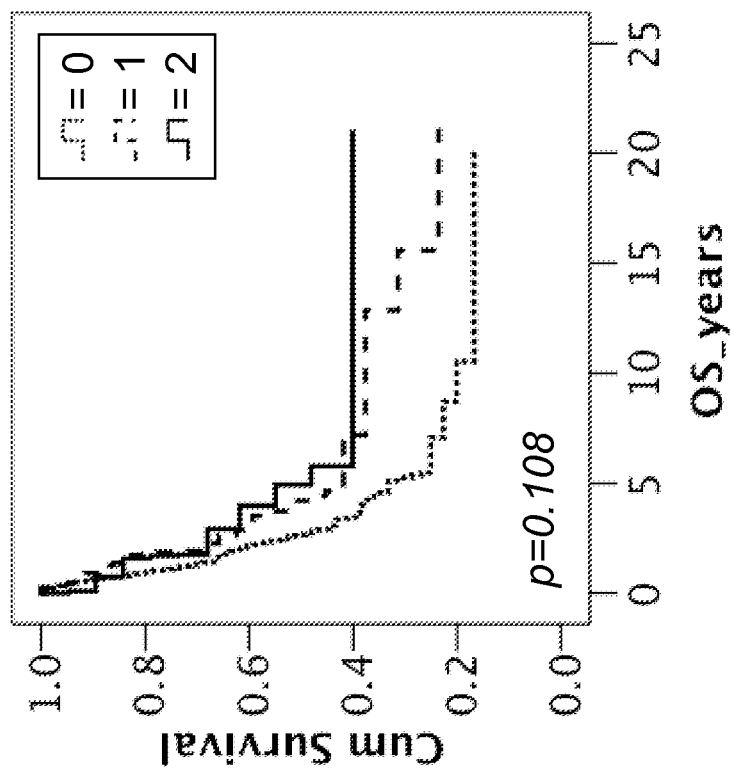
In FIG. 15B RBM3 expression was dichotomized into high and low categories. A solid line represents a high SS of RBM3 expression (SS>0), and a dotted line represents a low SS of RBM3 expression (SS=0).
Figure 17:
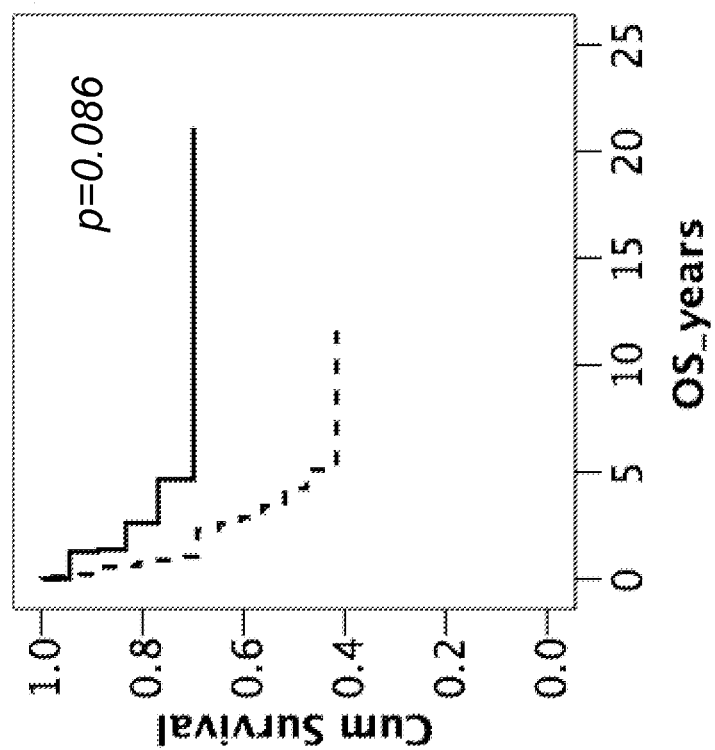
FIG. 17 shows the impact of RBM3 level on OS for patients diagnosed with grade 1 or 2 EOC. All 44 subjects were stained with the 1B5 monoclonal antibody. RBM3 expression was dichotomized into high and low categories. A solid line represents a high SS of RBM2 expression (SS>0), and a dotted line represents a low SS of RBM3 expression (SS=0).

When performing the methods according to the above aspects, it may be convenient to use zero as the reference value, because in such case, it has only to be established in step a) whether RBM3 protein or RBM3 mRNA is present in the sample or not. FIGS. 15*b* and 17 indicate that zero (i.e. no detectable RBM3 protein) is a working cut-off value for establishing two subgroups of different survival.

Thus, in embodiments of the methods of the above aspects, the sample value of step a) may be either 1, corresponding to detectable RBM3 protein or RBM3 mRNA in the sample, or 0, corresponding to no detectable RBM3 protein or RBM3 mRNA in the sample. Consequently, in such embodiments, the evaluation of the sample is digital: RBM3 protein or RBM3 mRNA is considered to be either present or not. In the context of the present disclosure, "no detectable RBM3 protein or RBM3 mRNA" refers to an amount of RBM3 protein or RBM3 mRNA that is so small that it is not, during normal operational circumstances, detectable by a person or an apparatus performing the step a). The "normal operational circumstances" refer to the laboratory methods and techniques a person skilled in the art would find appropriate for performing the methods of the present disclosure.

Accordingly, in embodiments of the methods of the present disclosure, the reference value of step b) may be 0. And it follows that, in further embodiments of the methods of the present disclosure, the reference value of step b) may correspond to a reference sample having no detectable RBM3 protein or RBM3 mRNA (see below).

A sample value of RBM3 protein or RBM3 mRNA being higher than the reference value, or a subject from which such sample value is obtained, is sometimes referred to herein as being "RBM3 high". Further, a sample value of RBM3 protein or RBM3 mRNA being lower than, or equal to, the reference value, or a subject from which such sample value is obtained, is sometimes referred to herein as being "RBM3 low".

In the context of the present disclosure, the terms "sample value" and "reference value" are to be interpreted broadly. The quantification of RBM3 protein or RBM3 mRNA to obtain these values may be done via automatic means, via a scoring system based on visual or microscopic inspection of samples, or via combinations thereof. However, it is also possible for a skilled person, such as a person skilled in the art of histopathology, to determine the sample and reference values by inspection, e.g., of tissue slides that have been prepared and stained for RBM3 protein expression. Determining that the sample value is higher than the reference value may thus correspond to determining, upon visual or microscopic inspection, that a sample tissue slide is more densely stained and/or exhibit a larger fraction of stained cells than a reference tissue slide. The sample value may also be compared to a reference value given by a literal reference, such as a reference value described in wording or by a reference picture. Consequently, the sample and/or reference values may in some cases be mental values that the skilled person determines upon inspection and comparison.

One or more of the steps of the methods of the present disclosure may be implemented in an apparatus. For example, step a) and optionally step b) may be performed in an automatic analysis apparatus, and such apparatus may be based on a platform adapted for immunohistochemical analysis. As an example, one or more tumor tissue sample(s) from the subject in question may be prepared for immunohistochemical analysis manually and then loaded into the automatic analysis apparatus, which gives the sample value of step a) and optionally also performs the comparison with the reference value of step b). The operator performing the analysis, the physician ordering the analysis or the apparatus itself may then draw the conclusion of step c). Consequently, software adapted for drawing the conclusion of step c) may be implemented on the apparatus.

A reference value, found to be relevant for establishing treatment prediction or making treatment decisions regarding cancer subjects, for use as comparison with the sample value from the subject, may be provided in various ways. With the knowledge of the teachings of the present disclosure, the skilled artisan can, without undue burden, provide relevant reference values for performing the methods of the present disclosure.

The person performing the methods of the above aspects may, for example, adapt the reference value to desired information. For example, the reference value may be adapted to yield the most significant information with regard to survival, e.g., the largest separation between the RBM3 high survival curve and the RBM3 low survival curve (see the figures), which corresponds to the largest difference in survival between the first and the second group of the first aspect. Alternatively, the reference value may be selected such that a group of subjects having particularly high responsiveness or particularly low responsiveness is singled out.

In embodiments of the methods of the above aspects, the reference value may correspond to the amount of RBM3 protein or RBM3 mRNA measured in a reference sample comprising tumor cells, such as a reference sample of tumor tissue. The amount of protein expression of the reference sample may preferably be previously established. Consequently, the reference value may be provided by the amount of RBM3 protein or RBM3 mRNA measured in a reference sample comprising cells expressing a predetermined amount of RBM3 protein or RBM3 mRNA.

Further, the reference value may for example be provided by the amount of RBM3 protein or RBM3 mRNA measured in a reference sample comprising cell lines, such as cancer cell lines, expressing a predetermined, or controlled, amount of RBM3 protein or RBM3 mRNA. The person skilled in the art understands how to provide such cell lines, for example guided by the disclosure of Rhodes et al. (2006) *The biomedical scientist*, p 515-520.

However, as discussed further below, the amount of RBM3 protein in the reference sample does not have to directly correspond to the reference value. The reference sample may also provide an amount of RBM3 protein that helps a person performing the method to assess various reference values. For example, the reference sample(s) may help in creating a mental image of the reference value by providing a "positive" reference value and/or a "negative" reference value.

One alternative for the quantification of RBM3 protein expression in a sample, such as the sample earlier obtained from the subject or the reference sample, is the determination of the fraction of cells in the sample that exhibit RBM3 protein expression over a certain level. The fraction may for example be: a "cellular fraction", wherein the RBM3 protein expression of the whole cells is taken into account; a "cytoplasmic fraction", wherein the RBM3 protein expression of only the cytoplasms of the cells is taken into account; or a "nuclear fraction", wherein the RBM3 protein expression of only the nuclei of the cells is taken into account. The nuclear fraction may for example be classified as <2%, 2-25%, >25-75% or >75% immunoreactive cells of the relevant cell population. The "nuclear fraction" corresponds to the percentage of relevant cells in a sample that exhibits a positive staining in the nucleus, wherein a medium or distinct and strong immunoreactivity in the nucleus is considered positive and no or faint immunoreactivity in the nucleus is considered negative. The "cytoplasmic fraction" corresponds to the percentage of relevant cells in a sample that exhibits a positive staining in the cytoplasm, wherein a medium or distinct and strong immunoreactivity in the cytoplasm is considered positive and no or faint immunoreactivity in the cytoplasm is considered negative. The person skilled in the art of pathology understands which cells that are relevant under the conditions present when performing the method and may determine a nuclear or cytoplasmic fraction based on his general knowledge and the teachings of the present disclosure. The relevant cells may for example be tumor cells. Further, the skilled artisan understands how to perform corresponding measurements employing the "cellular fraction".

Another alternative for the quantification of RBM3 protein expression in a sample, such as the sample earlier obtained from the subject or the reference sample, is the determination of the overall staining intensity of the sample. The intensity may for example be: a "cellular intensity", wherein the RBM3 protein expression of the whole cells is taken into account; a "cytoplasmic intensity", wherein the RBM3 protein expression of only the cytoplasms of the cells is taken into account, or a "nuclear intensity", wherein the RBM3 protein expression of only the nuclei of the cells is taken into account. Nuclear intensity is subjectively evaluated in accordance with standards used in clinical histopathological diagnostics. Outcome of a nuclear intensity determination may be classified as: absent=no overall immunoreactivity in the nuclei of relevant cells of the sample, weak=faint overall immunoreactivity in the nuclei of relevant cells of the sample, moderate=medium overall immunoreactivity in the nuclei of relevant cells of the sample, or strong=distinct and strong overall immunoreactivity in the nuclei of relevant cells of the sample. Outcome of a cellular intensity determination may be classified as: absent=no overall immunoreactivity in the cytoplasms of relevant cells of the sample, weak=faint overall immunoreactivity in the cytoplasms of relevant cells of the sample, moderate=medium overall immunoreactivity in the cytoplasms of relevant cells of the sample or strong=distinct and strong overall immunoreactivity in the cytoplasms of relevant cells of the sample. In some embodiments, the weak and moderate values may be combined into a weak/moderate value. The person skilled in the art understands which cells that are relevant under the conditions present when performing the method and may determine a nuclear or cytoplasmic intensity based on his general knowledge and the teachings of the present disclosure. The relevant cells may for example be tumor cells. Further, the skilled artisan understands how to perform corresponding measurements employing the "cellular intensity".

Thus, in embodiments of the methods of the above aspects, the reference value may be a nuclear fraction, a nuclear intensity, a combination of a nuclear fraction and a nuclear intensity, a cytoplasmic fraction, a cytoplasmic intensity or a combination of a nuclear fraction and a nuclear intensity.

As indicated in the figures, more than one reference value based on expression of RBM3 protein may function as a relevant reference value for determining the level of responsiveness.

Thus, in embodiments of the methods of the above aspects, the reference value of step b) is a nuclear or cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Further, in embodiments of the methods of the above aspects the reference value of step b) may be a moderate nuclear or cytoplasmic intensity or lower, such as a weak nuclear or cytoplasmic intensity or lower, such as an absent nuclear or cytoplasmic intensity.

Also, in embodiments of the methods of the above aspects, the reference value may be a combination or a function of a fraction value and an intensity value. The reference value may thus involve two, and even more, criteria. Examples of such combined reference values are given in Table 1 below. In embodiments of the methods of the above aspects, the reference value may thus be a "staining score" (SS) of 2 or lower, such as 1 or lower, such as 0.

In general, the selection of an intensity value and/or a fraction value as the reference value may depend on the staining procedure, e.g., on the type and amount/concentration of the employed antibody and on the type and concentration of the staining reagents.

Guided by the present disclosure, a person skilled in the art, e.g., a pathologist understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of RBM3 protein for establishing the appearance of a certain fraction or intensity.

However, a reference sample may not only be used for the provision of the actual reference value, but also for the provision of an example of a sample with an amount of RBM3 protein that is higher than the amount corresponding to the reference value. As an example, in histochemical staining, such as in immunohistochemical staining, the skilled artisan may use a reference sample for establishing the appearance of a stained sample having a high amount of RBM3 protein, e.g., a positive reference. Subsequently, the skilled artisan may assess the appearances of samples having lower amounts of RBM3 protein, such as the appearance of a sample with an amount of RBM3 protein corresponding to the reference value. In other words, the skilled artisan may use a reference sample to create a mental image of a reference value corresponding to an amount of RBM3 protein which is lower than that of the reference sample. Alternatively, or as a complement, in such assessments, the skilled artisan may use another reference sample having a low amount of RBM3 protein, or lacking detectable RBM3 protein, for establishing the appearance of such sample, e.g., as a "negative reference".

For example, if a moderate nuclear intensity is used as the reference value, two reference samples may be employed: a first reference sample having no detectable RBM3 protein, and thus corresponding to an absent nuclear intensity, which is lower than the reference value; and a second reference sample having an amount of RBM3 protein corresponding to a strong nuclear intensity, which is higher than the reference value.

Consequently, in the evaluation, the skilled artisan may use a reference sample for establishing the appearance of a sample with a high amount of RBM3 protein. Such reference sample may be a sample comprising tissue expressing a high amount of RBM3 protein, such as a sample comprising tumor tissue having a pre-established high expression of RBM3 protein.

Accordingly, the reference sample may provide an example of a strong nuclear intensity (NI). With the knowledge of the appearance of a sample with strong NI, the skilled artisan may then divide samples into the NI categories absent, weak, moderate and strong. This division may be further assisted by a reference sample lacking detectable RBM3 protein (negative reference), i.e., a reference sample providing an absent nuclear intensity. Also, the reference sample may provide an example of a sample with a nuclear fraction (NF) higher than 75%. With the knowledge of the appearance of a sample with more than 75% positive cells, the skilled artisan may then evaluate the NF of other samples having e.g., a lower percentage of positive cells. This division may be further assisted by a reference sample essentially lacking RBM3 protein (negative reference), i.e., a reference sample providing a low NF (e.g., <5%, such as <2%), or a NF of 0. The same applies to cytoplasmic intensity and cytoplasmic fraction.

As mentioned above, cell lines expressing a controlled amount of RBM3 protein may be used as the reference, in particular as a positive reference.

One or more pictures may also be provided as the "reference sample". For example, such a picture may show an example of a tumor tissue slide stained with a certain antibody during certain conditions and exhibiting a certain nuclear or cytoplasmic intensity and/or fraction. The above discussion about the "reference sample" applies mutatis mutandis to pictures.

The cell lines or pictures may also form part of the kit according to the present disclosure (see below).

Further, the skilled person should recognize that the usefulness of the methods according to the above aspects is not limited to the quantification of any particular variant of the RBM3 protein or RBM3 mRNA present in the subject in question, as long as the protein or mRNA is encoded by the relevant gene and presents the relevant pattern of expression.

As a non-limiting example, the RBM3 protein may comprise a sequence selected from:
i) SEQ ID NO:1; and
ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:1.

As another non-limiting example, the RBM3 protein may comprise, or consists of, a sequence selected from:
i) SEQ ID NO:2; and
ii) a sequence which is at least 85% identical to SEQ ID NO:2.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to SEQ ID NO:2.

As another non-limiting example, the RBM3 mRNA of the present disclosure may comprise or consists of
i) a sequence corresponding to SEQ ID NO:3 or
ii) a sequence which is at least 85% identical to thereto.

In some embodiments, sequence ii) above is at least 90% identical, at least 91% identical, at least 92% identical, at least 93% identical, at least 94% identical, at least 95% identical, at least 96% identical, at least 97 identical, at least 98% identical or at least 99% identical to the sequence i).

The term "% identical", as used in the context of the present disclosure, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). The amino acid residues at each position are compared, and the percentage of positions in the query sequence that have identical correspondences in the target sequence is reported as % identical. Also, the target sequence determines the number of positions that are compared. Consequently, in the context of the present disclosure, a query sequence that is shorter than the target sequence can never be 100% identical to the target sequence. For example, a query sequence of 85 amino acids may at the most be 85% identical to a target sequence of 100 amino acids. This corresponds mutatis mutandis nucleic acid sequences.

In some embodiments, step a) of the methods of the above aspects may comprise:
obtaining biological material from the subject, excising or selecting a relevant part of the biological material to obtain said sample and optionally arranging the sample on a solid phase to facilitate the evaluation of step a). Step a) may thus, as an example, comprise obtaining tumor tissue material from the subject, optionally fixating the tissue material in paraffin or formalin, histo-processing the tissue material to obtain a section which constitute said sample and optionally mounting said sample on a transparent slide, such as a glass slide, for microscopy.

In embodiments of the methods of the aspects above, the RBM3 protein may be detected and/or quantified through the application to the sample of a detectable and/or quantifiable affinity ligand, which is capable of selective interaction with the RBM3 protein. The application of the affinity ligand is performed under conditions that enable binding of the affinity ligand to RBM3 protein in the sample.

To concretize, in embodiments of the methods of the aspects above, step a) may comprise:
a1) applying to said sample a quantifiable affinity ligand capable of selective interaction with the RBM3 protein to be evaluated, said application being performed under conditions that enable binding of said affinity ligand to RBM3 protein present in said sample;
a2) removing non-bound affinity ligand; and
a3) quantifying the affinity ligand remaining in association with said sample to evaluate said amount.

"Affinity ligand remaining in association with the sample" refers to affinity ligand which was not removed in step a2), e.g., the affinity ligand bound to the sample. Here, the binding may for example be the interaction between antibody and antigen.

However, in some embodiments, the removal of non-bound affinity ligand according to a2), e.g. the washing, is not always necessary. Thus, in some embodiments of the methods of the aspects above, step a) may comprise:
aI) applying to said sample a quantifiable affinity ligand capable of selective interaction with the RBM3 protein to be evaluated, said application being performed under conditions that enable binding of said affinity ligand to RBM3 protein present in said sample;
aII) quantifying the affinity bound to said sample to evaluate said amount.

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity/selectivity does not necessarily require high affinity. Molecules with low affinity (in the molar range) for its counterpart have been shown to be as selective/specific as molecules with much higher affinity. In the case of the present disclosure, a specific or selective interaction refers to the extent to which a particular method can be used to determine the presence and/or amount of a specific protein, the target protein, under given conditions in the presence of other proteins in a sample of biological origin, such as an prepared tissue sample or fluid sample of a naturally occurring or processed biological fluid. In other words, specificity or selectivity is the capacity to distinguish between related proteins. Specific and selective are sometimes used interchangeably in the present description. For example, the specificity or selectivity of an antibody may be determined as in Examples, Section 2, below, wherein analysis is performed using a protein array set-up, a suspension bead array and a multiplexed competition assay, respectively. Specificity and selectivity determinations are also described in Nilsson P et al. (2005) Proteomics 5:4327-4337.

It is regarded as within the capabilities of those of ordinary skill in the art to select or manufacture the proper affinity ligand and to select the proper format and conditions for detection and/or quantification. Nevertheless, examples of affinity ligands that may prove useful, as well as examples of formats and conditions for detection and/or quantification, are given below for the sake of illustration.

Thus, in embodiments of the present disclosure, the affinity ligand may be selected from the group consisting of antibodies, fragments thereof and derivatives thereof, i.e., affinity ligands based on an immunoglobulin scaffold. The antibodies and the fragments or derivatives thereof may be isolated. Antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. The polyclonal antibodies may be mono-specific. Monoclonal antibodies of defined specificity can be produced using the hybridoma technology developed by Köhler and Milstein (Köhler G and Milstein C (1976) Eur. J. Immunol. 6:511-519). The antibody fragments and derivatives of the present disclosure are capable of selective interaction with the same antigen (e.g. RBM3 protein) as the antibody they are fragments or derivatives of. Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Pluckthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363:446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Pluckthun A (1988) Science 240:1038-1041).

In some embodiments, the affinity ligand of the present disclosure is capable of selective interaction with a peptide consisting of the amino acid sequence SEQ ID NO:1. As described below under Examples, Section 1b, the RBM3 fragment SEQ ID NO:1 was designed to lack transmembrane regions to ensure efficient expression in E. coli, and to lack any signal peptide, since those are cleaved off in the mature protein. SEQ ID NO:1 was thus designed for immunizations. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems. Accordingly, in the cases wherein the affinity ligand is an antibody or fragment derivative thereof, the affinity ligand may be obtainable by a process comprising a step of immunizing an animal with a peptide whose amino acid sequence consists of the sequence SEQ ID NO:1. For example, the immunization process may comprise primary immunization with the protein in Freund's complete adjuvant. Also, the immunization process may further comprise boosting at least two times, in intervals of 2-6 weeks, with the protein in Freund's incomplete adjuvant. Processes for the production of antibodies or fragments or derivatives thereof against a given target are known in the art.

Further, as described below under Examples, Section 4, two epitope regions (SEQ ID NO:4 and SEQ ID NO:5) have been identified within SEQ ID NO:1. The affinity ligand may thus be obtainable by a process comprising a step of immunizing an animal with a peptide whose amino acid sequence consists of SEQ ID NO:4 or SEQ ID NO:5. Also, the antibody or fragment may be obtainable by a process comprising a step of immunizing an animal with an RBM3 fragment which consists of 20 amino acids or less, such as 15 amino acids or less, and comprises a sequence selected from SEQ ID NO:6-19.

For a further discussion about SEQ ID NO:4-19, see below.

In the context of the present disclosure, a "mono-specific antibody" is one or a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present disclosure, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Polyclonal and monoclonal antibodies, as well as their fragments and derivatives, represent the traditional choice of affinity ligands in applications requiring selective biomolecular recognition, such as in the detection and/or quantification of RBM3 protein according to the method aspects above. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific/selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P Å and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against RBM3 protein for use according to the present disclosure, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/

04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269: 22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life. Sci. 59:1993-1998); staphylococcal nuclease (Norman T C et al. (1999) Science 285: 591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Pluckthun A (1997) Proc. Natl. Acad. Sci. U.S.A. 94:4937-4942), yeast two-hybrid system (Fields S and Song 0 (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the present disclosure, the affinity ligand may be a non-immunoglobulin affinity ligand derived from any of the protein scaffolds listed above, or an oligonucleotide molecule.

As mentioned above, the RBM3 protein fragment SEQ ID NO:1 was designed to consist of a unique sequence with low homology with other human proteins and to minimize cross reactivity of generated affinity reagents. Consequently, in embodiments of the present disclosure, the affinity ligand may be capable of selective interaction with a polypeptide consisting of the amino acid sequence SEQ ID NO:1.

As described below under Examples, Section 4, the epitope regions SEQ ID NO:4 and 5 has been identified within SEQ ID NO:1. Thus, in some embodiments, the affinity ligand of the present disclosure is capable of selective interaction with a peptide consisting of an amino acid sequence selected from SEQ ID NO:4 and 5.

Further, as described above under Examples, Section 5, another four epitope regions (SEQ ID NO:6-9) have been identified. Thus, in some embodiments, the affinity ligand of the present disclosure is capable of selective interaction with an RBM3 fragment which consists of 20 amino acids or less, such as 15 amino acids or less, and comprises a sequence selected from SEQ ID NO:6-9.

Also, as described above under Examples, Section 6, another ten epitope regions (SEQ ID NO:10-19) have been identified. Thus, in some embodiments, the affinity ligand of the present disclosure is capable of selective interaction with an RBM3 fragment which consists of 20 amino acids or less, such as 15 amino acids or less, and comprises a sequence selected from SEQ ID NO:10-19.

Figure 22:
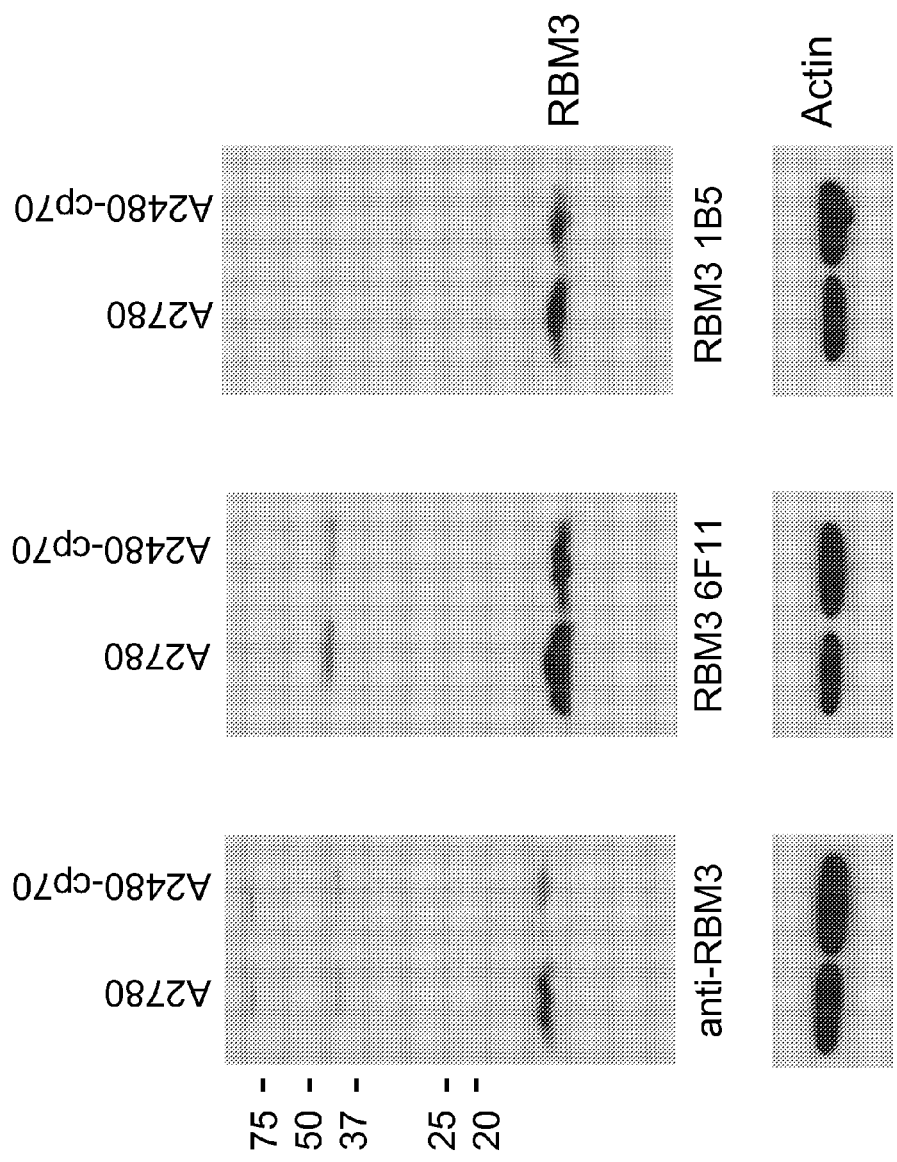
FIG. 22 shows Western blot of RBM3 expression in cisplatin sensitive (A2780) and cisplatin resistant (A2780-cp70) cell lines.

Antibodies having selectivity for a single epitope region (such as monoclonal antibodies) may provide for increased reproducibility in detection analyses as compared to antibodies generated against a longer peptide sequence (such as a PrEST or a full-length protein). The antibodies selective for a single epitope region may also provide for distinct and strong staining in immunohistochemical analyses. These benefits, independently or jointly, may be valuable when and making treatment predictions or decisions regarding treatments according to the present disclosure. In FIG. 22, a benefit (increased selectivity) of monoclonal antibodies according to the present disclosure as compared to a polyclonal antibody is illustrated.

The monoclonal antibodies 6F11 and 1B5 are considered to be particularly beneficial. In FIG. 22, 6F11 and 1B5 are both shown to be more selective than a polyclonal anti-RBM3 antibody. Further, 1B5 is shown to be more selective than 6F11. 1B5 is also employed in Examples, Sections 7, 8 and 10 below.

SEQ ID NO:17, to which 1B5 is shown to bind in Examples, Section 6, is within SEQ ID NO:5. In preferred embodiments of the present disclosure, the affinity ligand is thus capable of selective interaction with an RBM3 fragment which consists of SEQ ID NO:5, and in particularly preferred embodiments of the present disclosure, the affinity ligand is capable of selective interaction with an RBM3 fragment which consists of 20 amino acids or less, such as 15 amino acids or less, and comprises the sequence SEQ ID NO:17.

6F11 is shown to bind to SEQ ID NO:8 and SEQ ID NO:16. In other preferred embodiments of the present disclosure, the affinity ligand is thus capable of selective interaction with an RBM3 fragment which consists of 20 amino acids or less, such as 15 amino acids or less, and comprises a sequence selected from SEQ ID NO:8 and 16. Note that SEQ ID NO:8 and 16 are overlapping and that such a fragment may comprise the sequences of both SEQ ID NO:8 and 16.

The detection and/or quantification of the affinity ligand capable of selective interaction with the RBM3 protein may be accomplished in any way known to the skilled person for detection and/or quantification of binding reagents in assays based on biological interactions. Accordingly, any affinity ligand described above may be used to quantitatively and/or qualitatively detect the presence of the RBM3 protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with RBM3 protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g. $^3H$, $^{14}C$, $^{32}P$, $^{35}S$ or $^{125}I$) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech*. 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects above may be put to use in any of several known formats and set-ups, of which a non-limiting selection is discussed below.

In a set-up based on histology, the detection, localization and/or quantification of a labeled affinity ligand bound to its RBM3 protein target may involve visualizing techniques, such as light microscopy or immunofluoresence microscopy. Other methods may involve the detection via flow cytometry or luminometry.

Biological material from the subject, such as a surgically removed tumor tissue, may be used for obtaining the sample for detection and/or quantification of RBM3 protein or RBM3 mRNA. The sample may thus be an earlier obtained sample. If using an earlier obtained sample in a method, no steps of the method are practiced on the human or animal body.

The affinity ligand may be applied to the sample for detection and/or quantification of the RBM3 protein. This procedure enables not only detection of RBM3 protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from a chemical reaction. Those of skill in the art are aware that a variety of different protocols can be modified in order for proper detection and/or quantification.

In embodiments of the methods of the above aspects, the sample may be immobilized onto a solid phase support or carrier, such as nitrocellulose or any other solid support matrix capable of immobilizing RBM3 protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, primary affinity ligand selective for RBM3 protein may be applied, e.g., as described in Examples, Sections 8, of the present disclosure. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods of the above aspects, the quantifiable affinity ligand of a1) or aI) may be detected using a secondary affinity ligand capable of recognizing the quantifiable affinity ligand. The quantification of a3) or aII) may thus be carried out by means of a secondary affinity ligand with affinity for the quantifiable affinity ligand. As an example, the secondary affinity ligand may be an antibody or a fragment or a derivative thereof.

As an example, one available method for detection and/or quantification of the RBM3 protein is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the RBM3 protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^3H$, $^{14}C$, $^{32}P$, $^{35}S$ or $^{125}I$. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize RBM3 protein by detection of radioactivity in vivo or in vitro. Radionuclear scanning with e.g., gamma camera, magnetic resonance spectroscopy or emission tomography function for detection in vivo and in vitro, while gamma/beta counters, scintillation counters and radiographies are also used in vitro.

Methods for detecting and quantifying biomarkers on the mRNA level are well known within the art.

According to one such method, total cellular RNA is purified from cells by homogenization in the presence of nucleic acid extraction buffer, followed by centrifugation. Nucleic acids is then precipitated, in order to remove DNA by treatment with DNase and precipitation. The RNA molecules are then separated by gel electrophoresis on agarose gels according to standard techniques, and transferred to nitrocellulose filters by, e.g., the so-called "Northern" blotting technique. The RNA is then immobilized on the filters by heating. Detection and quantification of specific RNA is accomplished using appropriately labeled DNA or RNA probes complementary to the RNA in question. See, for example, Molecular Cloning: A Laboratory Manual (Sambrook J. et al., (1989) 2nd edition, Cold Spring Harbor Laboratory Press). Methods for the preparation of labeled DNA and RNA probes, and the conditions for hybridization thereof to target nucleotide sequences, are described in Molecular Cloning: A Laboratory Manual (Sambrook J. et al., (1989) 2nd edition, Cold Spring Harbor Laboratory Press). For example, the nucleic acid probe may be labeled with, e.g., a radionuclide such as $^3H$, $^{32}P$, $^{33}P$, $^{14}C$, or $^{35}S$; a heavy metal; or a ligand capable of functioning as a specific binding pair member for a labeled ligand (e.g., biotin, avidin, or an antibody), a fluorescent molecule, a chemi luminescent molecule, an enzyme, or the like.

Probes may be labeled to high specific activity by either the nick translation method (Rigby et al., (1977) J. Mol. Biol, 113: 237-251), or by the random priming method (Fienberg, (1983) Anal. Biochem., 132: 6-13). The latter can be a method for synthesizing $^{32}P$-labeled probes of high specific activity from RNA templates. For example, by replacing preexisting nucleotides with highly radioactive nucleotides according to the nick translation method, it is possible to prepare $^{32}P$—labeled nucleic acid probes with a specific activity well in excess of 10 cpm/microgram. Autoradiographic detection of hybridization then can be performed by exposing hybridized filters to photographic film. Densitometric scanning of the photographic films exposed by the hybridized filters provides an accurate measurement of biomarker levels. Using another approach, biomarker levels can be quantified by computerized imaging systems, such as the Molecular Dynamics 400-B 2D Phosphorimager (Amersham Biosciences, Piscataway, N.J., USA).

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA blotting hybridization techniques, determining the levels of RNA transcript may be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects.

The relative number of RNA transcripts in cells also can be determined by reverse transcription of RNA transcripts, followed by amplification of the reverse-transcribed transcripts by polymerase chain reaction (RT-PCR). The levels of RNA transcripts can be quantified in comparison with an internal standard, for example, the level of mRNA from a standard gene present in the same sample. The person skilled in the art is capable of selecting suitable genes for use as an internal standard. The methods for quantitative RT-PCR and variations thereof are within the skill in the art.

Any suitable primers can be used for the quantitative RT-PCR. Preferably, the primers are specific to RBM3. It is within the skill in the art to generate primers specific to RBM3 (e.g. starting from SEQ ID NO:3). Primers can be of any suitable length, but are preferably between 19 and 23 (e.g., 19, 20, 21, 22, or 23) nucleotides. Ideally, amplicon length should be 50 to 150 (up to 250 may be necessary but then optimization of the thermal cycling protocol and reaction components may be necessary) bases for optimal PCR efficiency. Designing primers that generate a very long amplicon may lead to poor amplification efficiency. Information about primer design and optimal amplicon size may for example be found at www.ambion.com.

In some instances, it may be desirable to use microchip technology to detect biomarker expression. The microchip can be fabricated by techniques known in the art. For example, probe oligonucleotides of an appropriate length, e.g., 40 nucleotides, are 5'-amine modified at position C6 and printed using commercially available microarray systems, e.g., the GENEMACHINE OmniGrid 100 Microarrayer and Amersham CODELINK activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6 times SSPE/30% formamide at 25° C. for 18 hours, followed by washing in 0.75 times TNT at 37° C. for 40 minutes. At positions on the array, where the immobilized probe DNA recognizes a complementary target cDNA in the sample, hybridization occurs. The labeled target cDNA marks the exact position on the array where binding occurs, thereby allowing automatic detection and quantification. The output consists of a list of hybridization events, which indicate the relative abundance of specific cDNA sequences, and therefore the relative abundance of the corresponding complementary biomarker, in the subject sample. According to one embodiment, the labeled cDNA oligomer is a biotin-labeled cDNA prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding biomarker in the subject sample.

The use of the array has one or more advantages for mRNA expression detection. First, the global expression of several to thousands of genes can be identified in a single sample at one time. Second, through careful design of the oligonucleotide probes, the expression of both mature and precursor molecules can be identified. Third, in comparison with Northern blot analysis, the chip requires a small amount of RNA.

As a fourth aspect of the present disclosure, there is provided a kit for carrying out a method according to the above aspects, which comprises:

a) a quantifiable affinity ligand capable of selective interaction with an RBM3 protein; and b) reagents necessary for quantifying the amount of said quantifiable affinity ligand.

Various components of the kit according to the fourth spect may be selected and specified as described above in connection with the method aspects of the present disclosure.

Thus, the kit according to the present disclosure comprises an affinity ligand against an RBM3 protein, as well as other means that help to quantify the specific and/or selective affinity ligand after it has bound specifically and/or selectively to the RBM3 protein. For example, the kit may contain a secondary affinity ligand for detecting and/or quantifying a complex formed by the RBM3 protein and the affinity ligand capable of selective interaction with the RBM3 protein. The kit may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

In embodiments of the kit aspect, the affinity ligand may be any one of the affinity ligands described above in connection with the method aspects.

Further, in accordance with what is described above in connection with the method aspects, the detectable affinity ligand may in embodiments of the kit aspect comprise a label selected from the group consisting of fluorescent dyes and metals, chromophoric dyes, chemiluminescent compounds and bioluminescent proteins, enzymes, radioisotopes, particles and quantum dots. Alternatively, the reagents necessary for quantifying the amount of the affinity ligand comprise a secondary affinity ligand capable of recognizing the quantifiable affinity ligand. As an example, the secondary affinity ligand capable of recognizing the quantifiable affinity ligand comprises a label selected from the group consisting of fluorescent dyes or metals, chromophoric dyes, chemiluminescent compounds and bioluminescent proteins, enzymes, radioisotopes, particles and quantum dots.

The kit according to the kit aspect may also advantageously comprise a reference sample for provision of, or yielding, the reference value to be used for comparison with the sample value. For example, the reference sample may comprise a predetermined amount of RBM3 protein. Such a reference sample may for example be constituted by a tissue sample containing the predetermined amount of RBM3 protein. The tissue reference sample may then be used by the person of skill in the art in the determination of the RBM3 expression status in the sample being studied, by manual, such as ocular, or automated comparison of expression levels in the reference tissue sample and the subject sample. As another example, the reference sample may comprise cell lines, such as cancer cell lines, expressing a predetermined, or controlled, amount of RBM3 protein. The person skilled in the art understands how to provide such cell lines, for example guided by the disclosure of Rhodes et al. (2006) The biomedical scientist, p 515-520. As an example, the cell lines may be formalin fixed. Also, such formalin fixed cell lines may be paraffin embedded.

The wording "reference sample for provision of the reference value" is to be interpreted broadly in the context of the present disclosure. The reference sample may comprise an amount of RBM3 protein actually corresponding to the reference value, but it may also comprise an amount of RBM3 protein corresponding to a value being higher than the reference value. In the latter case, the "high" value may be used by a person performing the method as an upper reference (positive reference) for assessing, e.g., the appearance of, a reference value which is lower than the "high" value. The person skilled in the art of immunohistochemistry understands how to do such an assessment. Further, as an alternative or a complementing example, the skilled person may use another reference sample comprising a low amount of RBM3 protein for provision of a "low" value in such an assessment, e.g., as a negative reference. This is further discussed above in connection with the method aspects.

Consequently, in embodiments of the kit aspect, the reference sample may comprise an amount of RBM3 protein corresponding to the reference value. As an example, the reference sample may comprise an amount of RBM3 protein corresponding to a nuclear or cytoplasmic fraction of 95% or lower, such as 90% or lower, such as 85% or lower, such as 80% or lower, such as 75% or lower, such as 70% or lower, such as 65% or lower, such as 60% or lower, such as 55% or lower, such as 50% or lower, such as 45% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Alternatively, or as a complement, the reference sample may comprise an amount of RBM3 protein corresponding to a moderate nuclear or cytoplasmic intensity or lower, such as a weak nuclear or cytoplasmic intensity or lower, such as an absent nuclear or cytoplasmic intensity.

The provision of fraction values and intensity values is discussed above in connection with the method aspects.

Further, in alternative or complementing embodiments of the kit aspect, the kit may comprise a reference sample comprising an amount of RBM3 protein corresponding to a value being higher than the reference value. In these embodiments, the reference sample may for example comprise an amount of RBM3 protein corresponding to a nuclear or cytoplasmic fraction of 75% or higher and/or a strong nuclear or cytoplasmic intensity.

In yet further alternative or complementing embodiments of the kit aspect, the kit may comprise a reference sample comprising an amount of RBM3 protein corresponding to a value being lower than or equal to the reference value, e.g., an absent nuclear or cytoplasmic intensity and/or a nuclear or cytoplasmic fraction of <2%, such as 0%.

The kit may thus comprise: a reference sample comprising an amount of RBM3 protein corresponding to a predetermined reference value; a reference sample comprising an amount of RBM3 protein corresponding to a value being higher than a predetermined reference value; and/or a reference sample comprising an amount of RBM3 protein corresponding to a value being lower than or equal to a predetermined reference value.

Consequently, embodiments of the kit may comprise: a first reference sample comprising an amount of RBM3 protein being higher than a predetermined reference value; and a second reference sample comprising an amount of RBM3 protein being lower than or equal to the predetermined reference value.

In embodiments of the kit aspect, the reference sample may be a tissue sample, such as a tissue sample adapted to ocular or microscopic evaluation. As an example, the tissue reference sample may be fixated in paraffin or buffered formalin and/or histo-processed to sections (e.g., µm-thin sections) that are mounted on microscopic glass-slides. The tissue reference sample may be further adapted to staining with affinity ligands, such as antibodies, against an RBM3 protein.

Consequently, in embodiments of the kit aspect, the reference sample may be adapted to directly, or indirectly, provide any relevant reference value, such as any one of the reference values discussed above.

Further embodiments of the reference sample of the kit aspect are discussed above in connection with the reference values and reference samples of the method aspects.

Following the findings presented above, the inventors have realized several uses for the RBM3 protein and fragments thereof.

Thus, as a fifth aspect of the present disclosure, there is provided an RBM3 protein fragment which consists of 50 amino acids or less and comprises a sequence selected from SEQ ID NO:4-19.

In embodiments of the fifth aspect, the fragment consists of 29 amino acids or less.

In further embodiments of the fifth aspect, the fragment consists of 20 amino acids or less, such as 15 amino acids or less, and comprises a sequence selected from SEQ ID NO:6-19.

Possible uses of such fragments are described below.

As a first configuration of a sixth aspect of the present disclosure, there is provided a use of an RBM3 protein, a fragment thereof or an RBM3 mRNA molecule as a treatment predictive marker for platinum-based treatment of a mammalian subject having a cancer.

The use of the first configuration may be entirely in vitro, e.g., on previously obtained samples.

In the context of the present disclosure, "treatment predictive marker" refers to something material which presence indicates a level of responsiveness to a treatment. The marker may thus be a biomarker, such as a human protein. It is to be understood that the presence of the treatment predictive marker, or a relatively high level thereof, is indicative of a relatively high responsiveness to the treatment, while the absence of the treatment predictive marker, or a relatively low level thereof, is indicative of a relatively low responsiveness to the treatment. Here, the "relatively high responsiveness" is high in comparison with the "relatively low responsiveness".

As a second configuration of the sixth aspect, there is provided a use of an RBM3 protein or an antigenically active fragment thereof for the production, selection or purification of a treatment predictive agent for platinum-based treatment of a mammalian subject having a cancer.

The selection and purification may be in vitro, while the production may be in vivo.

An "antigenically active fragment" refers to a fragment of sufficient size to be capable of generating an affinity ligand capable of selective interaction with the fragment.

In the context of the present disclosure, "treatment predictive agent" refers to an agent having at least one property being valuable in an establishment of a treatment prediction. For example, the treatment predictive agent may be capable of selective interaction with the treatment predictive marker.

The treatment predictive agent may be an affinity ligand capable of selective interaction with the RBM3 protein or the antigenically active fragment thereof. Examples of such affinity ligands are discussed above in connection with the method aspects.

Guided by the teachings of the present disclosure, the person skilled in the art understands how to use the RBM3 protein or fragment in the production, selection or purification of the treatment predictive agent. For example, the use may comprise affinity purification on a solid support onto which the RBM3 protein or fragment thereof has been immobilized. The solid support may for example be arranged in a column. Further, the use may comprise selection of affinity ligands having specificity for the RBM3 protein or fragment thereof using a solid support onto which the RBM3 protein or fragment thereof has been immobilized. Such solid support may be well plates (such as 96 well plates), magnetic beads, agarose beads or sepharose beads. Further, the use may comprise analysis of affinity ligands on a soluble matrix, for example using a dextran matrix, or use in a surface plasmon resonance instrument, such as a Biacore™ instrument, wherein the analysis may for example comprise monitoring the affinity of a number of potential affinity ligands for the immobilized RBM3 protein or fragment thereof.

Also, for the production of the treatment predictive agent, the RBM3 protein or an antigenically active fragment thereof may be used in an immunization of an animal, such as a rabbit or mouse.

Such use may be involved in a method comprising the steps:
  i) immunizing an animal using the RBM3 protein or antigenically an active fragment thereof as the antigen;
  ii) obtaining serum comprising the treatment predictive agent from the immunized animal; and, optionally,
  iii) isolating the treatment predictive agent from the serum.
Alternatively the steps following the first step may be:
  ii') obtaining cells from the immunized animal, which cells comprise DNA encoding the treatment predictive agent,
  iii') fusing the cells with myeloma cells to obtain at least one clone, and
  iv') obtaining the treatment predictive agent expressed by the clone.

In embodiments of the sixth aspect, the amino acid sequence of the RBM3 protein may comprise a sequence selected from:
  i) SEQ ID NO:1; and
  ii) a sequence which is at least 85% identical to SEQ ID NO:1.

In some embodiments, sequence ii) is at least 90% identical, at least 91% identical, at least 92% identical, at least 93% identical, at least 94 identical, at least 95% identical, at least 96% identical, at least 97 identical, at least 98% identical or at least 99% identical to SEQ ID NO:1.

Further, in embodiments of the sixth aspect the amino acid sequence of the RBM3 protein may comprise or consist of a sequence selected from:
  i) SEQ ID NO:2; and
  ii) a sequence which is at least 85% identical to SEQ ID NO:2.

In some embodiments, sequence ii) is at least 90% identical, at least 91% identical, at least 92% identical, at least 93% identical, at least 94 identical, at least 95% identical, at least 96% identical, at least 97 identical, at least 98% identical or at least 99% identical to SEQ ID NO:2.

The antigenically active fragment of the sixth aspect may for example be any one of the fragments of the fifth aspect.

As a seventh aspect of the present disclosure, there is provided an affinity ligand capable of selective interaction with an RBM3 protein.

Different embodiments of such an affinity ligand are discussed above in connection with the method aspects.

As an eighth aspect of the present disclosure, there is provided a use of an affinity ligand according to the seventh aspect as a treatment predictive agent for platinum-based treatment of a mammalian subject having a cancer.

Similarly, there is provided a use of an affinity ligand capable of selective interaction with an RBM3 protein for indicating whether a mammalian subject having a cancer should be given a platinum-based treatment.

Here, "should be given a platinum-based treatment" refers to the case where the benefits of the treatment compensate for the disadvantages of the same. The benefits of the treatment refers to a higher probability of survival or recovery if undergoing the treatment than if not undergoing the treatment. The disadvantages of the treatment refer to the drawbacks, such as side-effects, pain or other inconveniences and costs.

Such uses may for example be performed in vitro, e.g., involving the determination of the amount of RBM3 in at least part of a sample earlier obtained from the subject.

In an equivalent manner, there is provided a use of an affinity ligand capable of selective interaction with an RBM3 protein in the manufacture of a treatment predictive agent for platinum-based treatment of a mammalian subject having a cancer.

In the present disclosure, platinum-based treatment is shown to be particularly beneficial for those subjects who are RBM3 protein high or RBM3 mRNA high. The cancer subjects who are RBM3 protein high or RBM3 mRNA high are a previously unrecognized subgroup in the context of platinum-based treatment.

Thus, as a ninth aspect of the present disclosure, there is provided a platinum-based therapeutic agent for use in treatment of a mammalian subject having a cancer, wherein said subject is RBM3 protein high or RBM3 mRNA high.

As a tenth aspect of the present disclosure, there is provided a use of a platinum-based therapeutic agent in the manufacture of a medicament for treatment of a mammalian subject having a cancer, wherein said subject is RBM3 protein high or RBM3 mRNA high.

The subject is "RBM3 protein high" or "RBM3 mRNA high" if any RBM3 protein or mRNA parameter derived from said subject indicates a relatively high responsiveness to platinum-based treatment. For example, the subject may be considered RBM3 protein or RBM3 mRNA high if a relevant biological sample from the subject has been found to contain an amount of RBM3 protein or RBM3 mRNA corresponding to a sample value being higher than a relevant reference value. Relevant sample and reference values are discussed above in connection with the method aspects. Thus, the cancer subject may for example be considered RBM3 protein positive if a relevant sample, such as a tissue sample from a tumor, shows detectable RBM3 protein expression in relevant parts of the sample, such in the tumor cells. Further, the cancer subject may for example be considered RBM3 protein high if such sample contains an amount of RBM3 protein corresponding to a cytoplasmic or nuclear intensity which is higher than absent or a cytoplasmic or nuclear fraction which is higher than 1%. From the present disclosure, the person skilled in the art, such as a pathologist, understands how to determine whether the subject is RBM3 protein high or not and whether the subject is RBM3 mRNA high or not.

Various embodiments of the ninth and tenth aspects, in particular with regard to the type of cancer and the type of platinum-based therapeutic agent, are discussed above in connection with the method aspects.

In general, the inventors believe that the RBM3 protein expression is more relevant than the RBM3 mRNA expression in the context of the present disclosure.

EXAMPLES

Mono-Specific Polyclonal Antibodies

1. Generation of Antigen
a) Materials and Methods

A suitable fragment of the target protein encoded by the EnsEMBL Gene ID ENSG00000102317 was selected using bioinformatic tools with the human genome sequence as template (Lindskog M et al (2005) Biotechniques 38:723-727, EnsEMBL, www.ensembl.org). The fragment was used as template for the production of a 134 amino acid long fragment corresponding to amino acids 18-151 (SEQ ID NO:1) of the RBM3 protein (SEQ ID NO:2; EnsEMBL entry no. ENSP00000365946).

A fragment of the RBM3 gene transcript containing nucleotides 281-682, of EnsEMBL entry number ENST00000376755 (SEQ ID NO:3), was isolated by a Superscript™ One-Step RT-PCR amplification kit with Platinum® Taq (Invitrogen) and a human total RNA pool panel as template (Human Total RNA, BD Biosciences Clontech). Flanking restriction sites NotI and AscI were introduced into the fragment through the PCR amplification primers, to allow in-frame cloning into the expression vector (forward primer: GACGAGCAGGCACTGGAAG (SEQ ID NO:20), reverse primer: GTAATTTCCTCCTGAGTAGC (SEQ ID NO:21). Then, the downstream primer was biotinylated to allow solid-phase cloning as previously described, and the resulting biotinylated PCR product was immobilized onto Dynabeads M280 Streptavidin (Dynal Biotech) (Larsson M et al (2000) J. Biotechnol. 80:143-157). The fragment was released from the solid support by NotI-AscI digestion (New England Biolabs), ligated into the pAff8c vector (Larsson M et al, supra) in frame with a dual affinity tag consisting of a hexahistidyl tag for immobilized metal ion chromatography (IMAC) purification and an immunopotentiating albumin binding protein (ABP) from streptococcal protein G (Sjolander A et al (1997) J. Immunol. Methods 201:115-123; Stahl S et al (1999) Encyclopedia of Bioprocess Technology: Fermentation, Biocatalysis and Bioseparation (Fleckinger M C and Drew S W, eds) John Wiley and Sons Inc., New York, pp 49-63), and transformed into E. coli BL21(DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations.

BL21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM (3-mercaptoethanol; pH=8.0) and incubated for 2 hours at 37° C. and 150 rpm. After centrifugation at 35300 g, the supernatant containing the denatured and solubilized protein was collected.

The $His_6$-tagged fusion protein was purified by immobilized metal ion affinity chromatography (IMAC) on columns with 1 ml Talon® metal ($Co^{2+}$) affinity resin (BD Biosciences Clontech) using an automated protein purification procedure (Steen J et al (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2). Clarified cell lysates were then added to the column. Thereafter, the resin was washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 µl. The 700 µl fraction, containing the antigen, and the pooled 500 and 1300 µl fractions were stored for further use.

The antigen fraction was diluted to a final concentration of 1 M urea with phosphate buffered saline (PBS; 1.9 mM $NaH_2PO_4$, 8.1 mM $Na_2HPO_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).

b) Results

A gene fragment corresponding to nucleotides 281-682 of the full-lengths transcript of RBM3 (SEQ ID NO:3) was successfully isolated by RT-PCR from a human RNA pool using primers specific. The fragment codes for amino acids 18 to 151 of the target protein RBM3 (SEQ ID NO:2). The 134 amino acid fragment (SEQ ID NO:1) of the target protein (SEQ ID NO:2) was designed to lack transmembrane regions to ensure efficient expression in *E. coli*, and to lack any signal peptide, since those are cleaved off in the mature protein. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems.

A clone encoding the correct amino acid sequence was identified, and, upon expression in *E. coli*, a single protein of the correct size was produced and subsequently purified using immobilized metal ion chromatography. After dilution of the eluted sample to a final concentration of 1 M urea and concentration of the sample to 1 ml, the concentration of the protein fragment was determined to be 10.4 mg/ml and was 96.0% pure according to purity analysis.

2. Generation of Antibodies a) Materials and Methods

The purified RBM3 fragment as obtained above was used as antigen to immunize a rabbit in accordance with the national guidelines (Swedish permit no. A 84-02). The rabbit was immunized intramuscularly with 200 µg of antigen in Freund's complete adjuvant as the primary immunization, and boosted three times in four week intervals with 100 µg antigen in Freund's incomplete adjuvant.

Antiserum from the immunized animal was purified by a three-step immunoaffinity based protocol (Agaton C et al (2004) J. Chromatogr. A 1043:33-40; Nilsson P et al (2005) Proteomics 5:4327-4337). In the first step, 7 ml of total antiserum was buffered with 10×PBS to a final concentration of 1×PBS (1.9 mM $NaH_2PO_4$, 8.1 mM $Na_2HPO_4$, 154 mM NaCl), filtered using a 0.45 µm pore-size filter (Acrodisc®, Life Science) and applied to an affinity column containing 5 ml N-hydroxysuccinimide-activated Sepharose™ 4 Fast Flow (GE Healthcare) coupled to the dual affinity tag protein $His_6$-ABP (a hexahistidyl tag and an albumin binding protein tag) expressed from the pAff8c vector and purified in the same way as described above for the antigen protein fragment. In the second step, the flow-through, depleted of antibodies against the dual affinity tag $His_6$-ABP, was loaded at a flow rate of 0.5 ml/min on a 1 ml Hi-Trap NHS-activated HP column (GE Healthcare) coupled with the RBM3 protein fragment used as antigen for immunization (SEQ ID NO:1). The $His_6$-ABP protein and the protein fragment antigen were coupled to the NHS activated matrix as recommended by the manufacturer. Unbound material was washed away with 1×PBST (1×PBS, 0.1% Tween20, pH 7.25), and captured antibodies were eluted using a low pH glycine buffer (0.2 M glycine, 1 mM EGTA, pH 2.5). The eluted antibody fraction was collected automatically, and loaded onto two 5 ml HiTrap™ desalting columns (GE Healthcare) connected in series for efficient buffer exchange in the third step. The second and third purification steps were run on the ÄKTAxpress™ platform (GE Healthcare). The antigen selective (mono-specific) antibodies (msAbs) were eluted with PBS buffer, supplemented with glycerol and $NaN_3$ to final concentrations of 40% and 0.02%, respectively, for long term storage at −20° C. (Nilsson P et al (2005) Proteomics 5:4327-4337).

The specificity and selectivity of the affinity purified antibody fraction were analyzed by binding analysis against the antigen itself and against 94 other human protein fragments in a protein array set-up (Nilsson P et al (2005) Proteomics 5:4327-4337). The protein fragments were diluted to 40 µg/ml in 0.1 M urea and 1×PBS (pH 7.4) and 50 µl of each were transferred to the wells of a 96-well spotting plate. The protein fragments were spotted in duplicate and immobilized onto epoxy slides (SuperEpoxy, TeleChem) using a pin-and-ring arrayer (Affymetrix 427). The slide was washed in 1×PBS (5 min) and the surface was then blocked (Super-Block®, Pierce) for 30 minutes. An adhesive 16-well silicone mask (Schleicher & Schuell) was applied to the glass before the mono-specific antibodies were added (diluted 1:2000 in 1×PBST to appr. 50 ng/ml) and incubated on a shaker for 60 min. Affinity tag-specific IgY antibodies were co-incubated with the mono-specific antibodies in order to quantify the amount of protein in each spot. The slide was washed with 1×PBST and 1×PBS twice for 10 min each. Secondary antibodies (goat anti-rabbit antibody conjugated with Alexa 647 and goat anti-chicken antibody conjugated with Alexa 555, Molecular Probes) were diluted 1:60000 to 30 ng/ml in 1×PBST and incubated for 60 min. After the same washing procedure, as for the first incubation, the slide was spun dry and scanned (G2565BA array scanner, Agilent), thereafter images were quantified using image analysis software (Gene-Pix 5.1, Axon Instruments).

In addition, the specificity and selectivity of the affinity-purified antibody were analyzed by Western blot. Western blot was performed by separation of total protein extracts from selected human cell lines on pre-cast 10-20% SDS-PAGE gradient gels (Bio-Rad Laboratories) under reducing conditions, followed by electro-transfer to PVDF membranes (Bio-Rad Laboratories) according to the manufacturer's recommendations. The membranes were blocked (5% dry milk, 1×TBST; 0.1 M Tris-HCl, 0.5 M NaCl, 0.1% Tween20) for 1 h at room temperature, incubated with the primary affinity purified antibody (diluted 1:500 in blocking buffer) and washed in TBST. The secondary HRP-conjugated antibody (swine anti-rabbit immunoglobulin/HRP, DakoCytomation) was diluted 1:3000 in blocking buffer and chemiluminescence detection was carried out using a Chemidoc™ CCD camera (Bio-Rad Laboratories) and SuperSignal® West Dura Extended Duration substrate (Pierce), according to the manufacturer's protocol.

b) Results

The quality of polyclonal antibody preparations has proven to be dependent on the degree of stringency in the antibody purifications, and it has previously been shown that depletion of antibodies directed against epitopes not originated from the target protein is necessary to avoid cross-reactivity to other proteins and background binding (Agaton C et al (2004) J. Chromatogr. A 1043:33-40). Thus, a protein microarray analysis was performed to ensure that mono-specific polyclonal antibodies of high specificity had been generated by depletion of antibodies directed against the $His_6$-tag as well as of antibodies against the ABP-tag.

To quantify the amount of protein in each spot of the protein array, a two-color dye labeling system was used, with a combination of primary and secondary antibodies. Tag-specific IgY antibodies generated in hen were detected with a secondary goat anti-hen antibody labeled with Alexa 555 fluorescent dye. The specific binding of the rabbit msAb to its antigen on the array was detected with a fluorescently Alexa 647 labeled goat anti-rabbit antibody. Each protein fragment was spotted in duplicates. The protein array analysis shows that the affinity purified mono-specific antibody against RBM3 is highly selective to the correct protein fragment and has a very low background to all other protein fragments analyzed on the array.

The result of the Western blot analysis shows that the antibody specifically detects a single band of approximately 16 kDa in two breast tumor cell lines, T47D and MCF-7. The theoretical molecular weight of RBM3 is 16 kDa (as calculated from the RBM3 amino acid sequence SEQ ID NO:2), corresponding well to the result obtained.

Monoclonal Antibodies

3. Generation of Monoclonal Antibodies a) Materials and Methods

The purified fragment (SEQ ID NO:1) obtained in Section 1 was used as antigen for production of monoclonal antibodies. Antigen was sent to AbSea Biotechnology Ltd (Beijing, China) and briefly, the antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:1) were identified and delivered to Atlas Antibodies AB for further characterization. Cell lines that showed positive results in ELISA, Western blot (WB) and immunohistochemistry (IHC) were selected for subcloning, performed by AbSea Biotechnology Ltd.

In addition, the immunohistochemical staining patterns of the monoclonal antibodies were compared to that of the polyclonal anti-RBM3 antibody generated in Section 2. This polyclonal antibody is sometimes referred to herein as "anti-RBM3".

b) Results

Cell-lines were screened by ELISA (at AbSea) to identify lines that produce monoclonal antibodies (mAbs) that recognize the antigen (SEQ ID NO:1), but not the affinity tag His-ABP. Eight cell-lines showed specific binding to the antigen SEQ ID NO:1 in ELISA and were selected for further testing. For each of the selected eight clones 150-300 µl supernatant was collected, azide was added, and the supernatants were delivered to Atlas Antibodies AB on wet ice. The supernatants were stored at +4° C. upon arrival according to the instructions from AbSea. Further testing of the cell lines resulted in the identification of three interesting cell lines, clones 1B5, 6F11 and 7G3 that gave positive results in both Western blot and IHC analysis. These clones were selected for subcloning and expansion, performed by AbSea Biotechnology Ltd.

Epitope Mapping

4. Epitope Mapping Using Bacterial Display I

RBM3 DNA corresponding to SEQ ID NO:1 (i.e. aa 18-151 of ENSP00000365946 or by 261-682 ENST00000376755) was amplified by PCR using vector pAff8c as template. The amplified DNA was fragmentized to various lengths (approximately 50-150 bp) by sonication, followed by ligation into the staphylococcal display vector (pSCEM2) and transformed into S. Carnosus yielding around 100000 transformants. In-frame DNA fragments were displayed as peptides on the staphylococcal surface. After incubation with antibody (selective for SEQ ID NO:1, obtained as in Section 2 above) and fluorescently labeled secondary reagents, positive and negative cells were separately sorted using flow cytometry in order to isolate epitope and non-epitope presenting cells. Isolated cells were sequenced by pyrosequencing and sequences finally aligned to the RBM3 antigen for identification of epitopes.

A dual-labeling strategy with real-time monitoring of the surface expression level was used (Löfblom, J et al (2005) FEMS Microbiol Lett 248, 189-198). It allowed for normalization of the binding signal with the expression level, provided low cell-to-cell variations and made discrimination of different epitope populations possible. Further, it also allowed for a parallel assay to determine non-binding peptides displayed on the surface.

Two epitopes regions, SEQ ID NO:4 (RGFGFITFTNPE-HASVAMRAMNGESLDGR) and SEQ ID NO:5 (RSYS-RGGGDQGYGSGRYYDSRPGG), within SEQ ID NO:1 were identified.

5. Epitope Mapping Using Luminex a) Synthetic Peptide Preparation

A PEPscreen library consisting of 25 biotinylated peptides corresponding to the PrEST HPRR232631 (SEQ ID NO:1) on RBM3 was synthesized by Sigma-Genosys (Sigma-Aldrich). The peptides were 15 amino acids long with a 10 amino acid overlap, together covering the entire PrEST-sequence. The peptides were resolved in 80% DMSO to a final concentration of 10 mg/ml.

b) Bead Coupling

Neutravidin (Pierce, Rockford, Ill.) was immobilized on carboxylated beads (COOH Microspheres, Luminex-Corp., Austin, Tex.) in accordance to the manufacturer's protocol. Coupling of $10^6$ beads was performed using a filter membrane bottomed microtiter plate (MultiScreen-HTS, Millipore, Billerica, Mass.) as previously described (Larsson et al (2009) J Immunol Methods 15; 34(1-2):20-32, Schwenk et al (2007) Mol Cell Proteomics 6(1) 125:32). 25 distinct groups of beads with different color code IDs were activated using 1-Ethyl-3-(3-dimethylamino-propyl) carbodiimide and N-Hydroxysuccinimide. Neutravidin (100 µg/ml in MES) was added to the beads and incubated for 120 min on a shaker. The beads were finally washed, re-suspended, and transferred to microcentrifuge tubes for storage at 4° C. in a protein containing buffer (BRE, Blocking Reagent for ELISA, Roche, Basel, Switzerland) supplemented with NaN3. All coupled bead populations were treated with sonication in an ultrasonic cleaner (Branson Ultrasonic Corporation, Danbury, Conn.) for 5 min. The biotinylated peptides were diluted in BRE to a concentration of 20 µM, and 100 µl of each peptide was used in the coupling reaction, which was conducted for 60 min with shaking at RT. Finally, the beads were washed with 3×100 µl BRE buffer and stored at 4° C. until further use.

c) Determination of Binding Specificity

A bead mixture containing all 25 bead IDs was prepared and 45 µl of each antibody diluted to 50 ng/ml in PBS was mixed with 5 µl of the bead mix and incubated for 60 min at RT. A filter bottomed microtiter plate (Millipore) was utilized for washing and following each incubation all wells were washed with 3×100 µl PBST. 50 µl of R-Phycoerythrine labeled anti-rabbit IgG antibody (0.5 µg/ml, Jackson ImmunoResearch) or 50 µl of Alexa Fluor 555 goat anti-mouse IgG were added (0.4 ug/ml) for a final incubation of 60 min at RT.

Measurements were performed using the Luminex LX200 instrumentation with Luminex xPONENT software. For each experiment 50 events per bead ID were counted and the median fluorescence intensity (MFI) was used as a measurement of antibody binding to individual bead populations.

d) Results

The specificities of the monospecific polyclonal antibody (anti-RBM3) and the monoclonal antibody 6F11 were tested in an assay using beads coupled with synthetic biotinylated peptides. Anti-RBM3 showed strong binding to 8 of the peptides, namely 6, 7, 8, 14, 15, 16, 24 and 25, corresponding to three distinct regions on the PrEST sequence, consensus sequences SEQ ID NO: 6, 7, 8 and 9. In particular peptide 24 and 25, corresponding to SEQ ID NO:9 generated a strong signal. The monoclonal antibody 6F11 reacted with two peptides: 15 and 16, corresponding to one distinct region on the PrEST sequence, consensus sequence SEQ ID NO: 8. As both anti-RBM3 and 6F11 bound to peptides 15 and 16, this indicates that these antibodies share one or more epitope(s) within this region. It is notable that SEQ ID NO:6 is within SEQ ID NO:4 and that SEQ ID NO:8 to some extent overlaps with SEQ ID NO:5.

6. Epitope Mapping Using Bacterial Display II

RBM3 DNA corresponding to SEQ ID NO:1 (i.e. aa 18-151 of ENSP00000365946 or by 261-682 ENST00000376755) was amplified by PCR using vector pAff8c as template. The amplified DNA was fragmentized to various lengths (approximately 50-150 bp) by sonication, followed by ligation into the staphylococcal display vector (pSCEM2) and transformed into *S. Carnosus* yielding around 100000 transformants. In-frame DNA fragments were displayed as peptides on the staphylococcal surface. After incubation with antibody (anti-RBM3 obtained in Section 2 and monoclonal antibodies obtained in Section 3) and fluorescently labeled secondary reagents, positive and negative cells were separately sorted using flow cytometry in order to isolate epitope and non-epitope presenting cells. Plasmid DNA from isolated cells was sequenced by Sanger sequencing and sequences were aligned to the RBM3 antigen for identification of epitopes.

A dual-labeling strategy with real-time monitoring of the surface expression level was used (Löfblom, J et al (2005) FEMS Microbiol Lett 248, 189-198). It allowed for normalization of the binding signal with the expression level, provided low cell-to-cell variations and made discrimination of different epitope populations possible. Further, it also allowed for a parallel assay to determine non-binding peptides displayed on the surface.

For the polyclonal antibody, the regions SEQ ID NO:10-15 within SEQ ID NO:1, were identified. In particular, the regions SEQ ID NO:11 and SEQ ID NO:12 were of interest, since they were found within the earlier identified region SEQ ID NO:4. Further, the regions SEQ ID NO:13 and 14 were particularly interesting, since they to a large extent overlapped with previously identified SEQ ID NO:6 and 7, respectively.

For the monoclonal antibody 6F11, the region SEQ ID NO:16 within SEQ ID NO:1 was identified, and this region (SEQ ID NO:16) is within the earlier identified region SEQ ID NO:5. The epitope region of 6F11 identified here in Section 6 has a one-amino acid overlap with the 6F11 epitope region identified in Section 5. The results of Sections 5 and 6 are, however, not in contrast; one of the peptides found to bind 6F11 in Section 5 (peptide 16) comprises SEQ ID NO:16 (and SEQ ID NO:19). The results of Sections 5 and 6 may thus be considered complementary.

For the monoclonal antibody 1B5, the region SEQ ID NO:17 within SEQ ID NO:1 was identified, and this region (SEQ ID NO:17) was also found within the earlier identified region SEQ ID NO:5. For the monoclonal antibody 7G3, the region SEQ ID NO:18 within SEQ ID NO:1 was identified. This region (SEQ ID NO:18) was also found within the earlier identified region SEQ ID NO:5. This region (SEQ ID NO:18) overlaps with the epitope for the 6F11 antibody (SEQ ID NO:16). For the monoclonal antibody 9B11, the region SEQ ID NO:19 within SEQ ID NO:1 was identified.

Array Analysis

7. Discovery TMA a) Material and Methods

Paraffin cores containing neoplastic tissue from 20 different cancer types were analyzed using the monoclonal antibody 1B5, obtained in Examples, section 3. All tissues used as donor blocks for tissue microarray (TMA) production were selected from the archives at the Department of Pathology, University Hospital, Uppsala, in agreement with approval from the local ethical committee. The tissue sections used for TMA analysis were examined to determine diagnosis and classification. All tissues were formalin fixated, paraffin embedded, and sectioned for diagnostic purposes.

The TMA production was performed essentially as previously described (Kononen J et al (1998) Nature Med. 4:844-847; Kallioniemi O P et al (2001) Hum. Mol. Genet. 10:657-662). Briefly, a hole was made in the recipient TMA block and a cylindrical core tissue sample from the donor block was acquired and deposited in the recipient TMA block. This was repeated in an automated tissue arrayer from Beecher Instrument (ATA-27, Beecher Instruments, Sun Prairie, Calif., USA) until a complete TMA design was produced. TMA recipient blocks were baked at 42° C. for 2 h prior to sectioning.

The design of TMA:s was focused on including representative cancer tissues. This has previously been described in detail in Kampf C et al (2004) Clin. Proteomics 1:285-300. In brief, samples from 20 of the most common cancer types affecting humans were selected. Each TMA block contained 72 cores of tissue with 1 mm diameter. For 17 of the 20 cancer types, 12 individually different tumors were sampled, and for the remaining 3 cancer types, 4 individually different tumors were sampled, all in duplicates from the same tumor. The TMA blocks were sectioned with 4 µm thickness using a waterfall microtome (Leica), and placed onto SuperFrost® (Roche Applied Science) glass slides for IHC analysis.

Automated IHC was performed as previously described (Kampf C et al (2004) Clin. Proteomics 1:285-300). In brief, the glass slides were incubated for 45 min in 60° C., deparaffinized in xylene (2×15 min) and hydrated in graded alcohols. For antigen retrieval, slides were immersed in TRS (Target Retrieval Solution, pH 6.0, DakoCytomation) and boiled for 4 min at 125° C. in a Decloaking Chamber® (Biocare Medical). Slides were placed in the Autostainer® (DakoCytomation) and endogenous peroxidase was initially blocked with $H_2O_2$ (DakoCytomation). The slides were incubated for 30 min at room temperature with the primary antibody obtained as described in Examples, Section 3, followed by incubation for 30 min at room temperature with goat anti-mouse peroxidase conjugated Envision®. Between all steps, slides were rinsed in wash buffer (DakoCytomation). Finally, diaminobenzidine (DakoCytomation) was used as chromogen and Harris hematoxylin (Sigma-Aldrich) was used for counterstaining. The slides were mounted with Pertex® (Histolab).

All immunohistochemically stained sections from the different TMA:s were scanned using a ScanScope T2 automated slide-scanning systems (Aperio Technologies). In order to represent the total content of the TMA:s, digital images were generated. Scanning was performed at 20 times magnification. Digital images were separated and extracted as individual tagged image file format (TIFF) files for storage of original data. In order to be able to handle the images in a web-based annotation system, the individual images were compressed from TIFF format into JPEG format. All images of immunohistochemically stained tissue were manually evaluated under the microscope and annotated by a certified pathologist or by specially educated personnel and subsequently verified by a pathologist.

Annotation of each different cancer tissue was performed using a simplified scheme for classification of IHC outcome. Each tissue was examined for representativity and immunoreactivity. For each cancer, tumor cells and stroma were annotated. Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak=faint immunoreactivity, moderate=medium immunoreactivity or strong=distinct and strong immunoreactivity. The fraction of stained cells was estimated and classified as <2%, 2-25%, >25-75% or >75% immunoreactive cells of the relevant cell population. Based on both the intensity and fraction of immunoreactive cells, a "staining score" was given for each tissue sample: 0=negative, 1=weak, 2=moderate and 3=strong. N.R. means that no representative tissues were present. In detail, the staining score was given according to the following criteria: 0 was given if SI=absent and FSC=0-100% or if SI=weak and FSC≤25%; 1 was given if SI=weak and FSC>25% or if SI=moderate and FSC≤25%; 2 was given if SI=moderate and FSC>25% or if SI=strong and FSC≤25% and finally 3 was given if SI=strong and FSC>25%, see Table 1. The skilled artisan will recognize that this procedure is similar to a calculation of an Allred score, see e.g. Allred et al (1998) Mod Pathol 11(2), 155.

TABLE 1

Staining score

| Staining score | Staining intensity | Fraction of stained cells |
|---|---|---|
| 0 | Absent | <2% |
| 0 | Absent | 2-25% |
| 0 | Absent | >25-75% |
| 0 | Absent | >75% |
| 0 | Weak | <2% |
| 0 | Weak | 2-25% |
| 1 | Weak | >25-75% |
| 1 | Weak | >75% |
| 1 | Moderate | <2% |
| 1 | Moderate | 2-25% |
| 2 | Moderate | >25-75% |
| 2 | Moderate | >75% |
| 2 | Strong | <2% |
| 2 | Strong | 2-25% |
| 3 | Strong | >25-75% |
| 3 | Strong | >75% | b) Results

Table 2 shows the level of RBM3 protein expression in tissue samples from various cancer types. RBM3 protein expression is found in all cancer types tested but thyroid cancer. However, samples from only three different subjects could be examined for thyroid cancer. For example, it is shown that the staining scores are ranging from 0 to 2 among the breast cancer subjects, from 0 to 2 among the cervical cancer subjects, from 0 to 3 among the colorectal cancer subjects, from 0 to 2 among the head and neck cancer subjects, from 0 to 2 among the lung cancer subjects, from 0 to 2 among the ovarian cancer subjects, from 0 to 2 among the testicular cancer subjects and from 0 to 2 among the urothelial cancer subjects. It may thus be concluded that the RBM3 protein is in general differentially expressed in cancer tissue, supporting its role as a treatment predictive marker in various types of cancers.

TABLE 2

Expression pattern of RBM3 in 20 cancer types

| | Patient number | | | | | | | | | | | |
|---|---|---|---|---|---|---|---|---|---|---|---|---|
| Cancer type | 1 | 2 | 3 | 4 | 5 | 6 | 7 | 8 | 9 | 10 | 11 | 12 |
| Breast cancer | 2 | 2 | 2 | 2 | 1 | 1 | 1 | 1 | 1 | 1 | 0 | 0 |
| Cervical cancer | 2 | 1 | 1 | 1 | 0 | 0 | 0 | 0 | 0 | 0 | 0 | 0 |
| Colorectal cancer | 3 | 3 | 2 | 2 | 2 | 2 | 2 | 0 | 0 | 0 | 0 | N.R. |
| Endometrial cancer | 3 | 1 | 1 | 1 | 1 | 1 | 1 | 0 | 0 | 0 | 0 | 0 |
| Head & neck cancer | 2 | 2 | 0 | 0 | | | | | | | | |
| Kidney cancer | 3 | 3 | 2 | 2 | 2 | 2 | 2 | 2 | 1 | 1 | 1 | 1 |
| Liver cancer | 1 | 1 | 1 | 0 | 0 | 0 | 0 | 0 | 0 | 0 | 0 | 0 |
| Lung cancer | 2 | 2 | 1 | 1 | 1 | 1 | 1 | 0 | 0 | 0 | N.R. | N.R. |

TABLE 2-continued

Expression pattern of RBM3 in 20 cancer types

| Cancer type | Patient number | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Malignant carcinoid | 1 | 0 | 0 | 0 | | | | | | | | |
| Malignant glioma | 2 | 1 | 0 | 0 | 0 | 0 | 0 | 0 | 0 | 0 | N.R. | N.R. |
| Malignant lymphoma | 2 | 2 | 2 | 1 | 1 | 1 | 1 | 0 | 0 | 0 | 0 | 0 |
| Malignant melanoma | 3 | 2 | 2 | 2 | 2 | 1 | 1 | 0 | 0 | 0 | 0 | 0 |
| Ovarian cancer | 2 | 1 | 1 | 1 | 1 | 1 | 0 | 0 | 0 | 0 | 0 | 0 |
| Pancreatic cancer | 2 | 1 | 1 | 1 | 1 | 1 | 0 | 0 | 0 | 0 | 0 | N.R. |
| Prostate cancer | 2 | 1 | 1 | 1 | 0 | 0 | 0 | 0 | 0 | 0 | 0 | N.R. |
| Skin cancer | 3 | 3 | 2 | 2 | 2 | 2 | 2 | 2 | 1 | 1 | 1 | 1 |
| Stomach cancer | 2 | 1 | 1 | 1 | 1 | 1 | 0 | 0 | 0 | N.R. | N.R. | N.R. |
| Testicular cancer | 2 | 1 | 0 | 0 | 0 | 0 | 0 | 0 | 0 | 0 | 0 | N.R. |
| Thyroid cancer | 0 | 0 | 0 | N.R. | | | | | | | | |
| Urothelial cancer | 2 | 2 | 1 | 1 | 0 | 0 | 0 | 0 | 0 | 0 | 0 | N.R. |

8. Ovarian Cancer TMA, Prospective Cohort a) Material and Methods

Archival formalin-fixed paraffin-embedded tissues from 154 patients surgically treated for primary invasive epithelial ovarian cancer were collected from the Pathology departments at Lund and Malmo University Hospitals, Sweden. Patients were diagnosed between 1982 and 2007. Ethical permission was obtained from the Local Ethics Committee in Lund.

The median age of patients was 63 (47-83) years. Stage (according to the FIGO scale) was recorded for all specimens: 26 tumors were stage I, 18 tumors were stage II, 75 stage III and 22 stage IV. Also grade was recorded: 8 tumors were well differentiated (grade 1), 39 were moderately differentiated (grade 2) and 107 were poorly differentiated (grade 3). The cohort included 90 cases of serous carcinoma, 35 endometrioid carcinomas, 12 mucinous carcinomas, 9 clear cell carcinomas, 1 Brenner tumor and 7 of indeterminate histological type. Median follow-up time was 2.67 years. Treatment data was available for 73 patients. Standard therapy was platinum-based chemotherapy, from the 1990s in combination with paclitaxel.

All 154 cases were histopathologically re-evaluated on slides stained with hematoxylin and eosin. TMA:s were then constructed by sampling 2×1.0 mm cores per case from areas representative of epithelial ovarian cancer.

The material was analyzed according to the following method using both the polyclonal antibody produced according to Section 2 above (Anti-RBM3) and the monoclonal antibody 1B5 produced according to Section 3 above. Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking Chamber® (Biocare Medical). Slides were placed in the Autostainer® (Dako) and endogenous peroxidase was initially blocked with $H_2O_2$ (Dako). The slides were incubated for 30 min at room temperature with the primary RBM3 antibody (Anti-RBM3 or 1B5). This was followed by incubation for 30 min at room temperature with a secondary goat anti-peroxidase (anti-rabbit or anti-mouse) conjugated Envision® (Dako). Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak-moderate=faint to medium immunoreactivity, or strong=distinct and strong immunoreactivity. Also fraction of stained cells was subjectively evaluated in accordance to standards used in clinical histo-pathological diagnostics and outcome was classified as: <2%, 2-25%, >25-75% or >75% immunoreactive cells of the relevant cell population. The skilled artisan will recognize that this annotation procedure is similar to a calculation of an Allred score, see e.g. Allred et al (1998) Mod Pathol 11(2), 155. Thus, tissue annotation was essentially done as described in Examples Section 7 above.

For statistical analyses where the polyclonal antibody was used, staining intensity and fraction of stained cells were not combined to yield a "staining score", the nuclear fraction (NF), nuclear intensity (NI) level and cytoplasmic intensity (CI) level was evaluated separately. Based on the survival trends for individual strata, dichotomized variables were constructed for further statistical analyses. A high nuclear fraction was defined as >75% (NF=3) fraction of cells stained and a low nuclear fraction was defined as 0-75% (NF<3) fraction of cells stained. Further, a high protein expression level was defined as a strong nuclear intensity (NI=3) and a low protein expression level was defined as an absent—weak and moderate nuclear intensity (NI<3). Also, a high protein expression level was defined as a strong cytoplasmic intensity (CI=2) and a low protein expression level was defined as an absent and weak/moderate cytoplasmic intensity (CI<2). The above classifications of samples were used for overall survival (OS) and ovarian cancer specific survival (OCSS) analyses according to the Kaplan-Meier method, and the log-rank test was used to compare survival in different strata. All statistical tests were two-sided, and p-values of <0.05% were considered significant. All calculations were made with the statistical package SPSS 17.0 (SPSS Inc. Illinois, USA).

For statistical analyses where the monoclonal 1B5 antibody was used, nucleic and cytoplasmic staining were combined to yield a staining score (SS) ranging from 0 to 2. Only intensity was considered but most positive tumors had a fraction level of >50%. SS=0 was defines as absent expression, SS=1 was defined as a weak or moderate expression and SS=2 was defined as a strong expression.

Based on the survival trends for individual strata, dichotomized variables were constructed for further statistical analyses. A high staining score was defined as SS>0 or SS=2. A low staining score was defined as SS=0 or SS<2. The above classifications of samples were used for overall survival (OS) analysis according to the Kaplan-Meier method, and the log-rank test was used to compare survival in different strata. All statistical tests were two-sided, and p-values of <0.05% were considered significant. All calculations were made with the statistical package SPSS 17.0 (SPSS Inc. Illinois, USA).

b) Results

Figure 1B:
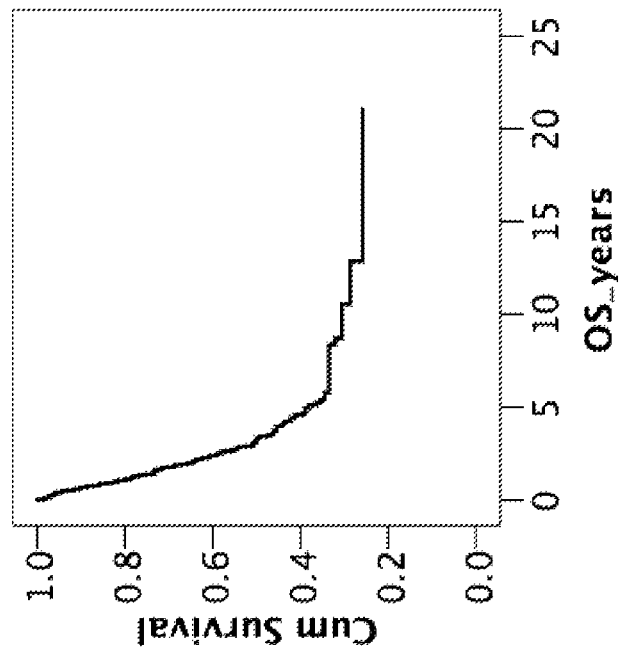
FIG. 1B shows ovarian cancer specific survival (OCSS). Estimated five-year survival is approximately 39% for all patients in this cohort.

Initial analysis of the cohort revealed that OS for all patients was approximately 38% and OCSS was approximately 39%, as seen in FIGS. 1A and 1B, respectively.

Immunohistochemical analysis of RBM3 expression with anti-RBM3 could be performed on all the 154 tumor samples. A positive nuclear fraction (NF>0) was observed in 147 of the 154 tissue cores (95%). Tumor cells with a nucleic staining (NI>0) were observed in 147 of the 154 subjects (95%) and tumor cells with a cytoplasmic staining (CI>0) were observed in 84 of the 154 subjects (55%).

Immunohistochemical analysis of RBM3 expression with 1B5 could be performed on 149 of the 154 tumor samples. A positive staining score (SS>0) was observed in 55 of the 149 tissue cores (37%).

Figure 2A:
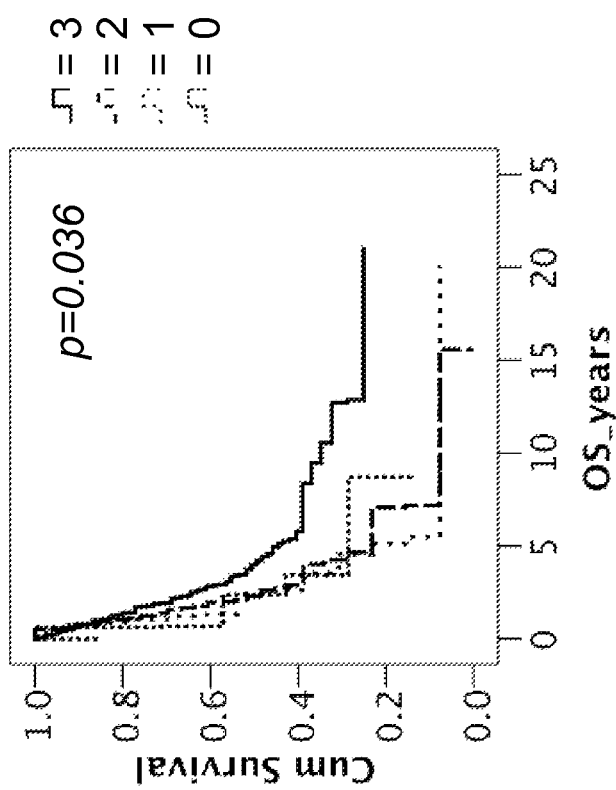
In FIG. 2A all subjects were split into four groups based on NF status, i.e. <2% (O), 2-25% (1), >25-75% (2) or >75% (3).
Figure 2B:
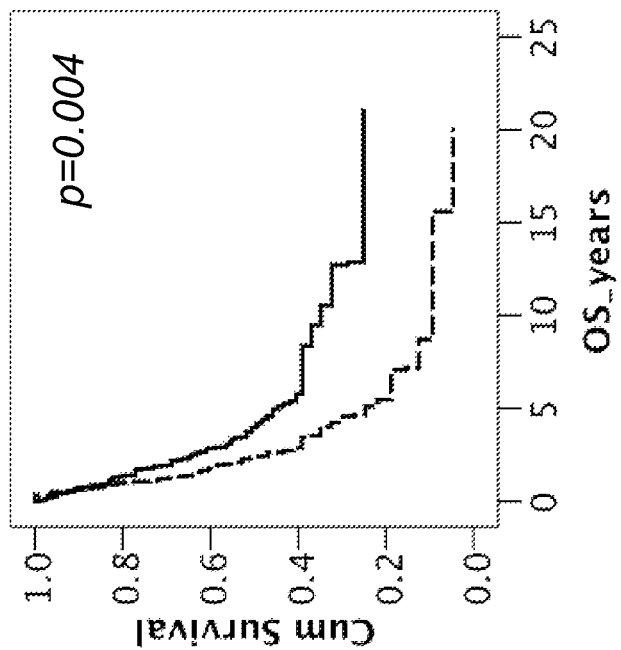
In FIG. 2B a solid line represents a high NF level of RBM3 (NF>75%), and a dotted line represents a low NF level of RBM3 (NF≤75%).
Figure 4:
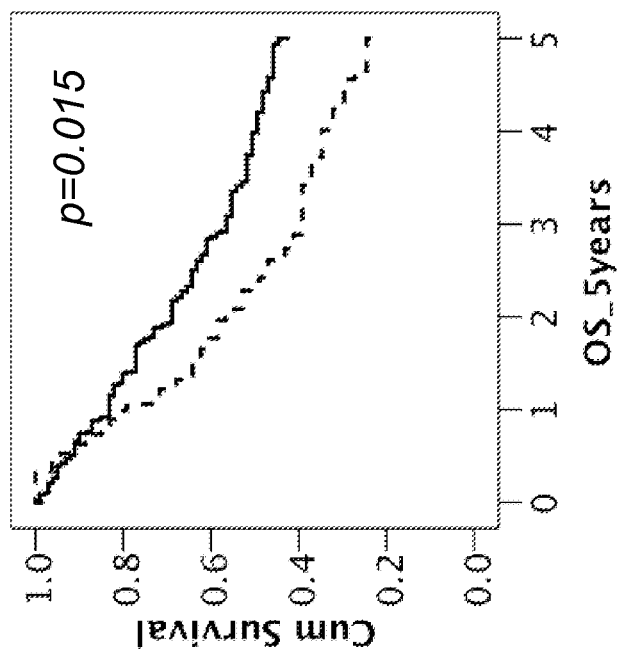
FIG. 4 shows the impact of the NF level of RBM3 on OS in all 154 patients over a period of the first five years after treatment. Estimated five-year survival is approximately 44% for RBM3 high (NF>75%) patients (solid line) and approximately 25% for RBM3 low (NF≤75%) patients (dotted line) in this cohort.
Figure 5B:
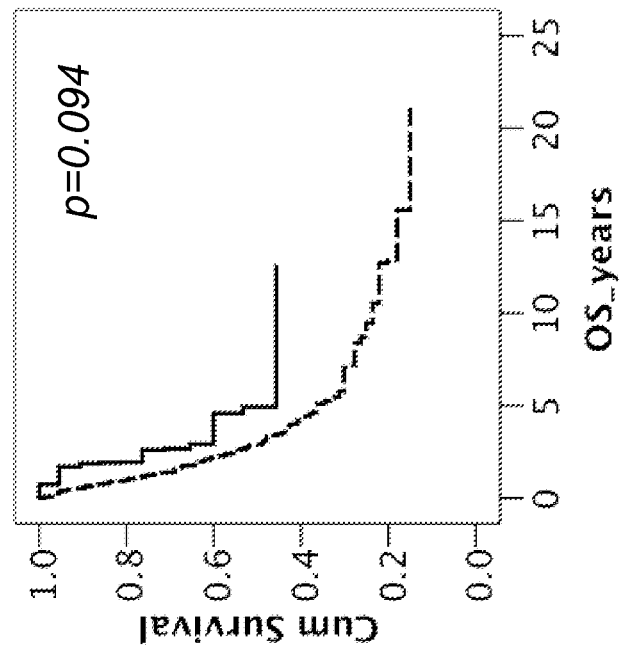
In FIG. 5B a solid line represents a high CI level of RBM3 (CI=2), and a dotted line represents a low CI level of RBM3 (CI<2).
Figure 5A:
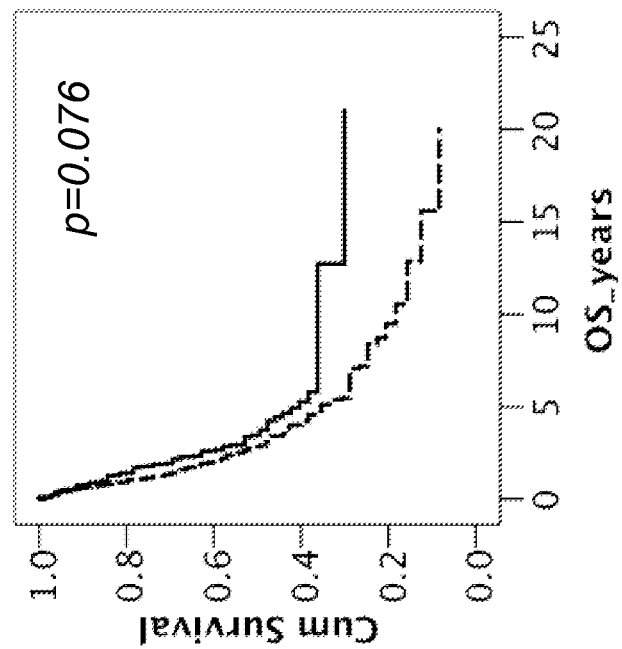
In FIG. 5A a solid line represents a high NI level of RBM3 (NI=3), and a dotted line represents a low NI level of RBM3 (NI<3).
Figure 6B:
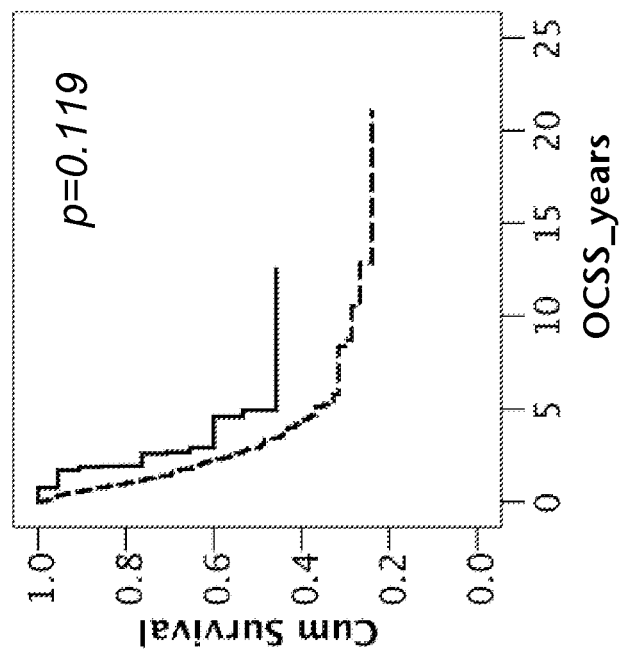
In FIG. 6B a solid line represents a high CI level of RBM3 (CI=2), and a dotted line represents a low CI level of RBM3 (CI<2).
Figure 6A:
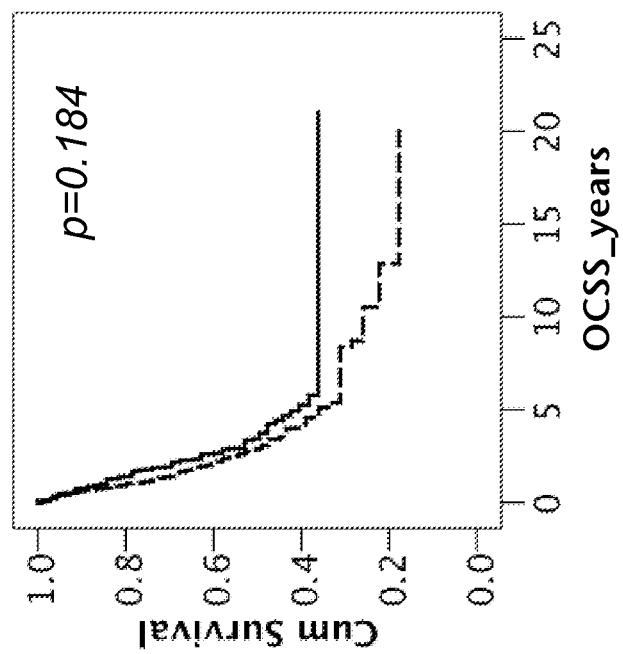
In FIG. 6A a solid line represents a high NI level of RBM3 (NI=3), and a dotted line represents a low NI level of RBM3 (NI<3).
Figure 7B:
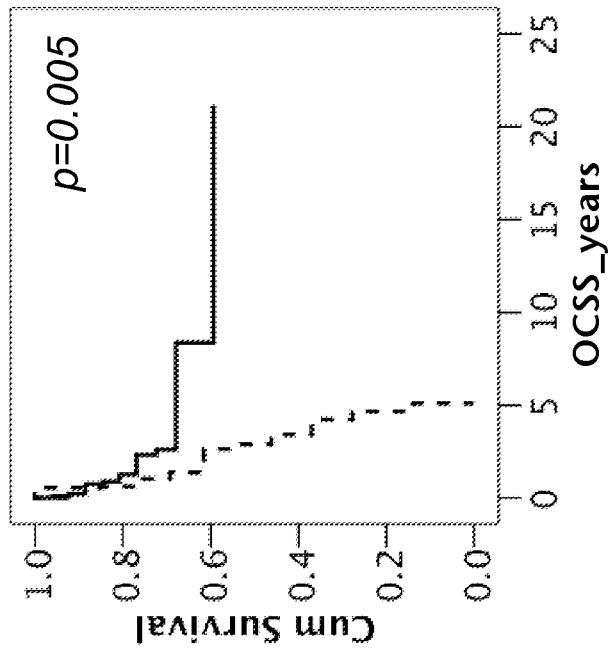
FIG. 7B shows OCSS.
Figure 7A:
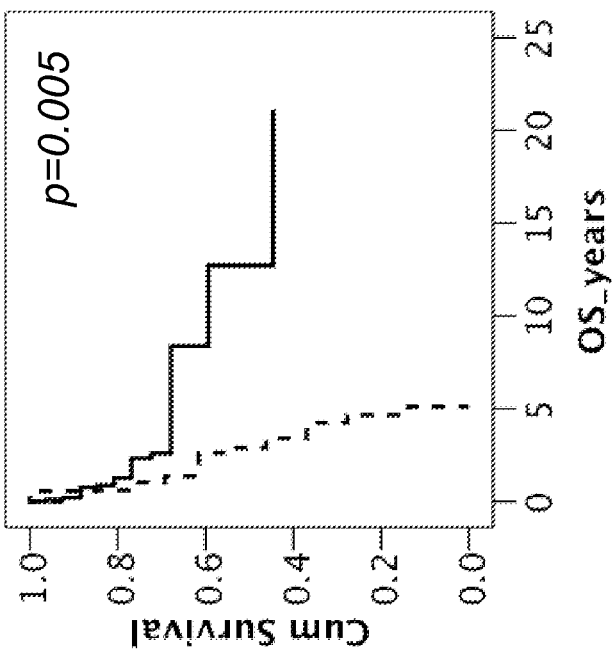
FIG. 7A shows OS.
Figure 8B:
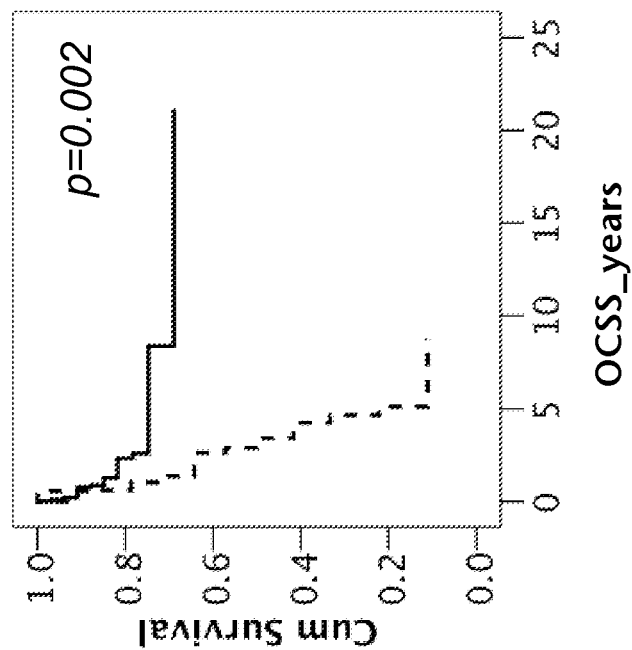
FIG. 8B shows OCSS.
Figure 8A:
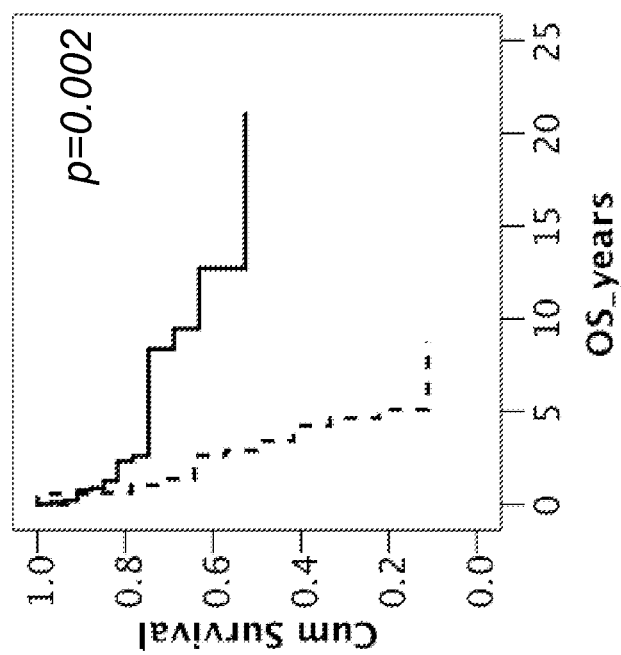
FIG. 8A shows OS.

Survival analysis of the entire cohort revealed that the fraction of stained tumor cells positive for anti-RBM3 significantly correlated with OS (FIGS. 2A and 2B) and OCSS (FIGS. 3A and 3B), i.e. a high RBM3 protein level corresponded to a better survival. For patients having a fraction value of NF>75%, five-year OS was approximately 44%, whereas patients having a RBM3 fraction value of NF 75% had an OS of about 25% (FIG. 4). Also nuclear- and cytoplasmic intensity level showed a correlation with OS (FIGS. 5A and 5B) and OCSS (FIGS. 6A and 6B).

Surprisingly, the correlation between the RBM3 protein level and survival, both OS and OCSS, was particularly significant when the group of patients having grade 2 (moderately differentiated) tumors (FIGS. 7A and 7B) or grade 1 or 2 (well or moderately differentiated) tumors (FIGS. 8A and 8B) was analyzed separately. Consequently, patients diagnosed with well- or moderately differentiated EOC may be particularly suitable for analysis of the RBM3 protein level.

Figure 9B:
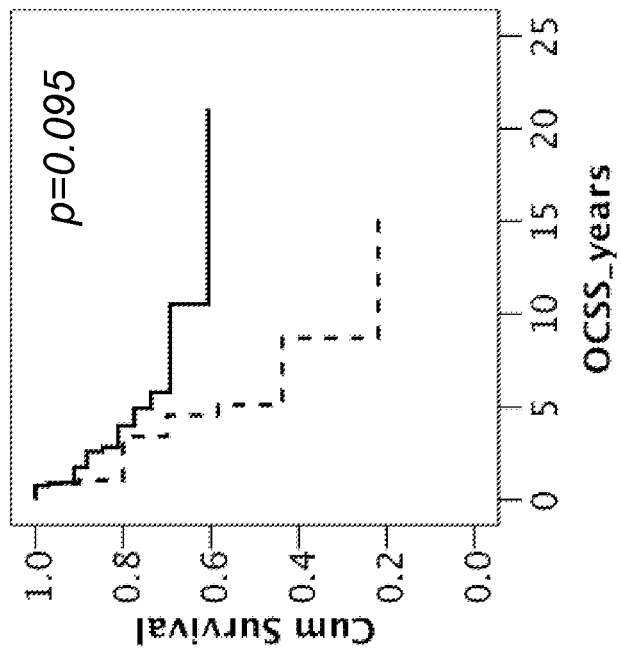
FIG. 9B shows OCSS.
Figure 9A:
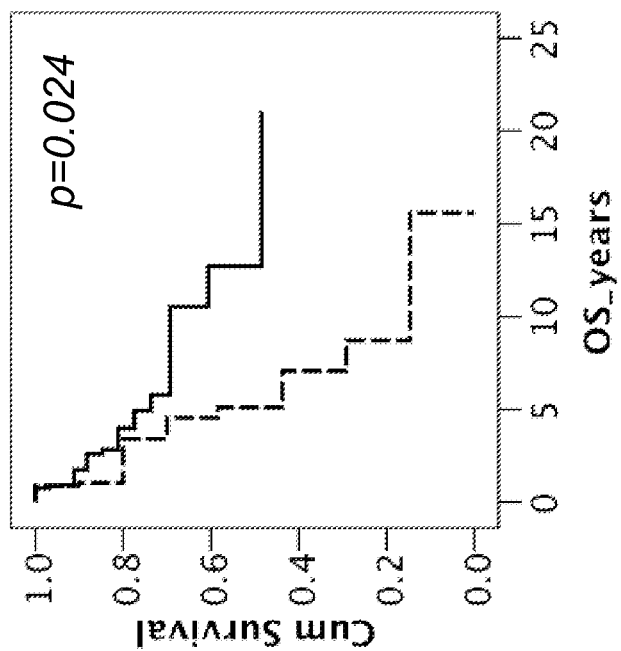
FIG. 9A shows OS.

Interestingly, the RBM3 protein level was also significantly correlated with OS and OCSS in patients diagnosed with stage I or II EOC. (FIGS. 9a and 9B). Consequently, patients diagnosed with stage I or II EOC may be particularly suitable for analysis of RBM3 protein level.

Figure 10B:
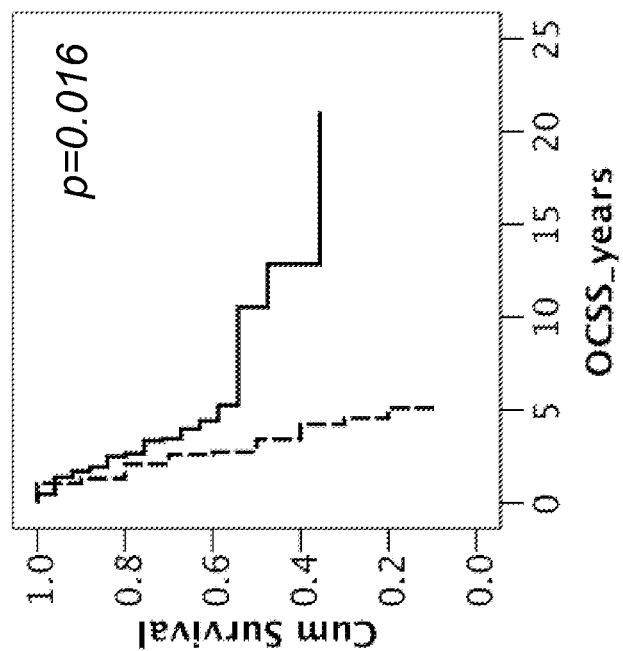
FIG. 10B shows OCSS.
Figure 10A:
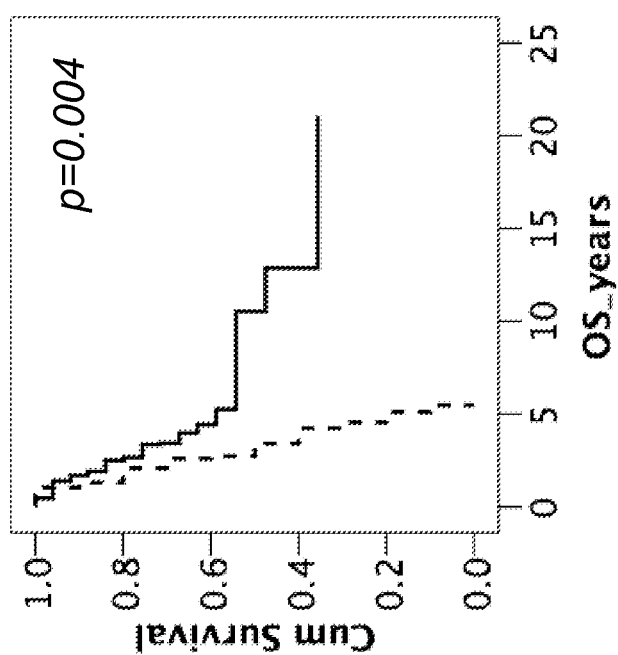
FIG. 10A shows OS.
Figure 11A:
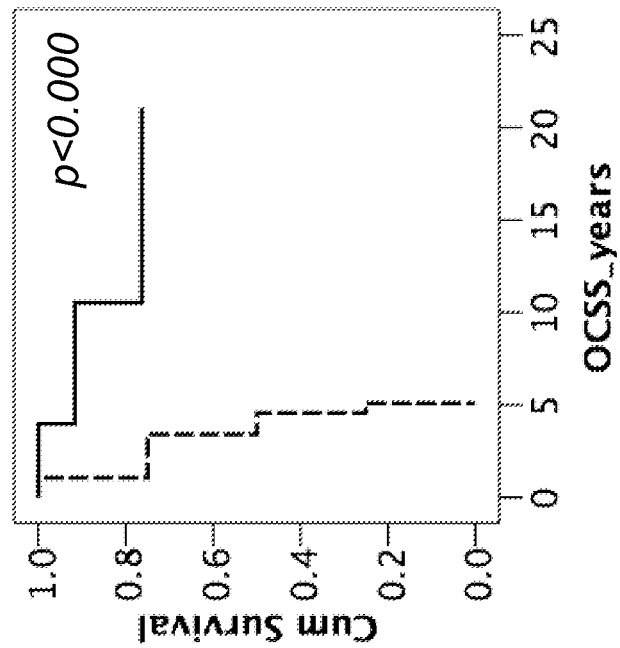
FIG. 11A shows OS.
Figure 11B:
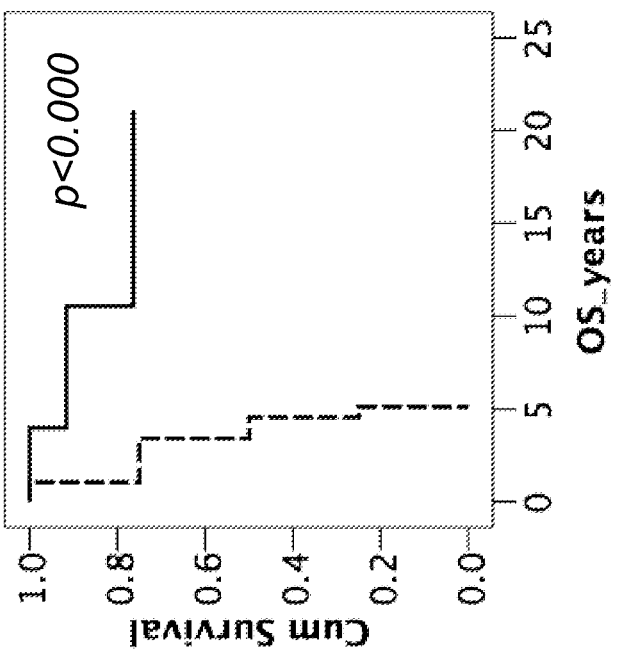
FIG. 11B shows OCSS.
Figure 12B:
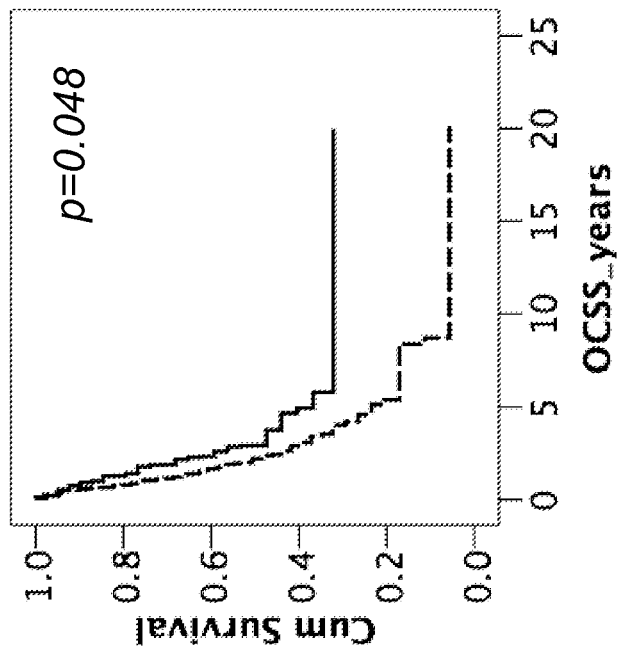
FIG. 12B shows OCSS.

Further, the RBM3 protein level was also significantly correlated with OS and OCSS in the subgroup of patients having endometroid tumors (FIGS. 10A and 10B). The impact on survival was even more accentuated if only patients with endometroid EOC at stage I or II were analyzed (FIGS. 11A and 12B). Consequently, patients diagnosed with endometroid EOC may be particularly suitable for analysis of RBM3 protein level.

Figure 12A:
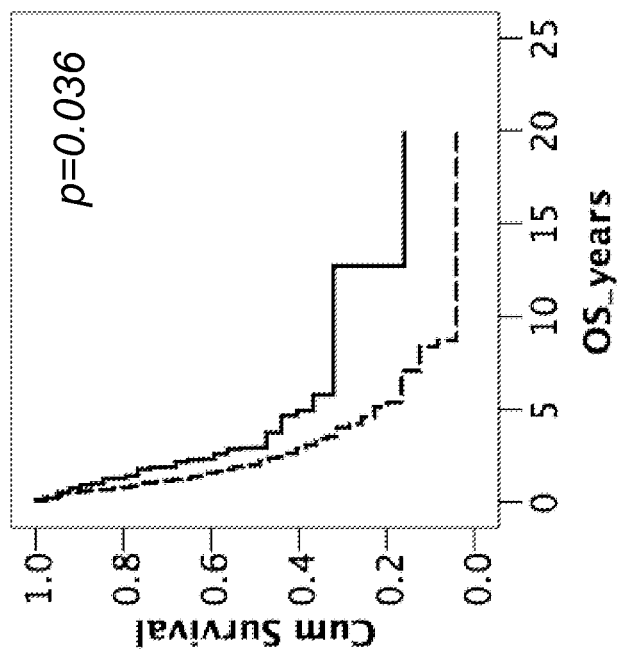
FIG. 12A shows OS.
Figure 13B:
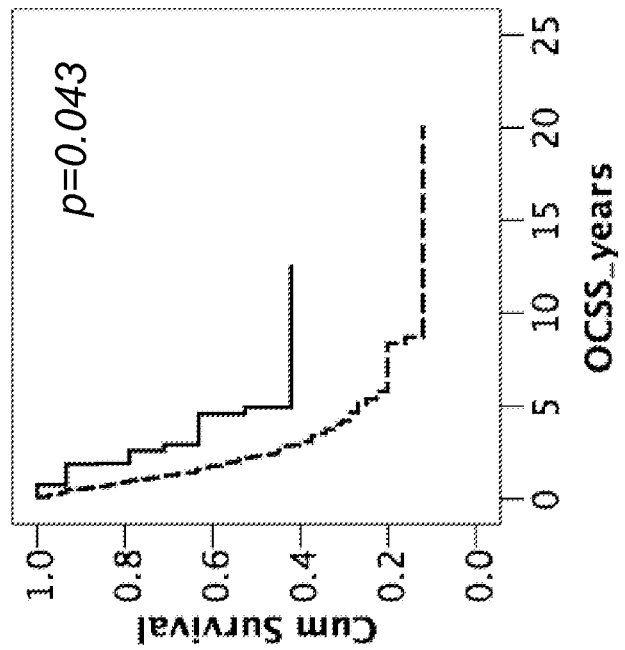
FIG. 13B shows OCSS.
Figure 13A:
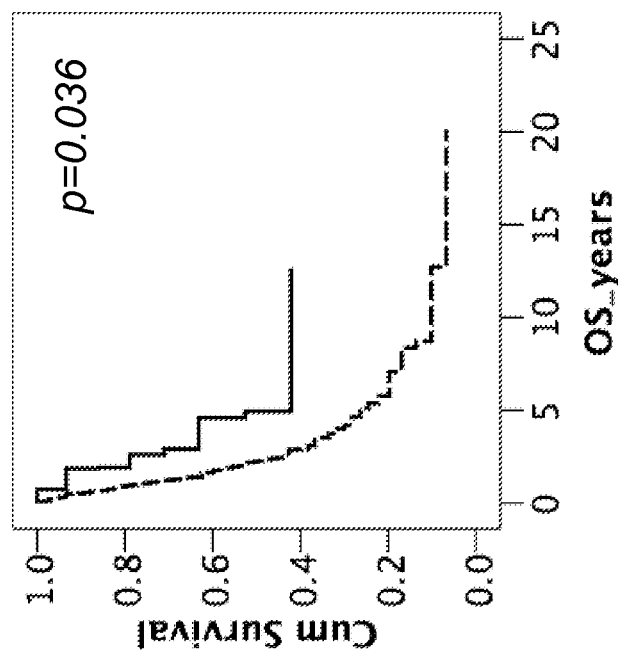
FIG. 13A shows OS.
Figure 14B:
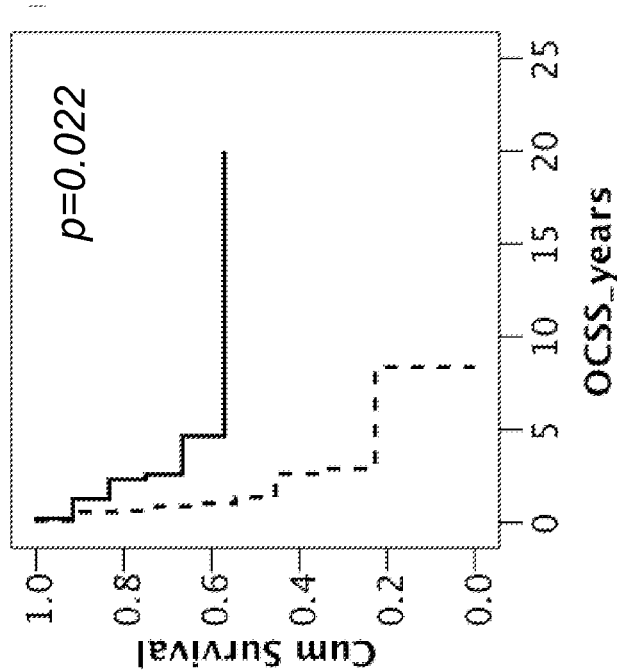
FIG. 14B shows OCSS.
Figure 14A:
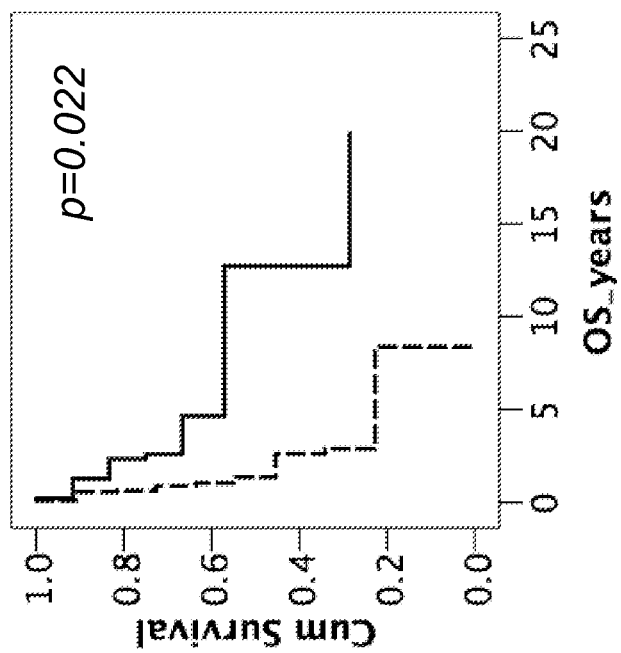
FIG. 14A shows OS.

A significant correlation between the RBM3 protein intensity level and OS and OCSS were also found when the subgroup of patients having serous tumors was analyzed (FIGS. 12 and 13). The impact of RBM3 on survival was even more accentuated if only patients having grade 1 or 2 (well or moderately differentiated) serous EOC were analyzed (FIGS. 14A and 14B). Consequently, patients diagnosed with serous EOC may be particularly suitable for analysis of RBM3 protein level.

Figure 16B:
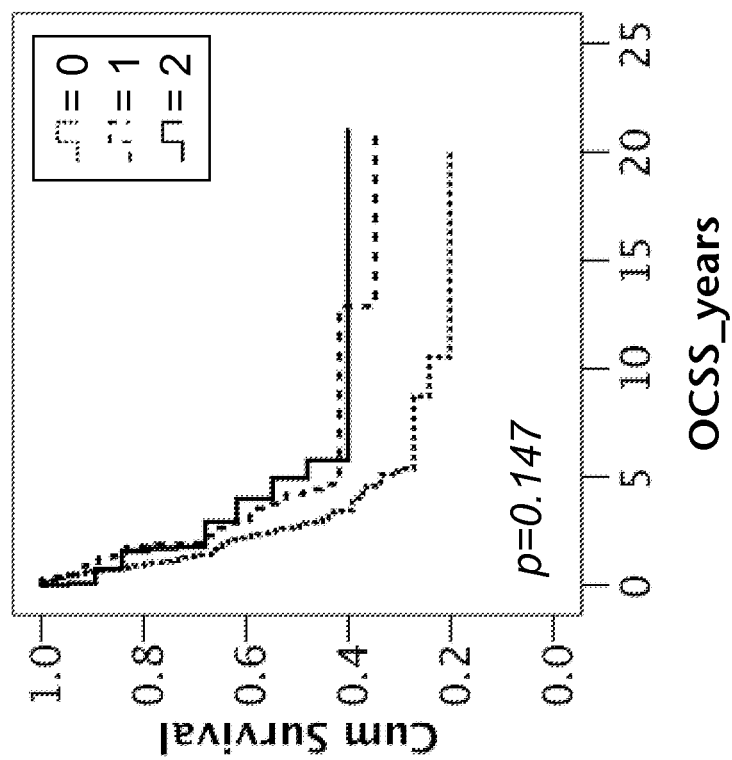
In FIG. 16B RBM3 expression was dichotomized into high and low categories. A solid line represents a high SS of RBM3 expression (SS>0), and a dotted line represents a low SS of RBM3 expression (SS=0).
Figure 16A:
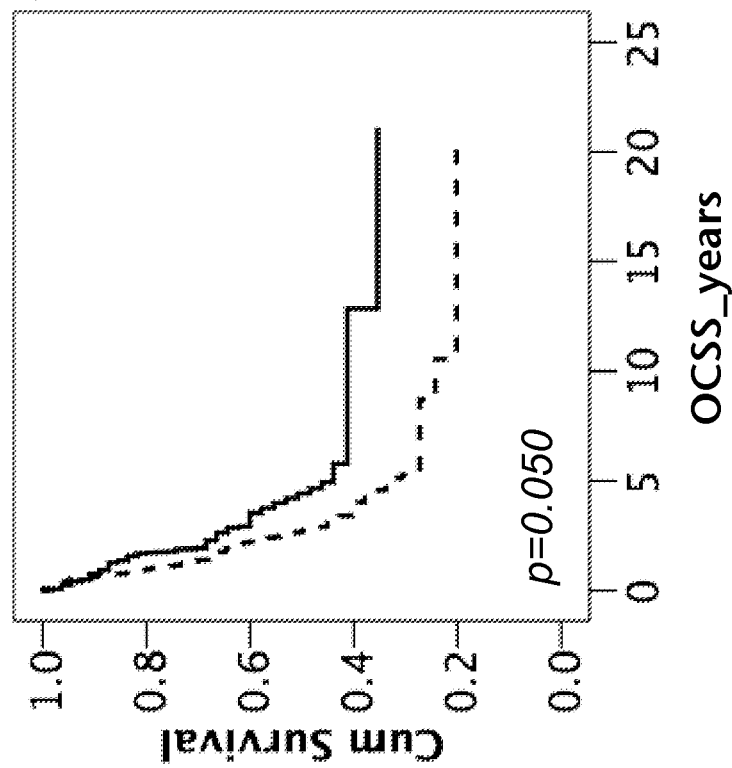
In FIG. 16A all subjects were split into three groups based on SS.

Staining with 1B5 revealed similar results as obtained with anti-RBM3, the fraction of stained tumor cells positive for RBM3 significantly correlated with OS (FIGS. 15A and 15B) and OCSS (FIGS. 16A and 16B), i.e. a high RBM3 protein level corresponded to a better survival.

The correlation between the RBM3 protein level and OS, was particularly significant when the group of patients having grade 1 or 2 (well or moderately differentiated) tumors was analyzed separately (FIG. 17). Consequently, patients diagnosed with well- or moderately differentiated EOC may be particularly suitable for analysis of the RBM3 protein level.

Figure 18:
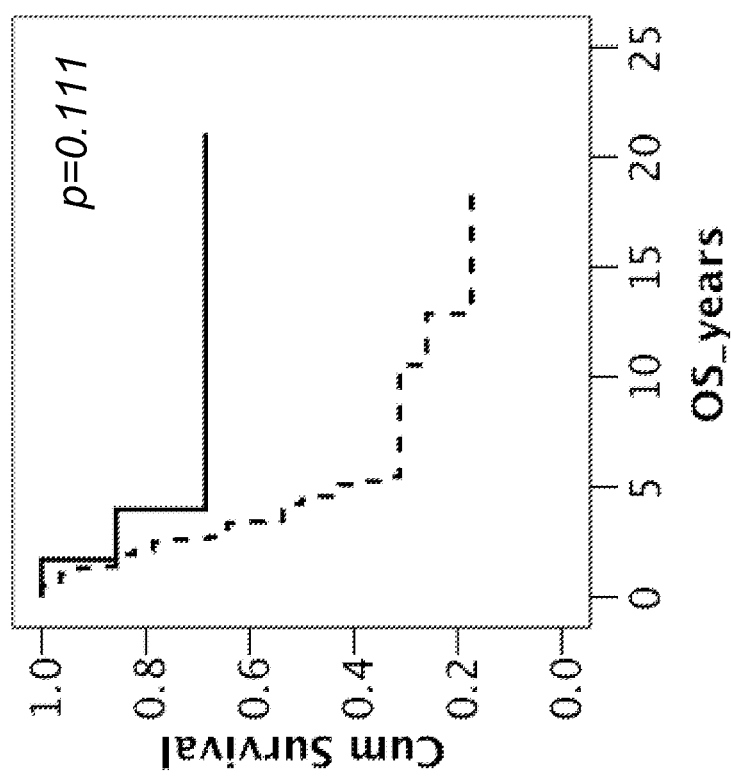
FIG. 18 shows the impact of RBM3 level on OS for patients diagnosed with endometroid EOC. All 35 subjects were stained with the 1B5 monoclonal antibody. RBM3 expression was dichotomized into high and low categories. A solid line represents a high SS of RBM2 expression (SS>2), and a dotted line represents a low SS of RBM3 expression (SS=2).

Further, the RBM3 protein level was also significantly correlated with OS in the subgroup of patients having endometroid tumors (FIG. 18).

In conclusion, EOC subjects treated with a platinum-based agent are shown to have a better survival if they are RBM3 high than if they are RBM3 low.

9. Gene Expression Analysis of Ovarian Cancer a) Material and Methods

Data was collected from a previously performed microarray study, based on a patient cohort of 285 patients diagnosed with epithelial ovarian cancer between 1992 and 2006. Institutional Review Board approval for patient consent had been obtained for all patients.

The median age of patients was 59 years (ranging from 18-79 years). The inventors decided to exclude data from 18 patients who received neoadjuvant therapy, as the inventors realized that this treatment could possibly influence RBM3 mRNA levels, and might thus lead to biased results. Further, data from 40 patients who didn't receive platinum based therapy were removed from the data set. Of these 227 samples, 210 came from patients with serous cancer, 16 with endometroid and 1 with adenocarcinoma. For statistical analysis only serous samples were considered. Pathology evaluation data existed for all patients, and recurrence free survival was evaluated for RBM3 high as well as RBM3 low mRNA content.

b) Results

Figure 19:
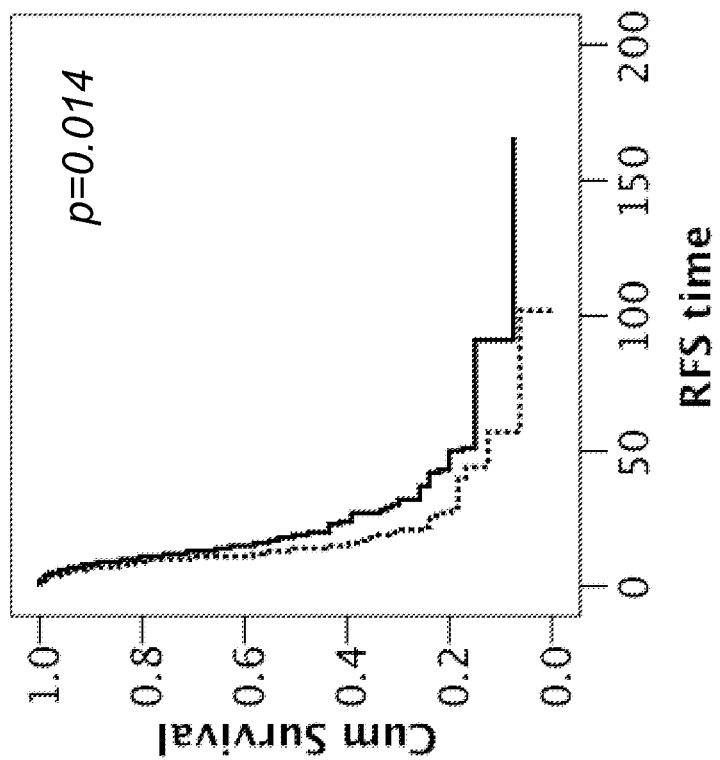
FIG. 19 shows recurrence free survival in ovarian cancer patients with high RBM3 mRNA levels (solid line) and patients with low RBM3 mRNA levels (dotted line).

Array analysis of RBM3 expression were analysed for 210 of the 285 tumor samples. Dichotomized variables were constructed for statistical analysis. As can be seen in FIG. 19, cisplatin-treated patients that had tumors with a high RBM3 expression level, had a significantly better recurrence free survival than patients that had tumors with low RBM3 expression levels.

10. Testis TMA a) Material and Methods

Tumor material was collected from thirty patients diagnosed with testicular germ-cell tumors (TGCT) in the Department of Pathology, UMAS, between 1995 and 2008. Five of the samples were pure seminoma and 25 were non-seminomatous TGCT. Non-seminomatous TGCT were classified according to the International Germ Cell Cancer Collaborative Group (IGCCC). Four of the 25 samples were cases classified as IGCCC intermediate prognosis and five samples as IGCCC poor prognosis. The remaining 16 non-seminomatous TGCT cases were classified as IGCCC good prognosis. Permission for this study was obtained from the Ethics Committee at Lund University; ref nr 447-07 and 493-09. Five patients died from their disease, 4 of whom were IGCCC poor and 1 IGCCC intermediate. All patients received cisplatin treatment.

Prior to TMA construction, all available haematoxylin and eosin stained slides from each case were histopathologically re-evaluated. The total number of histological subtypes was denoted and areas representing each subtype delineated, including difficult-to-classify areas. Full-face sections, as many as needed to cover all different components in each case, were then stained for SOX-2 and CD30, to further refine and revise the classification. From one case, only autopsy material was available for analysis. A standard set of 4×1 mm cores were taken from each invasive tumour in a proportional fashion, covering up to 3 different components. A semi-automated arraying device was used (TMArrayer; Pathology Devices, Inc, Westminster, Md., USA). In addition, 2×1 mm cores were taken from areas with ITGCN from 15 cases and normal testis from 22 cases. From 15 cases who had undergone RPLND, 2–4×1 mm tissue cores were taken from 6/8 cases with residual tumour.

Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking Chamber® (Biocare Medical). Slides were placed in the Autostainer® (Dako) and endogenous peroxidase was initially blocked with $H_2O_2$ (Dako). The slides were incubated for 30 min at room temperature with the primary RBM3 monoclonal antibody 1B5 obtained as in Examples, Section 3, followed by incubation for 30 min at room temperature with goat anti-mouse peroxidase conjugated Envision®. Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

For the immunohistochemical analysis of RBM3, four μm TMA-sections were automatically pretreated using the PT-link system (DAKO, Copenhagen, Denmark) and then stained in a Techmate 500 (DAKO, Copenhagen, Denmark) with the RBM3 clone 1B5 antibody diluted 1:10000

All samples of immunohistochemically stained tissue were manually evaluated under the microscope and annotated by a certified pathologist. Annotation of each sample was performed using a simplified scheme for classification of IHC outcome. Each tissue sample was examined for representativity and immunoreactivity.

Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak-moderate=faint to medium immunoreactivity, or strong=distinct and strong immunoreactivity. Also fraction of stained cells was subjectively evaluated in accordance to standards used in clinical histo-pathological diagnostics and outcome was classified as: <2%, 2-25%, >25-75% or >75% immunoreactive cells of the relevant cell population. The skilled artisan will recognize that this annotation procedure is similar to a calculation of an Allred score, see e.g. Allred et al (1998) Mod Pathol 11(2), 155.

For statistical analyses, graphic presentation nucleic and cytoplasmic staining were combined to yield a staining score (SS) ranging from 0 to 3. Only intensity was considered, but most positive tumors had a fraction level of >50%. SS=0 was defines as absent expression, SS=1 was defined as a weak expression, SS=2 was defined as a moderate expression, and SS=3 was defined as a strong expression.

b) Results

Figure 20:
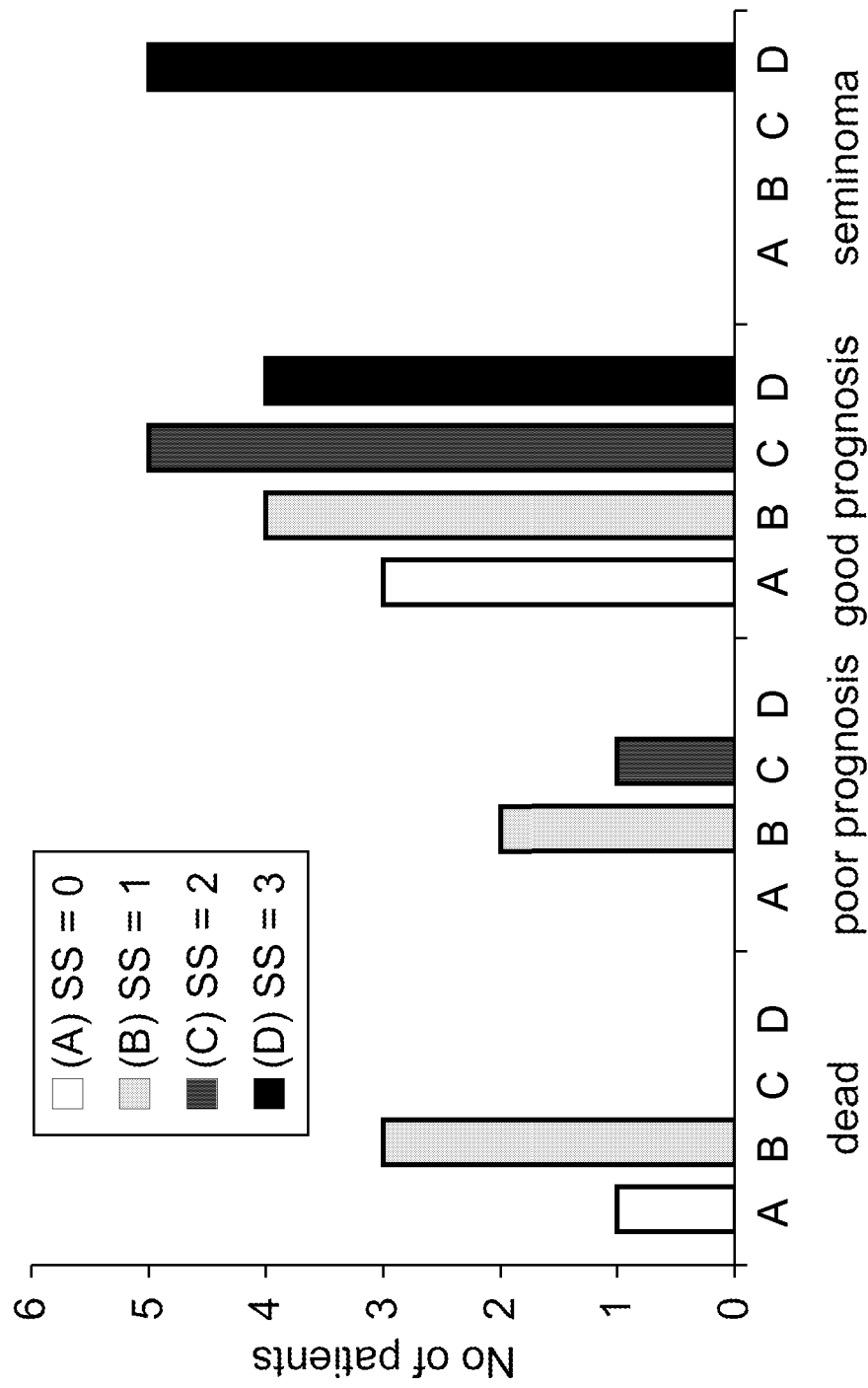
FIG. 20 shows RBM3 protein expression in testicular cancer patients. Patients were split into four different prognosis groups: poor prognosis, intermediate prognosis, good prognosis, and seminomas.

RBM3 expression was annotated as 0, 1, 2, or 3, with 3 denoting the highest staining score (SS). As can be seen in FIG. 20, RBM3 expression intensity correlates well with established prognostic categories. Patients that died from their disease all show a relatively low level of RBM3 expression. This is also true for most patients belonging to the poor prognosis category, while all patients with a really strong RBM3-expression (SS=3) and almost all patients with a strong RBM3 expression (SS=2) can be found in the good prognosis category. All patients with seminomas, which are well known to have a good prognosis, had a really strong RBM3 expression (SS=3).

Figure 21:
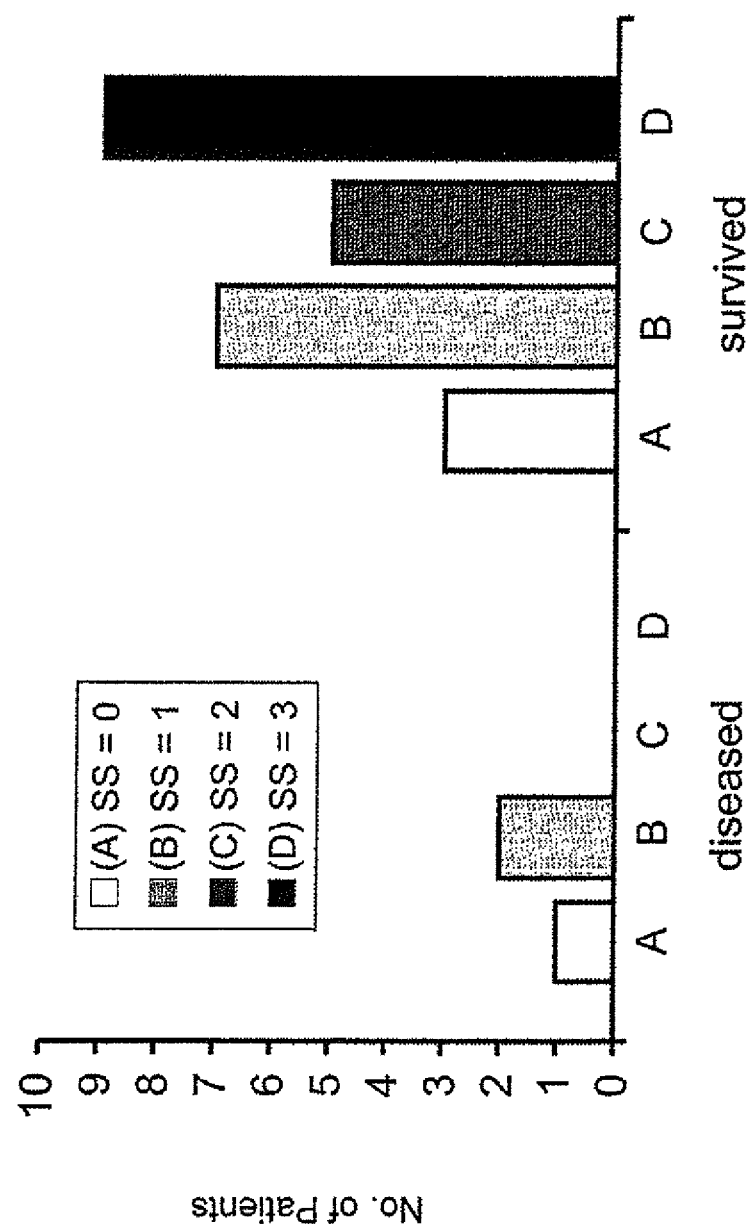
FIG. 21 shows the RBM3 protein expression in testicular cancer patients. Patients were split into two different groups: diseased or survived.

As can be seen in FIG. 21, there was a clear correlation between RBM3 protein expression and survival. There were no patients with high RBM3 protein expression among those that died from their disease. All patients with high RBM3 protein expression were alive at the end of the observation period.

Cell Culture Experiments

11. RBM3 Expression in Cisplatin Sensitive and Resistant Cell Lines
a) Material And Methods The expression of RBM3 protein in a cisplatin sensitive cell line (A2780) and a cisplatin resistant cell line (A2780-cp70) was analysed by Western Blot. Western blot was performed by separation of total protein extracts from selected human cell lines on 17% SDS-PAGE gels under reducing conditions, followed by electro-transfer to PVDF membranes (Bio-Rad Laboratories) according to the manufacturer's recommendations. The membranes were blocked (5% BSA in 1×PBS with 0.1% Tween20) for 1 h at room temperature, incubated with the primary affinity purified antibody (diluted 1:1000 in blocking buffer) and washed in PBST. The secondary HRP-conjugated antibody (sheep anti-mouse immunoglobulin/HRP, GE) was diluted 1:10000 in blocking buffer and chemiluminescence detection was carried out using a Chemidoc™ CCD camera (Bio-Rad Laboratories) and Western Blotting Luminol Reagent (Santa Cruz Biotechnologies, Inc), according to the manufacturer's protocol.
b) Results The results of the Western blot analysis is shown in FIG. 22. The expression of RBM3 protein is lower in the cisplatin resistant cells (A2780-cp70) than in the cisplatin sensitive cells (A2780). All antibodies used (anti-RBM3, 6F11, 1B5), show a similar result.

Further, the monoclonal antibodies 6F11 and 1B5 are shown to be more selective for the RBM3 protein than the polyclonal antibody anti-RBM3. Also 1B5 is shown to be more selective than 6F11.

12. Verification of Differential Response to Cisplatin Treatment
a) Material and Methods The effect of cisplatin on cell viability was determined by the WST-1 assay (Roche Applied Science) according to the manufacturer's recommendation. A2780 and A2780-Cp70 cells were seeded in 96-well plates at the density of 2500 cells/well in 100 μl appropriate medium a day before addition of cisplatin. The cells were treated with cisplatin (0-100 μM) for 48 h. Samples were made in triplicate. Ten microliters WST-1 solution was added per well and cells were incubated at 37° C. for 4 hr. The absorbance of each well was measured using a scanning multiwell spectrophotometer, ELISA reader at the wavelength of 450 nm and reference wavelength of 690 nm.

b) Results

Figure 23:
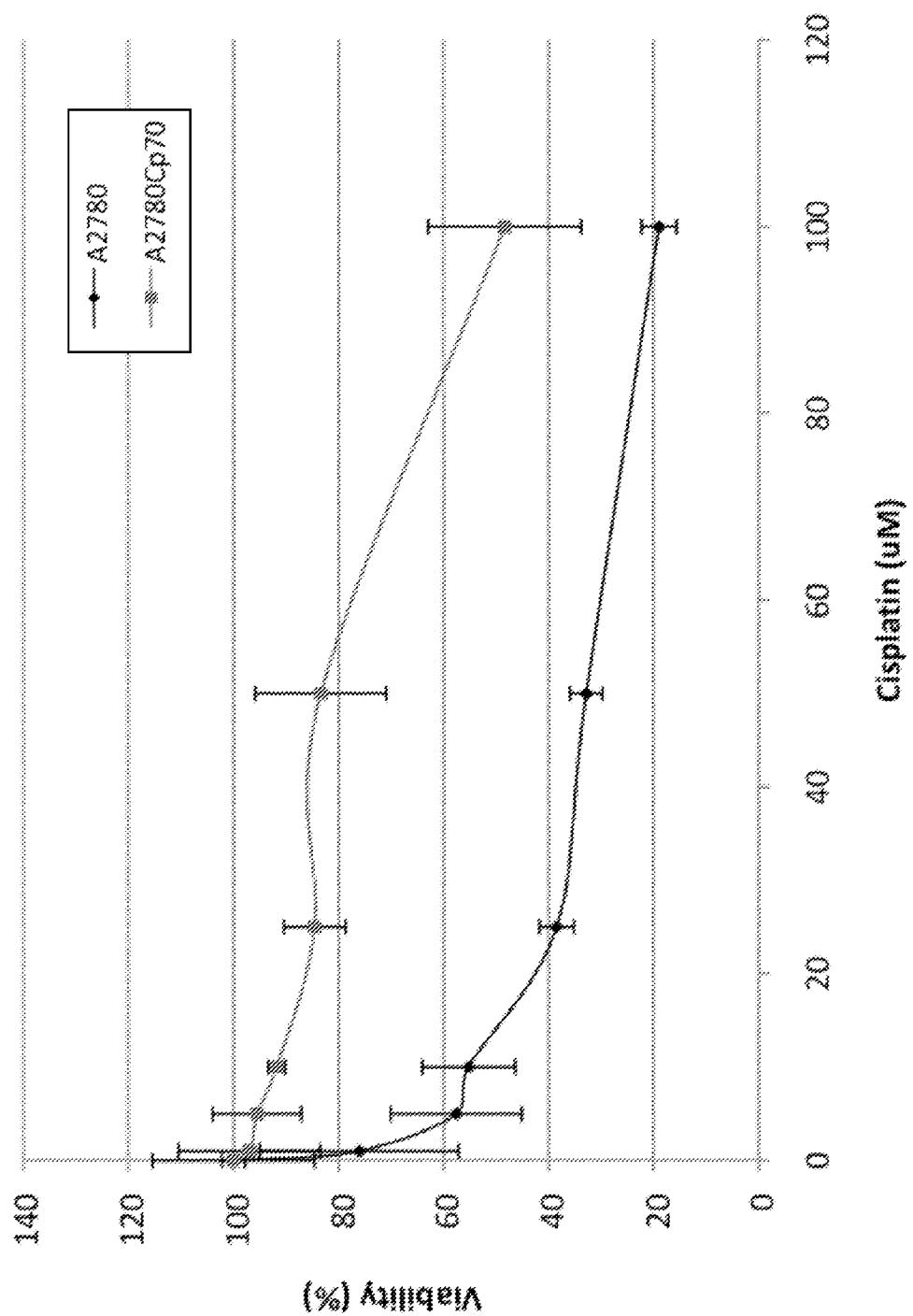
FIG. 23 shows viability in percent after cisplatin treatment in cisplatin sensitive (A2780) and cisplatin resistant (A2780-cp70) cell lines. Cells were treated with cisplatin for 48 h before analyzing viability.

When analysing viability of A2780 and A2780-cp70 cells after cisplatin treatment, it is clearly shown that the cisplatin resistant A2780-cp70 cells have an increased viability when compared to the parental A2780 cells (FIG. 23).

13. Effect of RBM3 Knockdown on Cisplatin Resistance a) Material and Methods

The human ovarian cancer cell line A2780 and the cisplatin-resistant variant A2780 Cp70 were maintained in RPMI-1640 supplemented with glutamine, 10% fetal bovine serum and 1% penicillin/streptomycin in a humidified incubator of 5% $CO_2$ at 37° C. Cisplatin (Sigma) was dissolved in 0.9% NaCl to a stock solution of 1 mg/ml and added to cell cultures to the final concentration (1-100 µM).

Transfection with siRNA against RBM3 (Applied Biosystems, Carlsbad, Calif.) or control siRNA (Applied Biosystems) was performed with Lipofectamine 2000 (Invitrogen, Carlsbad, Calif.) with a final concentration of 50 nM siRNA.

The effect of cisplatin on cell viability was determined by the WST-1 assay as described in Examples, section 12.

b) Results

Figure 24:
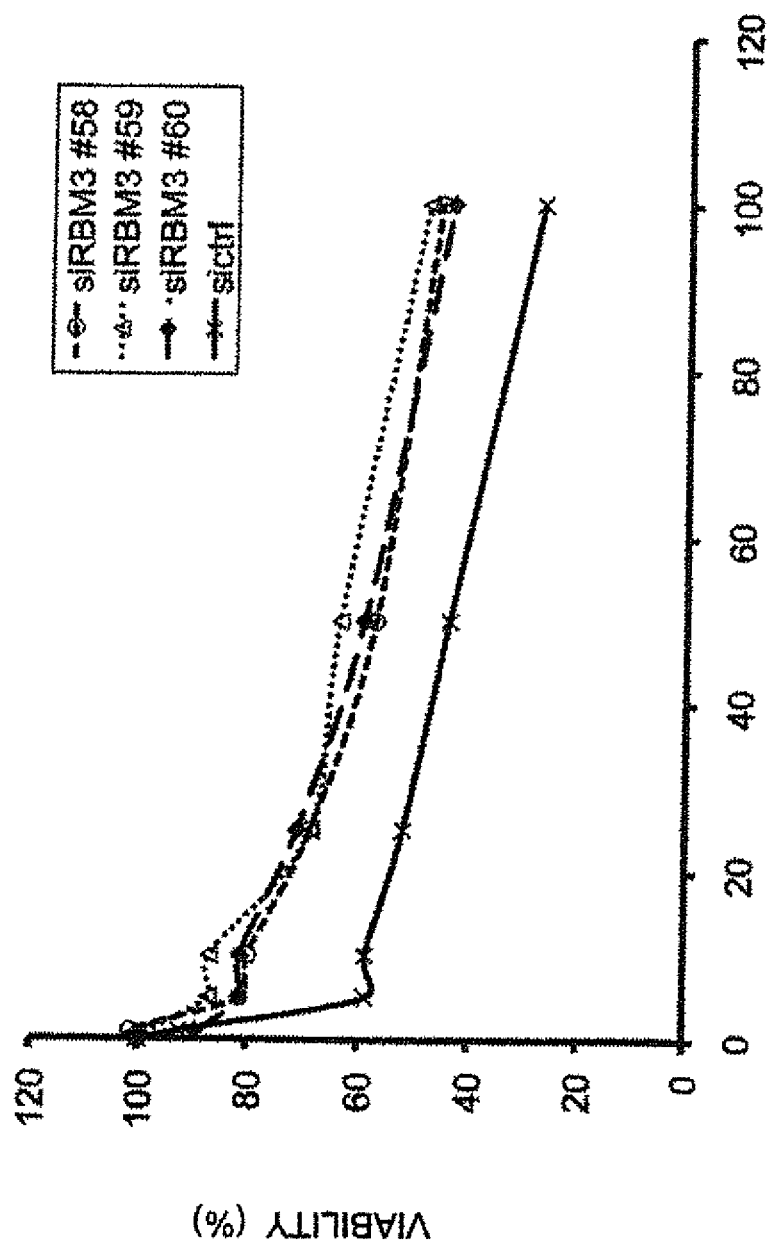
FIG. 24 shows viability in percent after cisplatin treatment in cells treated with three different anti-RBM3 siRNA (dotted lines) as well as in control cells not exposed to siRNA treatment (solid line)

A low RBM3 protein expression leads to an increased viability of cisplatin sensitive cells after cisplatin treatment, as shown in FIG. 24. There is a marked difference in viability in the cells exposed to different RBM3 siRNA, when compared to the non-exposed cells. These results show that a low RBM3 protein expression indicates cisplatin resistance, and that a high RBM3 protein expression indicates cisplatin sensitivity.

Establishment of a Treatment Prediction

14. A Non-Limiting Example

Following the establishment of a cancer in a patient, a tumor tissue sample from the patient is obtained. The tumor tissue sample may be obtained from a specimen from an earlier surgical removal of the tumor or from a tumor biopsy. Further, for the provision of a "negative reference", a sample is taken from archival material comprising tissue having low, or essentially lacking, RBM3 protein expression. Such archival tissue may for example be tissue having a pre-established low RBM3 protein expression level from the same cancer type as the one of the tested subject. Further, for the provision of a "positive reference", a sample is taken from archival material comprising tissue having high RBM3 protein expression, such as malignant melanoma tissue having a pre-established high RBM3 protein expression level, also from the same cancer type as the one of the tested subject.

The sample material is fixated in buffered formalin and histo-processed in order to obtain thin sections (4 µm) of the sample material.

Immunohistochemistry is performed in line with what is described in Examples, Section 8. One or more sample sections from each sample is/are mounted on glass slides that are incubated for 45 min in 60° C., de-paraffinized (if the sample in question was paraffinized) in xylene (2×15 min) and hydrated in graded alcohols. For antigen retrieval, slides are immersed in TRS (Target Retrieval Solution, pH 6.0, DakoCytomation) and boiled for 4 min at 125° C. in a Decloaking Chamber® (Biocare Medical). Slides are placed in the Autostainer® (DakoCytomation) and endogenous peroxidase is initially blocked with $H_2O_2$ (DakoCytomation). The reason for mounting multiple sample sections is to increase the accuracy of the results.

A primary RBM3 protein specific antibody (e.g. a monoclonal antibody obtained as in Example, Section 3) is added to the slides and incubated for 30 min in room temperature, followed by 30 min of incubation in room temperature with a labeled secondary antibody; e.g. goat-anti-mouse peroxidase conjugated Envision®. To detect the secondary antibody, diaminobenzidine (DakoCytomation) is used as chromogen, contrasted with a Harris hematoxylin (Sigma-Aldrich) counterstaining. Between all steps, slides are rinsed in wash buffer (DakoCytomation). The slides are then mounted with Pertex® (Histolab) mounting media.

Optionally, two control cell-lines may be used as a tool to validate the staining procedure; e.g. one slide with cells expressing RBM3 protein (positive cell line) and one slide having cells with indistinct weak or no RBM3 protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the other slides, i.e. incubated with the same primary and secondary antibodies.

For example, the tumor tissue slides from the subject, the staining reference slides, and optionally, the slides with control cell-lines, may be scanned in a light microscope using a ScanScope T2 automated slide scanning system (Aperio Technologies) at ×20 magnification. However, this scanning step is not necessary, but may make the procedure easier if, for example, the preparation and staining of the slides and the evaluation of the stained slides (see below) are performed at different locations or by different persons.

If control cell-lines are used, these are inspected to validate the staining procedure. If the cell-lines display staining results outside acceptable criteria, e.g. staining artifacts recognized by the skilled artisan, the staining of the tissue samples is considered invalid and the whole staining procedure is repeated with new slides. If the positive and negative cell-lines display strong staining intensity and indistinct weak or no staining intensity, respectively, the staining is considered as valid.

The stained sample slide(s) from the tumor tissue is/are evaluated manually by visual inspection in accordance to standards used in clinical histo-pathological diagnostics, and the immunoreactivity of the colorectal cancer slide(s) is/are graded in accordance with Examples, Section 8 above.

That is, the nuclear intensity, the nuclear fraction, the cytoplasmic intensity and/or the cytoplasmic fraction is/are determined to obtain one or more sample values. The person performing the evaluation and determination is aided by visual inspection of the stained positive and negative reference slides.

The sample value(s) from the tumor tissue sample from the patient is/are then compared to a reference value. If more than one sample slide are evaluated and thereby more than one sample value are obtained, the sample value that is compared to the reference value may be a mean or median value of the obtained sample values.

If the monoclonal antibody 1B5 is employed, the reference value may be an absent nuclear and/or cytoplasmic intensity.

If the sample value(s) is/are higher than the reference value, the physician responsible for the treatment of the patient concludes that the patient's responsiveness to platinum-based treatment is relatively high and optionally, that the patient should be given a platinum-based treatment.

If however the sample value(s) is/are lower than or equal to the reference value, the physician concludes that the patient's responsiveness to platinum-based treatment is relatively low and, optionally, that the patient therefore should be given a platinum-based treatment of a higher intensity (such as a higher dose) if the patient suffers from testicular or ovarian cancer and to refrain from platinum-based treatment if the subject suffers from any other type of cancer.

The invention claimed is:

1. A method for determining whether to treat a mammalian subject having a cancer with a platinum-based treatment, comprising the steps of:
   a) evaluating the amount of RBM3 protein or RBM3 mRNA present in at least part of a sample from said subject, and determining a sample value corresponding to said amount;
   b) comparing the sample value obtained in step a) with a reference value; and,
   if said sample value is higher than said reference value,
   c1) applying a platinum-based treatment to said subject, and
   if said sample value is lower than or equal to said reference value,
   c2) refraining from applying a platinum-based treatment to the subject.

2. The method according to claim 1, wherein said cancer is selected from the group consisting of testicular, ovarian, lung, bladder, colorectal, cervical, breast and head and neck cancer.

3. The method according to claim 2, wherein said cancer is selected from the group consisting of testicular and ovarian cancer.

4. The method according to claim 1, wherein said platinum-based treatment is selected from the group consisting of carboplatin, paraplatin, oxaliplatin, satraplatin, picoplatin and cisplatin treatment.

5. The method according to claim 1, wherein said sample comprises tumor cells from said subject.

6. The method according to claim 1, wherein the reference value of step b) corresponds to a reference sample having no detectable RBM3 protein or RBM3 mRNA.

7. The method according to claim 1, wherein step a) comprises:
   aI) applying to said sample a quantifiable affinity ligand capable of selective interaction with the RBM3 protein to be evaluated, said application being performed under conditions that enable binding of the affinity ligand to RBM3 protein present in the sample; and
   aII) quantifying the affinity ligand bound to said sample to evaluate said amount;
   wherein the quantifiable affinity ligand is selected from the group consisting of antibodies and antigen-binding fragments thereof that bind to RBM3.

8. The method according to claim 7, wherein said quantifiable affinity ligand is capable of selective interaction with a peptide whose amino acid sequence consists of a sequence SEQ ID NO:1.

9. The method according to claim 1, wherein step a) comprises evaluating the amount of RBM3 mRNA by means of a microarray, a PCR amplification, a RNA hybridization, a gel electrophoresis or a combination thereof to obtain said amount.

10. A method of determining the level of intensity of platinum-based treatment with which to treat a mammalian subject having a cancer, comprising the steps of:
   a) evaluating the amount of RBM3 protein or RBM3 mRNA present in at least part of a sample from said subject, and determining a sample value corresponding to said amount;
   b) comparing the sample value obtained in step a) with a reference value; and,
   if said sample value is higher than said reference value,
   c1) applying a platinum-based treatment of a first intensity to said subject; and
   if said sample value is lower than or equal to said reference value,
   c2) applying a platinum-based treatment of a second intensity to said subject,
   wherein said second intensity is higher than said first intensity; and
   wherein said second intensity is a treatment that is applied more frequently, in higher individual doses, and/or for a longer period than the treatment of the first intensity.

11. The method according to claim 10, wherein said cancer is selected from the group consisting of testicular, ovarian, lung, bladder, colorectal, cervical, breast and head and neck cancer.

12. The method according to claim 11, wherein said cancer is selected from the group consisting of testicular and ovarian cancer.

13. The method according to claim 10, wherein said platinum-based treatment is selected from the group consisting of carboplatin, paraplatin, oxaliplatin, satraplatin, picoplatin and cisplatin treatment.

14. The method according to claim 10, wherein said sample comprises tumor cells from said subject.

15. The method according to claim 10, wherein the reference value of step b) corresponds to a reference sample having no detectable RBM3 protein or RBM3 mRNA.

16. The method according to claim 10, wherein step a) comprises:
   aI) applying to said sample a quantifiable affinity ligand capable of selective interaction with the RBM3 protein to be evaluated, said application being performed under conditions that enable binding of the affinity ligand to RBM3 protein present in the sample; and
   aII) quantifying the affinity ligand bound to said sample to evaluate said amount;
   wherein the quantifiable affinity ligand is selected from the group consisting of antibodies and antigen-binding fragments thereof that bind to RBM3.

17. The method according to claim 16, wherein said quantifiable affinity ligand is capable of selective interaction with a peptide whose amino acid sequence consists of a sequence SEQ ID NO:1.

18. The method according to claim 10, wherein step a) comprises evaluating the amount of RBM3 mRNA by means of a microarray, a PCR amplification, a RNA hybridization, a gel electrophoresis or a combination thereof to obtain said amount.

* * * * *

UNITED STATES PATENT AND TRADEMARK OFFICE
CERTIFICATE OF CORRECTION

Page 1 of 1

PATENT NO.        : 8,747,910 B2
APPLICATION NO.   : 13/201689
DATED             : June 10, 2014
INVENTOR(S)       : Jirström et al.

It is certified that error appears in the above-identified patent and that said Letters Patent is hereby corrected as shown below:

In the Specification

Column 32, Line 62: Please correct "20 mM (3-mercaptoethanol;"
to read -- 20 mM β-mercaptoethanol; --

Column 43, Line 37: Please correct "of NF 75%" to read -- of NF<75% --

Signed and Sealed this
Thirteenth Day of January, 2015

Michelle K. Lee
*Deputy Director of the United States Patent and Trademark Office*